(12) United States Patent
Haber et al.

(10) Patent No.: US 12,077,603 B2
(45) Date of Patent: *Sep. 3, 2024

(54) MULTISPECIFIC ANTIGEN-BINDING MOLECULES FOR CELL TARGETING AND USES THEREOF

(71) Applicant: Regeneron Pharmaceuticals, Inc., Tarrytown, NY (US)

(72) Inventors: Lauric Haber, Rye Brook, NY (US); Jennifer A. Finney, Park Ridge, NJ (US); Ryan McKay, Peekskill, NY (US); Eric Smith, New York, NY (US); Chia-Yang Lin, Scarsdale, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 860 days.

This patent is subject to a terminal disclaimer.

(21) Appl. No.: 16/993,721

(22) Filed: Aug. 14, 2020

(65) Prior Publication Data

US 2021/0047438 A1 Feb. 18, 2021

Related U.S. Application Data

(60) Provisional application No. 63/057,824, filed on Jul. 28, 2020, provisional application No. 62/978,584, filed on Feb. 19, 2020, provisional application No. 62/924,435, filed on Oct. 22, 2019, provisional application No. 62/887,411, filed on Aug. 15, 2019.

(51) Int. Cl.
| | |
|---|---|
| *C07K 16/00* | (2006.01) |
| *C07K 14/725* | (2006.01) |
| *C07K 14/74* | (2006.01) |
| *C07K 16/46* | (2006.01) |

(52) U.S. Cl.
CPC ........ *C07K 16/468* (2013.01); *C07K 14/7051* (2013.01); *C07K 14/70539* (2013.01); *C07K 2317/31* (2013.01); *C07K 2317/52* (2013.01); *C07K 2317/55* (2013.01); *C07K 2317/622* (2013.01)

(58) Field of Classification Search
None
See application file for complete search history.

(56) References Cited

U.S. PATENT DOCUMENTS

| | | | |
|---|---|---|---|
| 7,550,143 B2 * | 6/2009 | Chang | C07K 16/2803 |
| | | | 424/193.1 |
| 10,738,130 B2 | 8/2020 | Haber et al. | |
| 2006/0228300 A1 | 10/2006 | Chang et al. | |

FOREIGN PATENT DOCUMENTS

| | | |
|---|---|---|
| JP | 2014 124186 A | 7/2014 |
| WO | 91/03493 A1 | 3/1991 |
| WO | 14/022540 A1 | 2/2014 |
| WO | 18/178074 A1 | 10/2018 |
| WO | PCT/US2020/046352 | 8/2020 |

OTHER PUBLICATIONS

U.S. Appl. No. 17/716,830, Requirement for Restriction/Election mailed Aug. 17, 2022.
U.S. Appl. No. 17/716,830, Non-Final Office Action mailed Nov. 22, 2022.
U.S. Appl. No. 17/967,418, Requirement for Restriction/Election mailed Jan. 30, 2023.
Ellwanger et al., "Redirected optimized cell killing (ROCK): A highly versatile multispecific fit-for-purpose antibody platform for engaging innate immunity," MABS, vol. 11, (No. 5): 899-918, Jun. 7, 2019 (2019). [ISSN: 1942-0862, DOI: 10.1080/19420862.2019. 1616506 e.g. p. 903, fig. 3, in particular IgG-like ROCK Bi-scFv-IgAb; p. 905, left-hand column paragraph 2].
WIPO Application No. PCT/US2020/046352, PCT International Search Report and Written Opinion of the International Searching Authority mailed Nov. 16, 2020.
U.S. Appl. No. 62/978,584 filed Feb. 19, 2020, Pending.
U.S. Appl. No. 63/057,824, filed Jul. 28, 2020, Pending.
U.S. Appl. No. 62/887,411, filed Aug. 15, 2019, Expired.
U.S. Appl. No. 62/924,435, filed Oct. 22, 2019, Expired.
U.S. Appl. No. 62/978,584, filed Feb. 19, 2020, Expired.
U.S. Appl. No. 63/057,824, filed Jul. 28, 2020, Expired.
U.S. Appl. No. 17/716,830, filed Apr. 8, 2022, US-2022-0251244, Published.
U.S. Appl. No. 17/967,418, filed Oct. 17, 2022, US-2023-0068129, Published.
U.S. Appl. No. 17/716,830, Final Office Action mailed Mar. 31, 2023.
U.S. Appl. No. 17/967,418, Non-Final Office Action mailed Apr. 3, 2023.
U.S. Appl. No. 17/716,830, Non-Final Office Action mailed Aug. 29, 2023.
U.S. Appl. No. 17/967,418, Non-Final Office Action mailed Aug. 30, 2023.

* cited by examiner

*Primary Examiner* — Meera Natarajan
(74) *Attorney, Agent, or Firm* — Schwabe, Williamson & Wyatt PC; Eileen Woo

(57) ABSTRACT

The present invention provides multispecific antigen-binding molecules that bind both a T-cell antigen (e.g., CD3) and a target antigen (e.g., a tumor associated antigen, a viral or bacterial antigen), and which include a single polypeptide chain that is multivalent (e.g., bivalent) with respect to T-cell antigen binding, and uses thereof.

28 Claims, 31 Drawing Sheets
Specification includes a Sequence Listing.

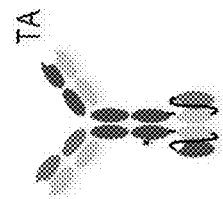
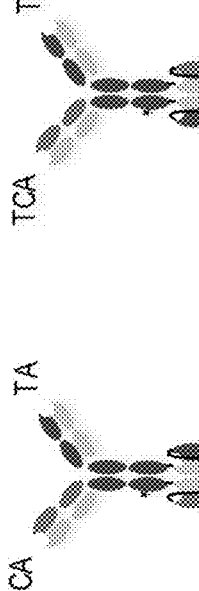
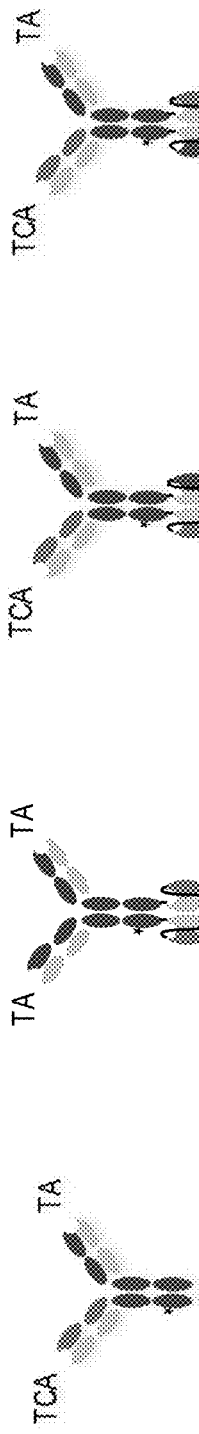
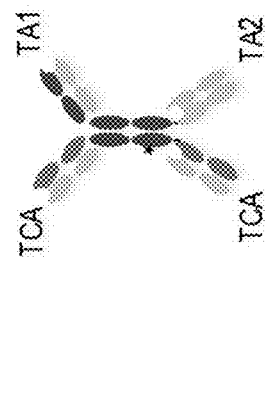
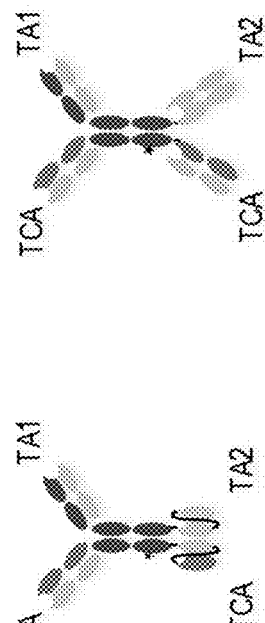
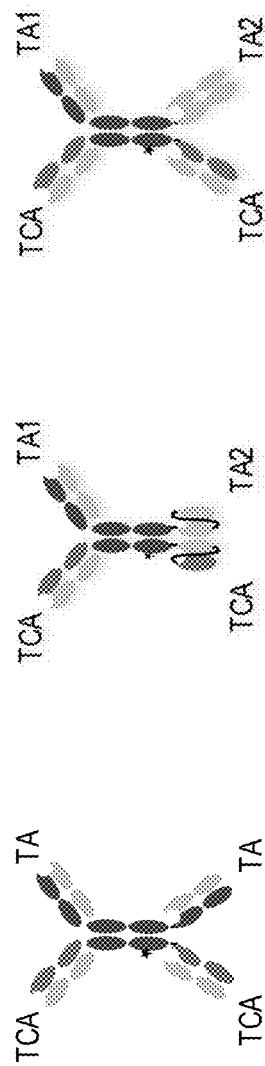
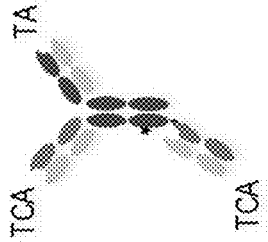
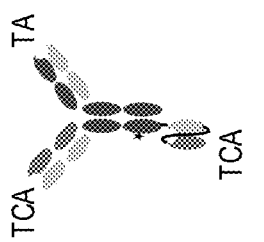
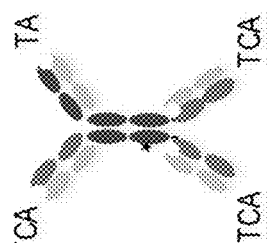
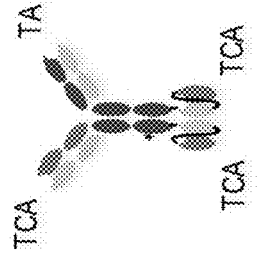

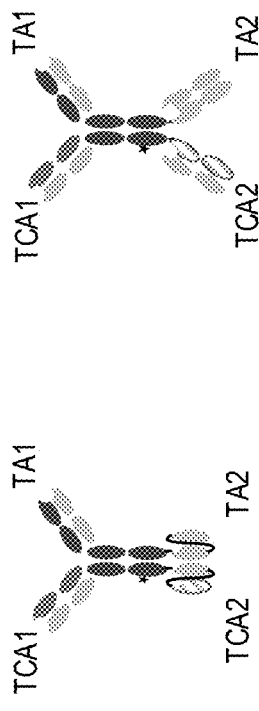
FIG. 1L
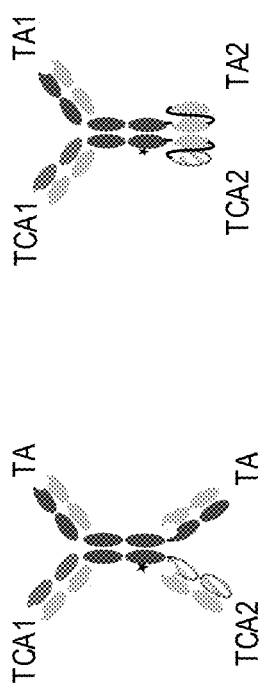
FIG. 1M
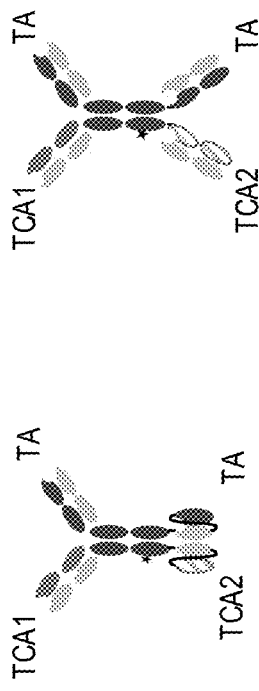
FIG. 1N
FIG. 1O
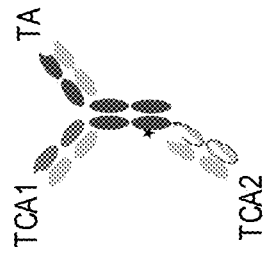
FIG. 1P
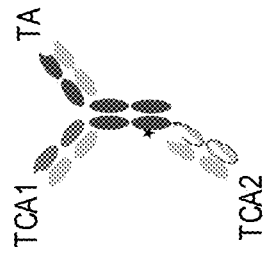
FIG. 1Q
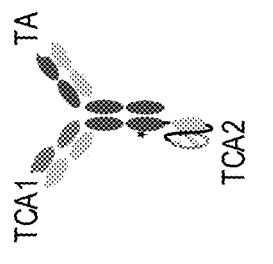
FIG. 1R
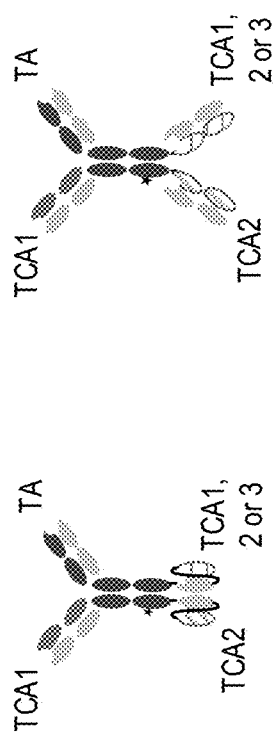
FIG. 1S

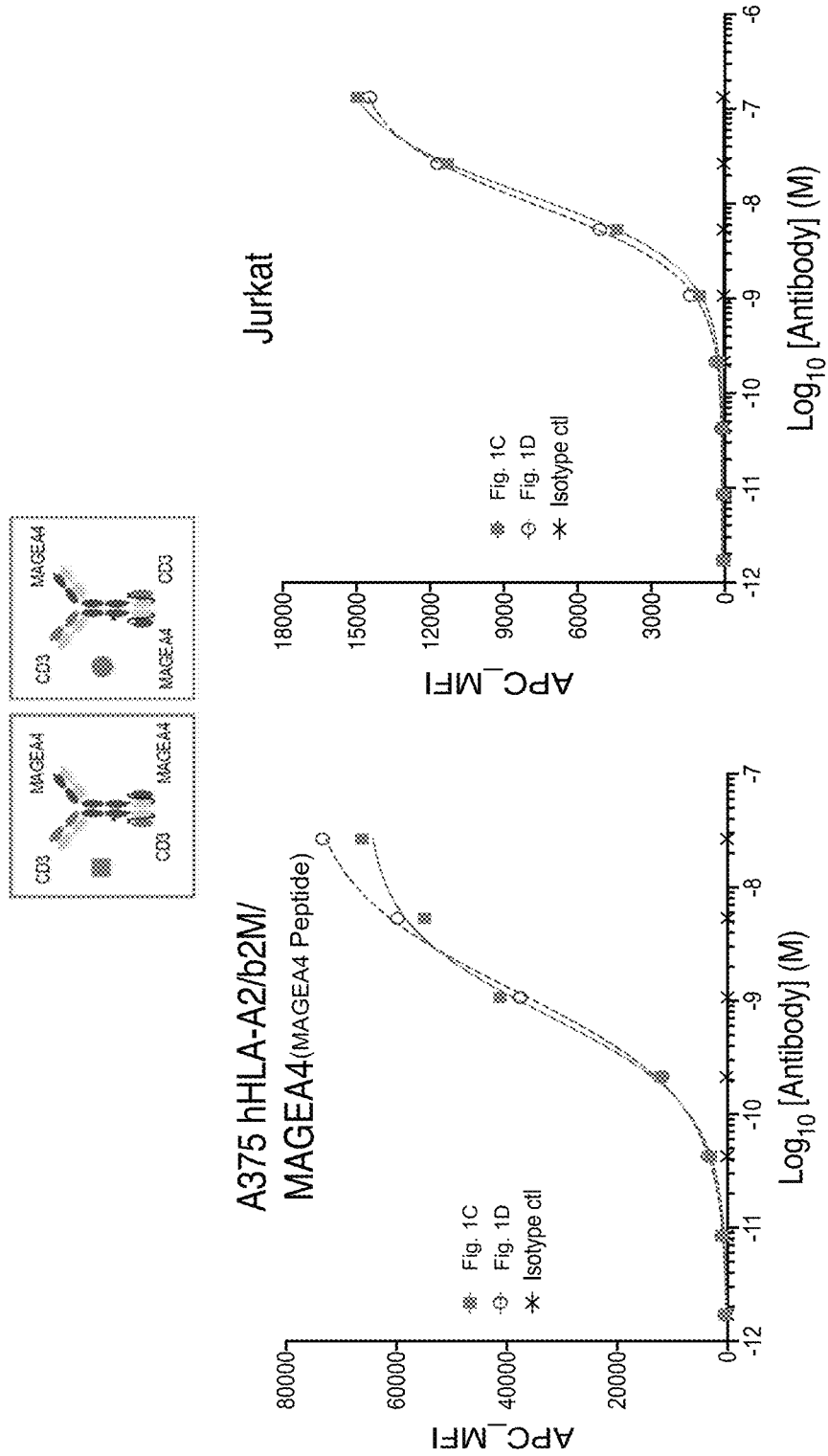

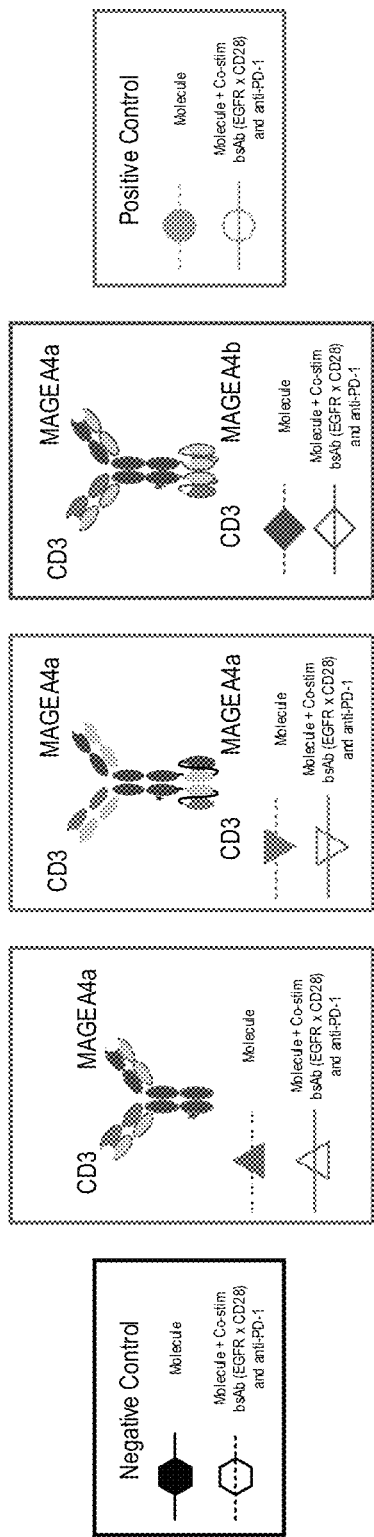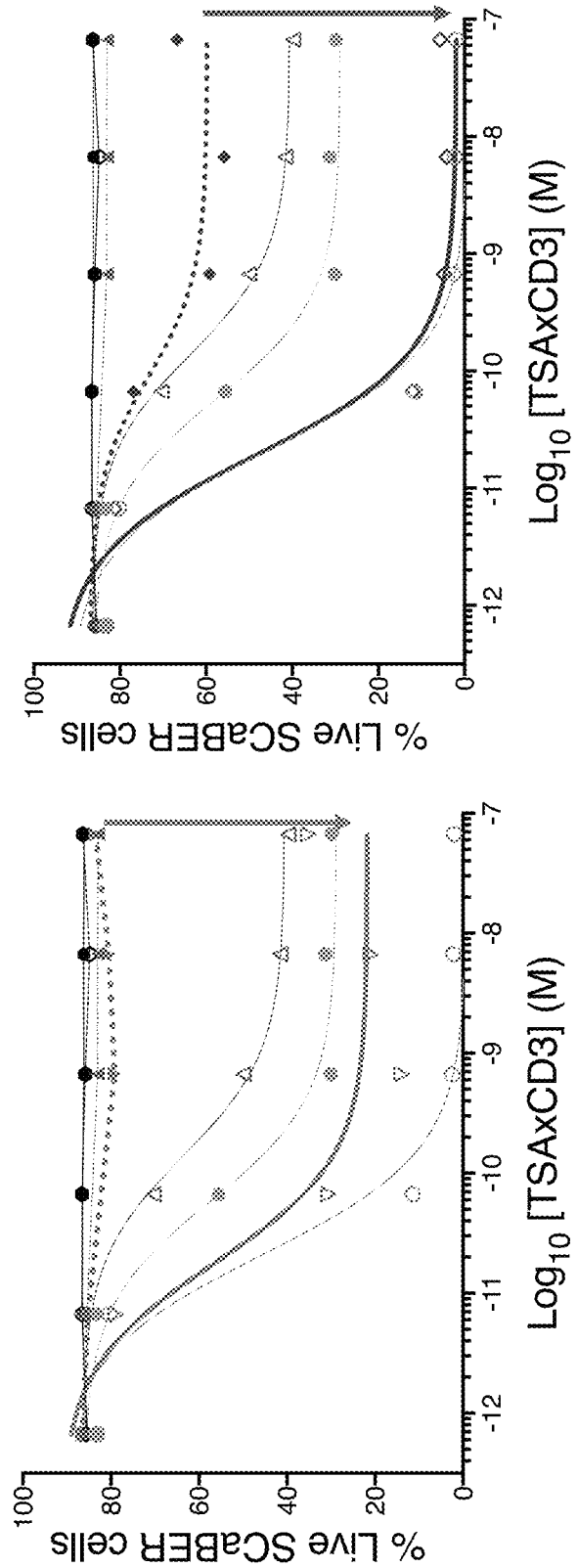
FIG. 12A
FIG. 12B

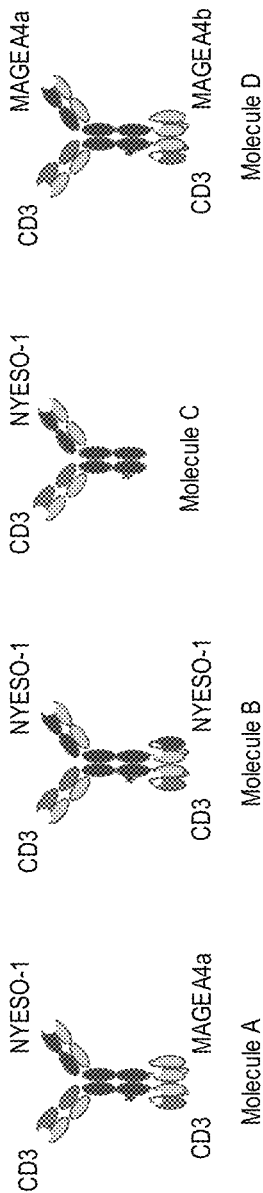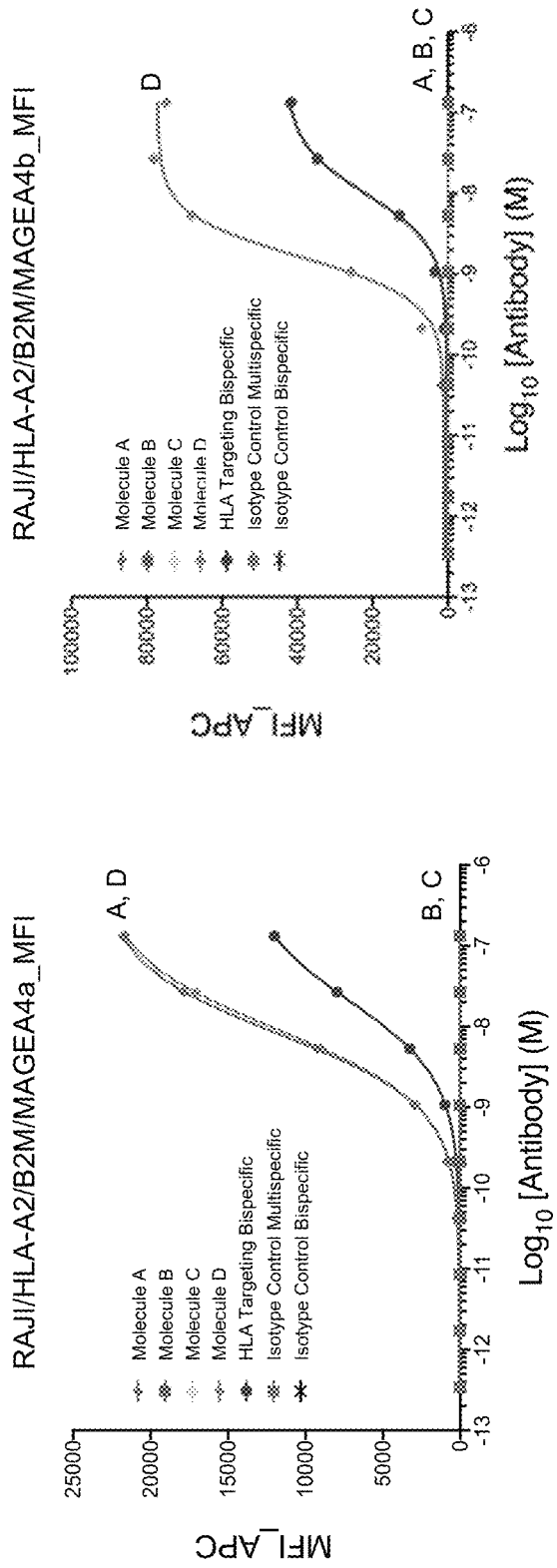
FIG. 16B
FIG. 16C

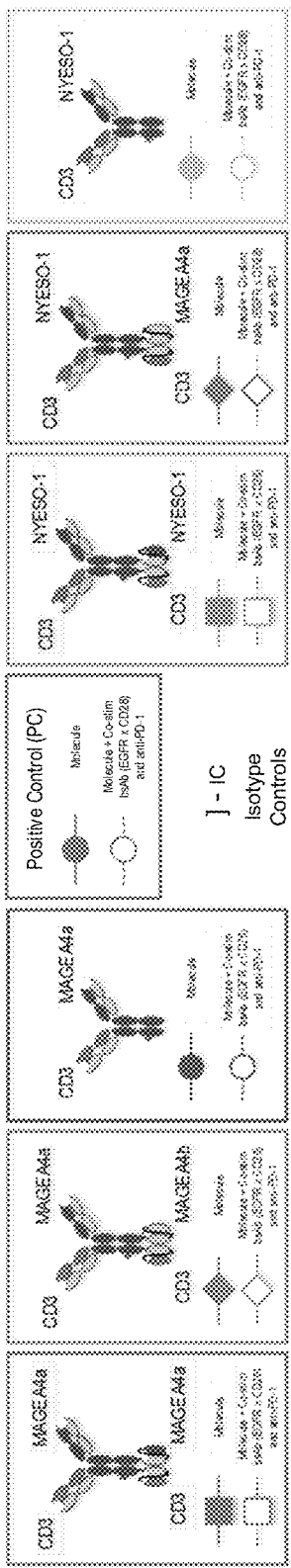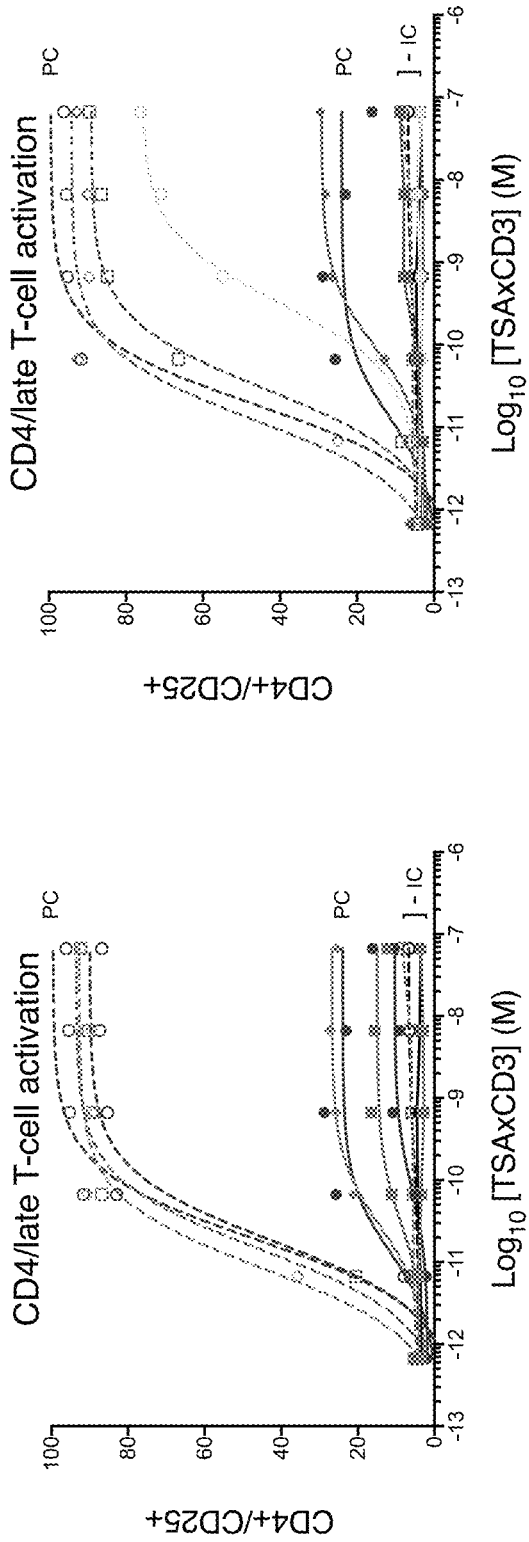
FIG. 18C
FIG. 18D

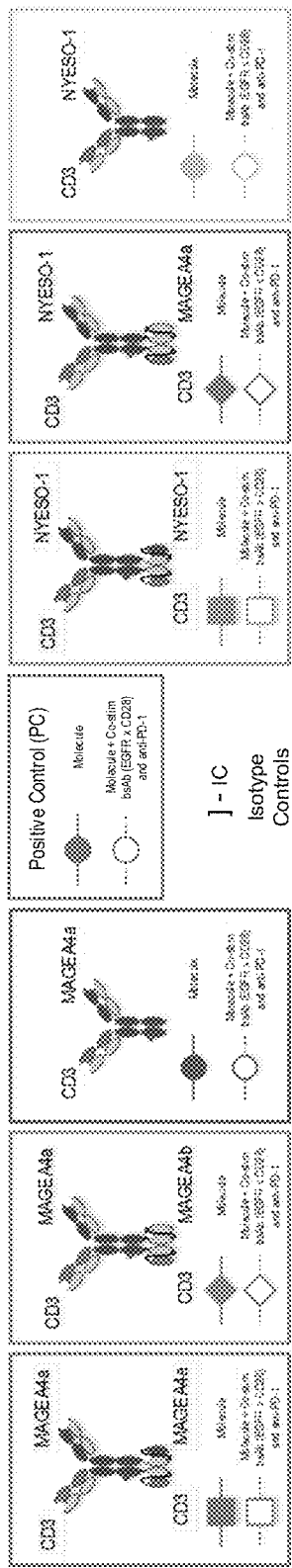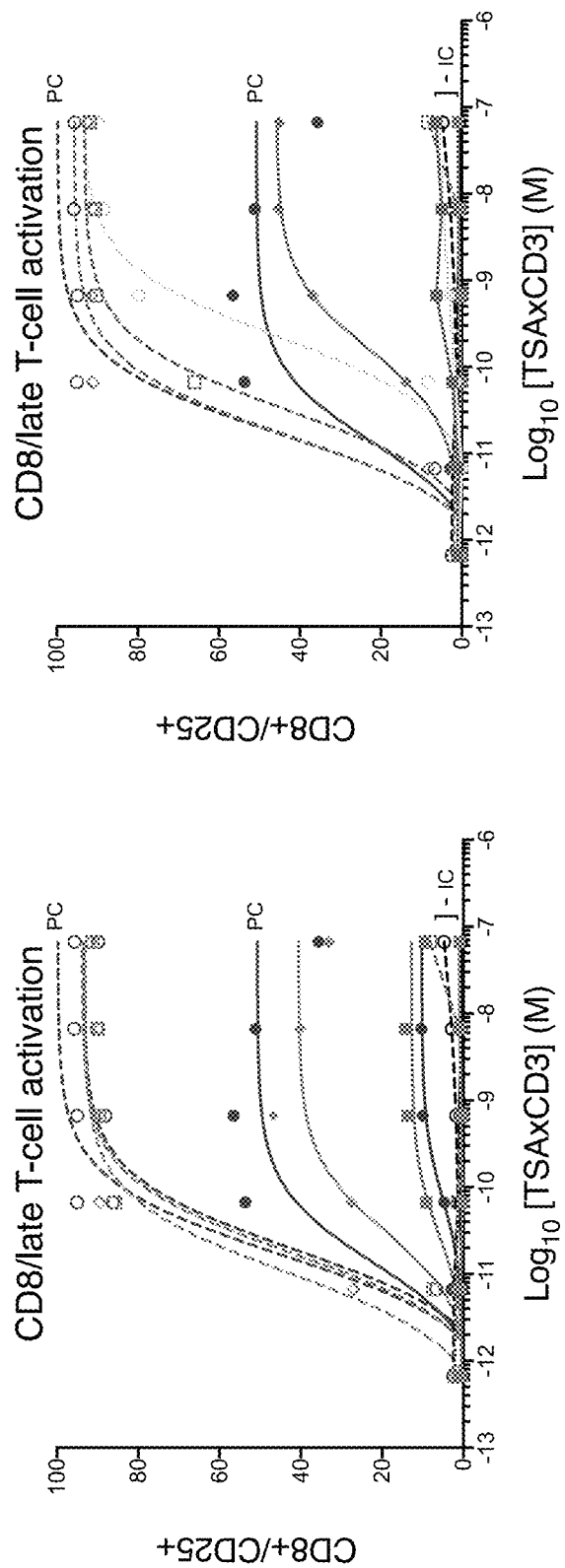
FIG. 18E
FIG. 18F

MULTISPECIFIC ANTIGEN-BINDING MOLECULES FOR CELL TARGETING AND USES THEREOF

CROSS-REFERENCE TO RELATED APPLICATIONS

This application claims the benefit under 35 USC § 119(e) of US Provisional Application Nos.: 62/887,411, filed Aug. 15, 2019; 62/924,435, filed Oct. 22, 2019; 62/978,584, filed Feb. 19, 2020; and 63/057,824, filed Jul. 28, 2020, each of which is incorporated herein by reference in its entirety for all purposes.

REFERENCE TO A SEQUENCE LISTING

This application incorporates by reference the Sequence Listing submitted in Computer Readable Form as file 10606US01_Revised_Sequence.txt, created on Apr. 16, 2024 and containing 67,978 bytes.

FIELD OF THE INVENTION

The present invention relates to alternative formats for multivalent antigen-binding proteins, and methods of use thereof. The multivalent antigen-binding proteins, including bispecific and multispecific molecules comprise a first polypeptide chain with both an N-terminal and a C-terminal antigen-binding domain that specifically binds a T-cell antigen (e.g., CD3), and a second polypeptide chain comprising at least one antigen-binding domain that binds a target antigen (e.g., a tumor cell antigen).

BACKGROUND

Bispecific and multispecific antibodies and antigen-binding molecules are known in the art (see, e.g., Brinkmann and Kontermann, *MABS*, 9(2):182-212, 2017). Among such known formats is the FcFc* (FIG. 1A structure), a traditional bispecific antibody with Fab antigen-binding domains on either arm of the antibody and an Fc region with a modified CH3 domain that changes Protein A binding affinity to permit isolation of the heterodimer from the homodimeric impurities (Id. at p. 184, FIG. 2, panel 7, last structure). This traditional bispecific antibody format has been used to make bispecific antibodies in which one arm of the antibody targets a tumor cell antigen and the second arm targets a T-cell antigen, such as CD3. Another conventional format is the IgG-HC-scFv (FIG. 1B structure), a bispecific antibody in which two N-terminal Fab domains bind a first antigen and two scFv domains linked to the C-terminus of the Fc region bind a second antigen (Id. at p. 184, FIG. 2, panel 10, first structure). There is a need in the art for new and useful formats for bispecific or multispecific antigen-binding molecules that improve desired functionalities. Although Brinkmann et al. generically references the "building blocks" for the generation of any homodimeric or heterodimeric antigen-binding molecule (p. 183, FIG. 1), the possibilities are virtually infinite, and only those molecules shown in FIG. 2 (p. 184) had reportedly been prepared. Moreover, Brinkmann doesn't contemplate specific antigen-binding domains, particularly a molecule comprising T-cell antigen binding domains at both the N-terminus and the C-terminus of a single polypeptide chain forming part of a multispecific molecule.

BRIEF SUMMARY OF THE INVENTION

In general, the present invention provides multispecific antigen-binding molecules that bind both a T-cell antigen (TCA) (e.g., CD3) and a target antigen (TA) (e.g., a tumor associated antigen, a viral or bacterial antigen), and which include a single polypeptide chain that is multivalent (e.g., bivalent) with respect to T-cell antigen binding.

In one aspect, the present invention provides a multispecific antigen-binding molecule, comprising: (a) a first polypeptide comprising, from N-terminus to C-terminus (i) a first antigen-binding domain that specifically binds a T cell antigen, (ii) a first multimerizing domain, and (iii) a second antigen-binding domain that specifically binds a T cell antigen; and (b) a second polypeptide comprising, from N-terminus to C-terminus (i) a third antigen-binding domain that specifically binds a target antigen, and (ii) a second multimerizing domain, wherein the first and the second multimerizing domains associate with one another to form the molecule.

In some embodiments, the second polypeptide further comprises a fourth antigen-binding domain at the C-terminus of the second multimerizing domain. In some cases, the fourth antigen-binding domain specifically binds a target antigen. In some cases, the third antigen-binding domain and the fourth antigen-binding domain specifically bind distinct target antigens. In some cases, the distinct target antigens are expressed (or present) on the surface of the same cell. In some cases, the distinct target antigens are expressed (or present) on the surface of different cells. References, herein, to a target antigen expressed (or present) on the surface of a cell include both a protein expressed by the cell that is embedded in or spans the cell's membrane, and a peptide presented in the context of the groove of a major histocompatibility complex (MHC) protein by the cell. In some cases, the third antigen-binding domain and the fourth antigen-binding domain specifically bind the same target antigen. In some embodiments, the fourth antigen-binding domain specifically binds a T cell antigen. In some cases, the first antigen-binding domain and the second antigen-binding domain specifically bind the same T-cell antigen. In some cases, the first antigen-binding domain and the second antigen-binding domain specifically bind distinct T-cell antigens. In some embodiments, the first antigen-binding domain specifically binds a first T-cell antigen that is a co-stimulatory molecule, and the second antigen-binding domain specifically binds a second T-cell antigen that is a check-point inhibitor. In some cases, the co-stimulatory molecule is CD28 and the check-point inhibitor is PD-1. In some cases, the first, second and fourth antigen-binding domains specifically bind the same T-cell antigen. In some cases, the first, second and fourth antigen-binding domains bind distinct T-cell antigens. In some cases, the first and fourth antigen-binding domains specifically bind the same T-cell antigen. In some cases, the second and fourth antigen-binding domains specifically bind the same T-cell antigen.

In various embodiments, one or more of the antigen-binding domains is a Fab. In various embodiments, one or more of the antigen-binding domains is a scFv. In some embodiments, the multispecific molecules contain both Fab and scFv antigen-binding domains. In some cases, the first antigen-binding domain and the third antigen-binding domain are Fabs. In some cases, the second antigen-binding domain is an scFv. In some cases, the fourth antigen-binding domain is an scFv. In some embodiments, the first, second and third antigen-binding domains are Fabs. In some cases, the first and third antigen-binding domains are Fab domains, and the second antigen-binding domain is an scFv domain. In some embodiments, the first, second, third and fourth antigen-binding domains are Fabs. In some cases, the first, second, third and fourth antigen-binding domains are Fab domains. In some cases, the first and third antigen-binding domains are Fab domains, and the second and fourth antigen-binding domains are scFv domains. In some cases, the first, second, third and fourth antigen-binding domains are Fab domains. In some cases, the first and third antigen-binding domains are Fab domains, and the second and fourth antigen-binding domains are scFv domains. In some cases, the first, second, third and fourth antigen-binding domains are Fab domains.

In any embodiments in which the antigen-binding domain is an scFv domain, the scFv domain may comprise a heavy chain variable region (HCVR) comprising a cysteine mutation at residue 44, and a light chain variable region comprising a cysteine mutation at residue 100 (Kabat numbering). In some cases, the scFv comprises a HCVR and a LCVR joined together via a polypeptide linker of from 10 to 30 amino acids, optionally a (G4S)$_4$ linker (SEQ ID NO: 174). In some embodiments, the scFv is connected to the C-terminus of the first and/or second multimerizing domain via a linker of from 5 to 25 amino acids, optionally a (G4S)$_3$ linker (SEQ ID NO: 173).

In some embodiments, the T cell antigen is a T cell receptor complex antigen (i.e., any of the protein subunits that make up the T cell receptor complex). In some cases, the T cell antigen is CD3. In some cases, the T cell antigen is a co-stimulatory molecule or a check-point inhibitor on a T cell. In some embodiments, the T cell antigen is selected from the group consisting of CD27, CD28, 4-1BB and PD-1. In some embodiments, the T cell antigen is selected from the group consisting of CD3, CD27, CD28, 4-1BB and PD-1.

In some embodiments, the target antigen is a tumor-associated antigen. In some embodiments, the target antigen is a viral or bacterial antigen. In some embodiments, the target antigen is a fungal antigen or a parasite antigen.

In some embodiments, the first and second multimerizing domains are immunoglobulin Fc domains. In some cases, the first multimerizing domain and the second multimerizing domain are human IgG1 or human IgG4 Fc domains. In some cases, the first and second multimerizing domains comprise an immunoglobulin hinge domain, a CH2 domain and a CH3 domain of a human IgG polypeptide (e.g., IgG1, IgG2, IgG3 or IgG4). In some cases, the first and second multimerizing domains comprise a hinge domain, a CH2 domain and a CH3 domain of a human IgG1 polypeptide. In some cases, the first and second multimerizing domains comprise a hinge domain, a CH2 domain and a CH3 domain of a human IgG4 polypeptide. In some embodiments, the first and second multimerizing domains associate with one another via disulfide bonding.

In some embodiments, the first multimerizing domain or the second multimerizing domain comprises an amino acid substitution that reduces affinity for Protein A binding compared to a wild-type Fc domain of the same isotype. In some cases, the amino acid substitution comprises an H435R modification, or H435R and Y436F modifications (EU numbering). In some cases, the first multimerizing domain comprises the H435R and Y436F modifications. In some cases, the second multimerizing domain comprises the H435R and Y436F modifications. In some embodiments, the first polypeptide, the second polypeptide, or both the first and the second polypeptides comprise a modified hinge domain that reduces binding affinity for an Fcγ receptor relative to a wild-type hinge domain of the same isotype.

In another aspect, the present invention provides a multispecific antigen-binding molecule, comprising: (a) a first polypeptide comprising, from N-terminus to C-terminus (i) a first Fab that specifically binds a T cell antigen, (ii) a first immunoglobulin Fc domain, and (iii) a first scFv that specifically binds a T cell antigen; and (b) a second polypeptide comprising, from N-terminus to C-terminus (i) a second Fab that specifically binds a target antigen, (ii) a second immunoglobulin Fc domain, and (iii) a second scFv that specifically binds a target antigen, wherein the first and the second immunoglobulin domains associate with one another via disulfide bonding to form the molecule.

In some embodiments, the second Fab and the second scFv specifically bind distinct target antigens. In some cases, the distinct target antigens are expressed on the surface of the same cell. In some embodiments, the second Fab and the second scFv specifically bind the same target antigen.

In another aspect, the present invention provides a multispecific antigen-binding molecule, comprising: (a) a first polypeptide comprising, from N-terminus to C-terminus (i) a first Fab that specifically binds a T cell antigen, (ii) a first immunoglobulin Fc domain, and (iii) a second Fab that specifically binds a T cell antigen; and (b) a second polypeptide comprising, from N-terminus to C-terminus (i) a third Fab that specifically binds a target antigen, (ii) a second immunoglobulin Fc domain, and (iii) a fourth Fab that specifically binds a target antigen, wherein the first and the second immunoglobulin domains associate with one another via disulfide bonding to form the molecule.

In some embodiments, the third Fab and the fourth Fab specifically bind distinct target antigens. In some cases, the distinct target antigens are expressed on the surface of the same cell. In some embodiments, the third Fab and the fourth Fab specifically bind the same target antigen.

In another aspect, the present invention provides a multispecific antigen-binding molecule, comprising: (a) a first polypeptide comprising, from N-terminus to C-terminus (i) a first Fab that specifically binds a T cell antigen, (ii) a first immunoglobulin Fc domain, and (iii) a first scFv that specifically binds a T cell antigen; and (b) a second polypeptide comprising, from N-terminus to C-terminus (i) a second Fab that specifically binds a target antigen, (ii) a second immunoglobulin Fc domain, and (iii) a second scFv that specifically binds a T cell antigen, wherein the first and the second immunoglobulin domains associate with one another via disulfide bonding to form the molecule.

In another aspect, the present invention provides a multispecific antigen-binding molecule, comprising: (a) a first polypeptide comprising, from N-terminus to C-terminus (i) a first Fab that specifically binds a T cell antigen, (ii) a first immunoglobulin Fc domain, and (iii) a second Fab that specifically binds a T cell antigen; and (b) a second polypeptide comprising, from N-terminus to C-terminus (i) a second Fab that specifically binds a target antigen, and (ii) a second immunoglobulin Fc domain, wherein the first and the second immunoglobulin domains associate with one another via disulfide bonding to form the molecule.

In various embodiments, such as any of those mentioned above or herein, the T cell antigen is a T cell receptor complex antigen (i.e., any of the protein subunits that make up the T cell receptor complex). In some cases, the T cell antigen is CD3. In some cases, the T cell antigen is a co-stimulatory molecule or a check-point inhibitor on a T cell. In some embodiments, the T cell antigen is selected from the group consisting of CD27, CD28, 4-1BB and PD-1. In some embodiments, the T cell antigen is selected from the group consisting of CD3, CD27, CD28, 4-1BB and PD-1.

In various embodiments, such as any of those mentioned above or herein, the target antigen is a tumor-associated antigen. In some embodiments, the target antigen is a viral or bacterial antigen. In some embodiments, the target antigen is a fungal antigen or a parasite antigen.

In some embodiments, such as any of those mentioned above or herein, the first and second multimerizing domains are immunoglobulin Fc domains. In some cases, the first multimerizing domain and the second multimerizing domain are human IgG1 or human IgG4 Fc domains. In some cases, the first and second multimerizing domains comprise an immunoglobulin hinge domain, a CH2 domain and a CH3 domain of a human IgG polypeptide (e.g., IgG1, IgG2, IgG3 or IgG4). In some cases, the first and second multimerizing domains comprise a hinge domain, a CH2 domain and a CH3 domain of a human IgG1 polypeptide. In some cases, the first and second multimerizing domains comprise a hinge domain, a CH2 domain and a CH3 domain of a human IgG4 polypeptide. In some embodiments, the first and second multimerizing domains associate with one another via disulfide bonding.

In some embodiments, such as any of those mentioned above or herein, the first multimerizing domain or the second multimerizing domain comprises an amino acid substitution that reduces affinity for Protein A binding compared to a wild-type Fc domain of the same isotype. In some cases, the amino acid substitution comprises an H435R modification, or H435R and Y436F modifications (EU numbering). In some cases, the first multimerizing domain comprises the H435R and Y436F modifications. In some cases, the second multimerizing domain comprises the H435R and Y436F modifications. In some embodiments, the first polypeptide, the second polypeptide, or both the first and the second polypeptides comprise a modified hinge domain that reduces binding affinity for an Fcγ receptor relative to a wild-type hinge domain of the same isotype.

In another aspect, the present invention provides a pharmaceutical composition comprising any one of the multispecific molecules discussed above or herein, and a pharmaceutically acceptable carrier or diluent.

In another aspect, the present invention provides a method of treating cancer, comprising administering any one of the multispecific molecules discussed above or herein to a subject in need thereof.

In another aspect, the present invention provides a method of treating an infection, comprising administering any one of the multispecific molecules discussed above or herein to a subject in need thereof. In some cases, the infection is a bacterial infection. In some cases, the infection is a viral infection. In some cases, the infection is a fungal infection. In some cases, the infection is a parasite infection.

In various embodiments, the target antigen is present at a density of from 10 to 10,000,000 copies per target cell. In various embodiments, the target antigen is present at a density of from 100 to 10,000,000 copies per target cell. In various embodiments, the target antigen is present at a density of from 100 to 1,000,000 copies per target cell. In some embodiments, the target antigen is present at a density of from 50 to 10,000. In some embodiments, the target antigen is present at a density of from 100 to 5000. In some embodiments, the target antigen is present at a density of from 100 to 20,000. In some embodiments, the target antigen is present at a density of from 500 to 1,000,000 copies per target cell. In some embodiments, the target antigen is present at a density of from 1000 to 20,000 copies per target cell. In some embodiments, the target antigen is present at a density of greater than 20,000 copies per target cell. In various embodiments, the target antigen is present at a density of about 10, about 50, about 100, about 200, about 300, about 400, about 500, about 1000, about 2000, about 3000, about 4000, about 5000, about 6000, about 7000, about 8000, about 9000, about 10,000, about 15,000, about 20,000, about 25,000, about 50,000, about 75,000, about 100,000, about 200,000, about 300,000, about 400,000, about 500,000, about 600,000, about 700,000, about 800,000, about 900,000, about 1,000,000, about 2,000,000, about 3,000,000, about 4,000,000 or about 5,000,000 copies per target cell. As used herein, a "low density antigen" is an antigen where no more than 5000 copies of the antigen are found on a target cell. References to a low density antigen include cases in which a cell has no more than 4000, no more than 3000, no more than 2000, no more than 1000, no more than 900, no more than 800, no more than 700, no more than 600, no more than 500, no more than 400, no more than 300, no more than 200, no more than 100, or no more than 50 copies of the target antigen.

In various embodiments, the multispecific molecule is administered in combination with a second therapeutic agent to treat a disease or disorder. In some cases, the second therapeutic agent comprises a bispecific antigen-binding molecule comprising a first antigen-binding domain that binds a target antigen (TA) and a second antigen-binding domain that binds a T-cell antigen. In some cases, the target antigen is a tumor-cell antigen. In some embodiments, the second therapeutic agent comprises a bispecific anti-TA× anti-CD28 antibody. In some embodiments, the second therapeutic agent comprises a bispecific anti-EGFR×anti-CD28 antibody. In some embodiments, the second therapeutic agent comprises an antibody that binds a check-point inhibitor on a T cell. In some embodiments, the second therapeutic agent comprises an anti-PD-1 antibody. In some cases, the multispecific molecule is administered in combination with two or more second therapeutic agents.

In another aspect, the present invention provides for use of any one of the multispecific molecules discussed above or herein in the manufacture of a medicament for treating a disease or disorder (e.g., a cancer, or an infection) in a subject in need thereof.

In another aspect, the present invention provides for use of any one of the multispecific molecules discussed above or herein in medicine, or to treat a disease or disorder (e.g., a cancer, or an infection).

In another aspect, the present invention provides a multispecific molecule, as discussed above or herein, for use in medicine, or to treat a disease or disorder (e.g., a cancer, or an infection).

In any of the embodiments discussed above or herein, the target antigen may be a peptide in the context of the groove of a major histocompatibility complex (MHC) protein.

In various embodiments, any of the features or components of embodiments discussed above or herein may be combined, and such combinations are encompassed within the scope of the present disclosure. Any specific value discussed above or herein may be combined with another related value discussed above or herein to recite a range with the values representing the upper and lower ends of the range, and such ranges are encompassed within the scope of the present disclosure.

Other embodiments will become apparent from a review of the ensuing detailed description.

BRIEF DESCRIPTION OF THE DRAWINGS

FIGS. 1A and 1B illustrate known bispecific antibody and antigen-binding molecule formats.

FIGS. 1C, 1E, 1F, 1G, 1H, 1I, 1J, 1K, 1L, 1M, 1N, 1O, 1P, 1Q, 1R and 1S illustrate bispecific or multispecific antigen-binding molecule formats in accordance with embodiments of the present invention. In each of these formats, a first polypeptide chain comprises both an N-terminal and a C-terminal antigen-binding domain (e.g., a Fab or scFv) that specifically binds a T-cell antigen (TCA) (e.g., CD3), and a second polypeptide chain comprising at least one antigen-binding domain (e.g., a Fab or scFv) that binds a target antigen (TA) (e.g., a tumor cell antigen). FIG. 1D illustrates a format in which the two antigen-binding domains that specifically bind a T-cell antigen (e.g., CD3) are located on different polypeptide chains (at the N-terminus on one polypeptide chain, and at the C-terminus on the second polypeptide chain).

As shown in FIGS. 6A, 6B, 6C and 6D, the presence of two active antigen-binding domains improved binding to the target antigens, and similar binding was observed irrespective of the source of the anti-CD3 binding domains. As illustrated in these figures, binding was most affected when the N-terminal Fab domain was removed.

As shown in FIGS. 8A and 8B, C-terminal scFv domains provided superior binding to the target antigens compared to C-terminal Fab domains.

FIGS. 10A and 10B show binding of the molecules having the structures of FIGS. 1C and 1D to A375 cells overexpressing a MAGEA4 peptide (FIG. 10A), or CD3+ Jurkat cells (FIG. 10B). The CD3-binding domains of the molecules comprise the variable regions of a 7221G anti-CD3 antibody. The two molecules showed similar binding to both cell types relative to one another.

FIGS. 12A and 12B show the relative cytotoxic activity and potency of molecules having the structures of FIG. 1C and FIG. 1F, respectively, as compared to a molecule having the structure of FIG. 1A. The molecules were tested individually, and in combination with a co-stimulatory bispecific EGFR×CD28 antibody and an anti-PD-1 antibody, as discussed in Example 7. The CD3-binding domains of the molecules comprise the variable regions of a 7195P anti-CD3 antibody. The molecule having the structure of FIG. 1F targets two different epitopes of the same target antigen with the two TA antigen-binding domains, whereas the molecule having the structure of FIG. 1C targets the same epitope of the target antigen with the two TA antigen-binding domains. The molecule having the structure of FIG. 1F was more potent than the molecule having the structure of FIG. 1C, and both molecules were more potent that the molecule having the structure of FIG. 1A. In each case, the combination of these molecules with the co-stimulatory bispecific antibody and the anti-PD-1 antibody produced even greater cytotoxic potency, similar to the results shown in FIGS. 4A-4C.

FIGS. 16A, 16B and 16C show the relative binding affinity for molecules having the structures of FIGS. 1A (Molecule C), 1C (Molecule B), and IF (Molecules A and D) to NYESO-1-positive cells (FIG. 16A), MAGEA4 (peptide 1)-positive cells (FIG. 16B) and MAGEA4 (peptide 2)-positive cells (FIG. 16C). As expected, Molecule D, without an NYESO-1 binding domain does not bind to the NYESO-1 expressing cells (FIG. 16A), and the molecules that lack the relevant MAGEA4 binding domain do not bind to the MAGEA4-expressing cells, as shown in FIGS. 16B and 16C. The CD3-binding domains of the molecules comprise the variable regions of a 7195P anti-CD3 antibody. The "HLA Targeting Bispecific" positive control binds HLA molecules and CD3. The "Isotype Control Multispecific" is a molecule having the structure of FIG. 1C with binding domains to an irrelevant target antigen.

As shown in FIG. 18A, the molecule having the structure of FIG. 1F (targeting two distinct epitopes of MAGEA4) is more potent than the molecule having the structure of FIG. 1C (targeting a single epitope with both TA-binding domains), and both molecules are more potent than the molecule having the structure of FIG. 1A. Similarly, as shown in FIG. 18B, the molecule having the structure of FIG. 1F (targeting two different antigens) is more potent than the molecule having the structure of FIG. 1C (targeting a single antigen with both TA-binding domains), and both molecules are more potent than the molecule having the structure of FIG. 1A. In each case, the combination of these molecules with the co-stimulatory bispecific antibody and the anti-PD-1 antibody produced even greater cytotoxic potency, relative to the molecule alone, similar to the results shown in FIGS. 4A-4C.

FIGS. 18C, 18D, 18E and 18F show the relative T-cell activation of the molecules discussed in connection with FIGS. 18A and 18B.

As shown in FIGS. 19A and 19B, the molecule having the structure of FIG. 1F more potently kills the tumor cells and increases T-cell activation than does the combination of the two molecules having the structure of FIG. 1A.

DETAILED DESCRIPTION

Figure 2:
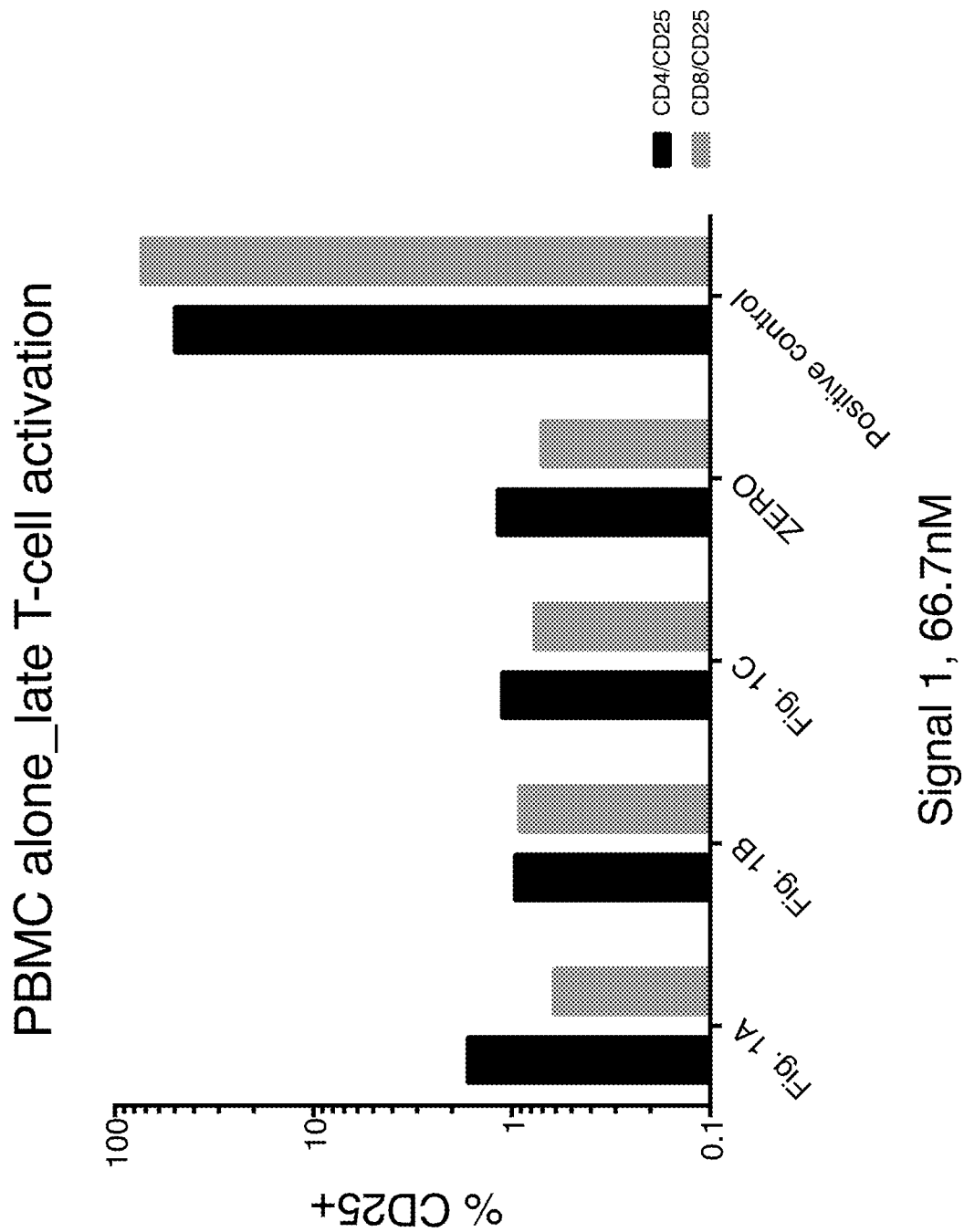
FIG. 2 shows T cell activation induced by molecules having each of the formats illustrated in FIGS. 1A, 1B and 1C compared to a T cell-only control (ZERO) and a positive control. None of the molecules activated T cells in the absence of target cells.

Before the present invention is described in further detail, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present invention, the preferred methods and materials are now described. All patents, applications and non-patent publications mentioned in this specification are incorporated herein by reference in their entireties.

Definitions

The term "T cell" refers to immune cells expressing CD3, including CD4+ cells (helper T cells), CD8+ cells (cytotoxic T cells), regulatory T cells (Tregs), and tumor infiltrating lymphocytes.

The expression "T-cell antigen" refers to a cell-surface expressed protein present on a T cell, and includes "co-stimulatory molecules." A "co-stimulatory molecule" refers to a protein expressed by a T cell that binds a cognate ligand or receptor (e.g., on an antigen-presenting cell) to provide a stimulatory signal, which, in combination with the primary signal provided by engagement of the T cell's TCR with a peptide/MHC, stimulates the activity of the T cell. Stimulation of a T cell can include activation, proliferation and/or survival of the T cell.

As used herein, the expression "cell surface-expressed" or "cell-surface molecule" means one or more protein(s) that is/are expressed on the surface of a cell in vitro or in vivo, such that at least a portion of the protein is exposed to the extracellular side of the cell membrane and is accessible to an antigen-binding portion of an antibody or an antigen-binding domain of the multispecific antigen-binding molecules discussed herein.

The expression "CD3," as used herein, refers to an antigen which is expressed on T cells as part of the multimolecular T cell receptor (TCR) and which consists of a homodimer or heterodimer formed from the association of two of four receptor chains: CD3-epsilon, CD3-delta, CD3-zeta, and CD3-gamma. All references to proteins, polypeptides and protein fragments herein are intended to refer to the human version of the respective protein, polypeptide or protein fragment unless explicitly specified as being from a non-human species. Thus, the expression "CD3" means human CD3 unless specified as being from a non-human species, e.g., "mouse CD3," "monkey CD3," etc.

As used herein, "an antibody that binds CD3" or an "anti-CD3 antibody" includes antibodies and antigen-binding fragments thereof that specifically recognize a single CD3 subunit (e.g., epsilon, delta, gamma or zeta), as well as antibodies and antigen-binding fragments thereof that specifically recognize a dimeric complex of two CD3 subunits (e.g., gamma/epsilon, delta/epsilon, and zeta/zeta CD3 dimers). The antigen-binding domains of the present invention may bind soluble CD3 and/or cell surface expressed CD3. Soluble CD3 includes natural CD3 proteins as well as recombinant CD3 protein variants such as, e.g., monomeric and dimeric CD3 constructs, that lack a transmembrane domain or are otherwise unassociated with a cell membrane.

As used herein, the expression "cell surface-expressed CD3" means one or more CD3 protein(s) that is/are expressed on the surface of a cell in vitro or in vivo, such that at least a portion of a CD3 protein is exposed to the extracellular side of the cell membrane and is accessible to an antigen-binding portion of an antibody. "Cell surface-expressed CD3" includes CD3 proteins contained within the context of a functional T cell receptor in the membrane of a cell. The expression "cell surface-expressed CD3" includes CD3 protein expressed as part of a homodimer or heterodimer on the surface of a cell (e.g., gamma/epsilon, delta/epsilon, and zeta/zeta CD3 dimers). The expression, "cell surface-expressed CD3" also includes a CD3 chain (e.g., CD3-epsilon, CD3-delta or CD3-gamma) that is expressed by itself, without other CD3 chain types, on the surface of a cell. A "cell surface-expressed CD3" can comprise or consist of a CD3 protein expressed on the surface of a cell which normally expresses CD3 protein. Alternatively, "cell surface-expressed CD3" can comprise or consist of CD3 protein expressed on the surface of a cell that normally does not express human CD3 on its surface but has been artificially engineered to express CD3 on its surface.

The term "antigen-binding domain" refers to that portion of a multispecific molecule or a corresponding antibody that binds specifically to a predetermined antigen (e.g., CD3 or a tumor associated antigen). References to a "corresponding antibody" refer to the antibody from which the CDRs or variable regions (HCVR and LCVR) used in a multispecific molecule are derived. For example, the FIG. 1C structured molecules discussed in the examples include Fabs and scFvs with variable regions derived from specific anti-CD3 antibodies and anti-MAGEA4 antibodies. These antibodies are the "corresponding antibodies" to the respective multispecific molecules.

The term "multispecific antigen-binding molecule" includes molecules that bind two or more (e.g., three or four) different epitopes or antigens. In some cases, the multispecific antigen-binding molecules are bispecific. In some cases, the multispecific antigen-binding molecules are trispecific. In some cases, the multispecific antigen-binding molecules are tetraspecific.

The term "antibody" means any antigen-binding molecule or molecular complex comprising at least one complementarity determining region (CDR) that specifically binds to or interacts with a particular antigen (e.g., CD3 or a target antigen (TA)). The term "antibody" includes immunoglobulin molecules comprising four polypeptide chains, two heavy (H) chains and two light (L) chains inter-connected by disulfide bonds, as well as multimers thereof (e.g., IgM). The term "antibody" also includes immunoglobulin molecules consisting of four polypeptide chains, two heavy (H) chains and two light (L) chains inter-connected by disulfide bonds. Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the anti-TA antibody or anti-CD3 antibody (or antigen-binding portion thereof) may be identical to the human germline sequences, or may be naturally or artificially modified. An amino acid consensus sequence may be defined based on a side-by-side analysis of two or more CDRs.

The term "antibody", as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H1$; (ii) $V_H$-$C_H2$; (iii) $V_H$-$C_H3$; (iv) $V_H$-$C_H1$-$C_H2$; (V) $V_H$-$C_H1$-$C_H2$-$C_H3$; $V_H$-$C_H2$-$C_H3$; (Vii) $V_H$-$C_L$; $V_L$-$C_H1$; (iX) $V_L$-$C_H2$; (X) $V_L$-$C_H3$; (Xi) $V_L$-$C_H1$-$C_H2$; (XII) $V_L$-$C_H1$-$C_H2$-$C_H3$; (Xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

In certain embodiments of the invention, the antibodies are human antibodies. The term "human antibody" is intended to include antibodies having variable and constant regions derived from human germline immunoglobulin sequences. The human antibodies may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The antibodies discussed herein may, in some embodiments, be recombinant human antibodies. The term "recombinant human antibody" is intended to include all human antibodies that are prepared, expressed, created or isolated by recombinant means, such as antibodies expressed using a recombinant expression vector transfected into a host cell, antibodies isolated from a recombinant, combinatorial human antibody library, antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

The antibodies referenced herein may be isolated antibodies. An "isolated antibody," as used herein, means an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody." An isolated antibody also includes an antibody in situ within a recombinant cell. Isolated antibodies are antibodies that have been subjected to at least one purification or isolation step. An isolated antibody may be substantially free of other cellular material and/or chemicals.

The antibodies referenced herein may comprise one or more amino acid substitutions, insertions and/or deletions in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

A "multimerization domain" or "multimerizing domain" is any macromolecule that has the ability to associate (covalently or non-covalently) with a second macromolecule of the same or similar structure or constitution. For example, a multimerization domain may be a polypeptide comprising an immunoglobulin $C_H3$ domain. A non-limiting example of a multimerization domain is an Fc portion of an immunoglobulin, e.g., an Fc domain of an IgG selected from the isotypes IgG1, IgG2, IgG3, and IgG4, as well as any allotype within each isotype group. In certain embodiments, the multimerization domain is an Fc fragment or an amino acid sequence of 1 to about 200 amino acids in length containing at least one cysteine residue. In other embodiments, the multimerization domain is a cysteine residue or a short cysteine-containing peptide. Other multimerization domains include peptides or polypeptides comprising or consisting of a leucine zipper, a helix-loop motif, or a coiled-coil motif. In some embodiments, the multimerizing domain is an immunoglobulin Fc domain and the multispecific antigen-binding molecules of the present invention are formed by association of two such Fc domains via interchain disulfide bonding as in a conventional antibody.

The terms "nucleic acid" or "polynucleotide" refers to nucleotides and/or polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Nucleic acids can be either single stranded or double stranded.

The term "recombinant," as used herein, is intended to include all molecules that are prepared, expressed, created or isolated by recombinant means, such as multispecific molecules (e.g. bispecific molecules) expressed using a recombinant expression vector transfected into a host cell, multispecific molecules (e.g., bispecific molecules) isolated from an animal (e.g., a mouse) that is transgenic for human immunoglobulin genes (see e.g., Taylor et al. (1992) Nucl. Acids Res. 20:6287-6295) or multispecific molecules prepared, expressed, created or isolated by any other means that involves splicing of human immunoglobulin and/or MHC gene sequences to other DNA sequences. Such recombinant multispecific molecules can include antigen-binding domains having variable and constant regions derived from human germline immunoglobulin sequences.

The term "subject" or "patient" as used herein includes all members of the animal kingdom including non-human primates and humans. In one embodiment, patients are humans with a disease or disorder, e.g., an infection or a cancer.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 95%, and more preferably at least about 96%, 97%, 98% or 99% of the nucleotide bases, as measured by any well-known algorithm of sequence identity, such as FASTA, BLAST or Gap, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331, herein incorporated by reference. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443-1445, herein incorporated by reference. A "moderately conservative" replacement is any change having a nonnegative value in the PAM250 log-likelihood matrix.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG software contains programs such as Gap and Bestfit which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215:403-410 and Altschul et al. (1997) Nucleic Acids Res. 25:3389-402, each herein incorporated by reference.

The terms "vector" and "expression vector" include, but are not limited to, a viral vector, a plasmid, an RNA vector or a linear or circular DNA or RNA molecule which may consist of chromosomal, non-chromosomal, semi-synthetic or synthetic nucleic acids. In some cases, the vectors are those capable of autonomous replication (episomal vector) and/or expression of nucleic acids to which they are linked (expression vectors). Large numbers of suitable vectors are known to those of skill in the art and are commercially available. Viral vectors include retrovirus, adenovirus, parvovirus (e.g., adenoassociated viruses), coronavirus, negative strand RNA viruses such as orthomyxovirus (e.g., influenza virus), rhabdovirus (e.g., rabies and vesicular stomatitis virus), paramyxovirus (e.g. measles and Sendai), positive strand RNA viruses such as picornavirus and alphavirus, and double-stranded DNA viruses including adenovirus, herpesvirus (e.g., Herpes Simplex virus types 1 and 2, Epstein-Barr virus, cytomegalovirus), and poxvirus (e.g., vaccinia, fowlpox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D type viruses, HTLV-BLV group, and lentivirus.

Multispecific Antigen-Binding Molecules

The multispecific antigen-binding molecules (e.g., bispecific or trispecific or tetraspecific) of the present invention comprise (a) a first polypeptide comprising, from N-terminus to C-terminus (i) a first antigen-binding domain that specifically binds a T cell antigen, (ii) a first multimerizing domain, and (iii) a second antigen-binding domain that specifically binds a T cell antigen; and (b) a second polypeptide comprising, from N-terminus to C-terminus (i) a third antigen-binding domain that specifically binds a target antigen, and (ii) a second multimerizing domain, wherein the first and the second multimerizing domains associate with one another (e.g., via interchain disulfide bonding) to form the molecule.

In some embodiments, the multispecific antigen-binding molecules (e.g., bispecific or trispecific or tetraspecific) of the present invention comprise (a) a first polypeptide comprising, from N-terminus to C-terminus (i) a first antigen-binding domain that specifically binds a T cell antigen, (ii) a first multimerizing domain, and (iii) a second antigen-binding domain that specifically binds a T cell antigen; and (b) a second polypeptide comprising, from N-terminus to C-terminus (i) a third antigen-binding domain that specifically binds a target antigen, (ii) a second multimerizing domain, and (iii) a fourth antigen-binding domain that specifically binds a target antigen, wherein the first and the second multimerizing domains associate with one another (e.g., via interchain disulfide bonding) to form the molecule.

The antigen-binding domains referenced above and herein can be Fab domains, comprising a heavy chain variable region (HCVR) and a heavy chain CH1 domain paired with a light chain variable region (LCVR) and a CL domain. The antigen-binding domains referenced above and herein can also be single chain variable fragment (scFv) domains, comprising a HCVR and LCVR connected together by a short peptide linker of, e.g., from about 10 to about 25 amino acids. Specific linkers include (G4S)$_n$ linkers, wherein n=1-10, or n is 1, 2, 3, 4, 5, 6, 7, 8, 9, or 10 (SEQ ID NOs: 171 to 180, respectively). In some cases, the linker between the HCVR and LCVR of each scFv is (G4S)$_4$ (SEQ ID NO: 174). Unless otherwise defined, the antigen-binding domains of the multispecific molecules of the present invention can be all Fab domains, all scFv domains, or a combination of Fab domains and scFv domains. In some cases, one or more of the antigen-binding domains is a Fab domain. In some cases, one or more of the antigen-binding domains is a scFv domain. In some cases, the first antigen-binding domain and the third antigen-binding domain are Fab domains. In some cases, the second antigen-binding domain is an scFv domain. In some cases, the fourth antigen-binding domain is an scFv domain. In some cases, the first and third antigen-binding domains are Fab domains, and the second and fourth antigen-binding domains are scFv domains. In some cases, the first, second and third antigen-binding domains are Fab domains. In some cases, the first, second, third and fourth antigen-binding domains are Fab domains.

In various embodiments, the scFv domains are connected to the C-terminus of the respective multimerizing domain via a linker peptide. In some cases, the linker is between 1-10 amino acids long. In some embodiments, the linker is between 1-20 amino acids long. In this regard, the linker may be 1, 2, 3, 4, 5, 6, 7, 8, 9, 10, 11, 12, 13, 14, 15, 16, 17, 18, 19 or 20 amino acids long. In some embodiments, the linker may be 21, 22, 23, 24, 25, 26, 27, 28, 29 or 30 amino acids long. Ranges including the numbers discussed herein are also encompassed within this disclosure, e.g., a linker 10-30 amino acids long. In some embodiments, the linkers are flexible linkers. Suitable linkers can be readily selected and can be of any of a suitable of different lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and may be 1, 2, 3, 4, 5, 6, or 7 amino acids. Exemplary flexible linkers include glycine polymers (G)n, glycine-serine polymers (GS)$_n$, where n is an integer of at least one (e.g., from 1-20), glycine-alanine polymers, alanine-serine polymers, and other flexible linkers known in the art. Specific linkers include (G4S)$_n$ linkers, wherein n=1-10, or n is 1, 2, 3, 4, 5, 6, 7, 8, 9, or 10 (SEQ ID NOs: 171 to 180, respectively). In some cases, the linker between each scFv domain and the C-terminus of the respective multimerizing domain is (G4S)3 (SEQ ID NO: 173).

In those embodiments in which one or more antigen-binding domains is an scFv, the scFv can be a stabilized scFv, in which one or more modifications is made to the HCVR and/or LCVR sequence in order to produce and maintain a proper conformation of the scFv. In some embodiments, the scFv includes cysteine mutations at residue 44 of the HCVR and residue 100 of the LCVR (Kabat numbering) to produce inter-disulfide bonding between the variable regions (see, Zhao et al., Int. J. Mol. Sci, 12:1-11, 2011; and Weatherill et al., Protein Engineering, Design and Selection, 25(7):321-329, 2012). In some embodiments, the scFv includes mutations at residue 39 of the HCVR and residue 38 of the LCVR (Kabat numbering) to modify the glutamine residues to glutamic acid or lysine residues to inhibit conformational isomerization (see, Igawa et al., Protein Engineering, Design and Selection, 23(8):667-677, 2010).

In various embodiments, the LCVR (and optionally the CL) of any of the antigen-binding domains can be a cognate LCVR that corresponds to the HCVR, or the LCVR can be a universal LCVR (and optionally CL) common to multiple antigen-binding domains. In some embodiments, the light chain of the Fab domains is a common light chain. In some embodiments, the light chain of the Fab domains is a cognate light chain corresponding to the target antigen binding domain, and the light chain is common to both Fab domains. In some embodiments, the LCVR of the scFv domains is a cognate LCVR. In some embodiments, the light chain of the Fab domains is a common light chain and the LCVR of the scFv domains is a cognate LCVR.

In some embodiments, the multispecific antigen-binding molecules of the present invention comprise: (a) a first polypeptide comprising, from N-terminus to C-terminus (i) a first Fab that specifically binds a T cell antigen, (ii) a first immunoglobulin Fc domain, and (iii) a first scFv that specifically binds a T cell antigen; and (b) a second polypeptide comprising, from N-terminus to C-terminus (i) a second Fab that specifically binds a target antigen, (ii) a second immunoglobulin Fc domain, and (iii) a second scFv that specifically binds a target antigen, wherein the first and the second immunoglobulin domains associate with one another via disulfide bonding to form the molecule. An exemplary structure for such a molecule is illustrated in FIG. 1C.

In some embodiments, the multispecific antigen-binding molecules of the present invention comprise: (a) a first polypeptide comprising, from N-terminus to C-terminus (i) a first Fab that specifically binds a T cell antigen, (ii) a first immunoglobulin Fc domain, and (iii) a second Fab that specifically binds a T cell antigen; and (b) a second polypeptide comprising, from N-terminus to C-terminus (i) a third Fab that specifically binds a target antigen, (ii) a second immunoglobulin Fc domain, and (iii) a fourth Fab that specifically binds a target antigen, wherein the first and the second immunoglobulin domains associate with one another via disulfide bonding to form the molecule. An exemplary structure for such a molecule is illustrated in FIG. 1E.

In some embodiments, the multispecific antigen-binding molecules of the present invention comprise: (a) a first polypeptide comprising, from N-terminus to C-terminus (i) a first Fab that specifically binds a T cell antigen, (ii) a first immunoglobulin Fc domain, and (iii) a first scFv that specifically binds a T cell antigen; and (b) a second polypeptide comprising, from N-terminus to C-terminus (i) a second Fab that specifically binds a first target antigen, (ii) a second immunoglobulin Fc domain, and (iii) a second scFv that specifically binds a second target antigen different from the first target antigen, wherein the first and the second immunoglobulin domains associate with one another via disulfide bonding to form the molecule. An exemplary structure for such a molecule is illustrated in FIG. 1F.

In some embodiments, the multispecific antigen-binding molecules of the present invention comprise: (a) a first polypeptide comprising, from N-terminus to C-terminus (i) a first Fab that specifically binds a T cell antigen, (ii) a first immunoglobulin Fc domain, and (iii) a second Fab that specifically binds a T cell antigen; and (b) a second polypeptide comprising, from N-terminus to C-terminus (i) a third Fab that specifically binds a first target antigen, (ii) a second immunoglobulin Fc domain, and (iii) a fourth Fab that specifically binds a second target antigen different from the first target antigen, wherein the first and the second immunoglobulin domains associate with one another via disulfide bonding to form the molecule. An exemplary structure for such a molecule is illustrated in FIG. 1G.

In some embodiments, the multispecific antigen-binding molecules of the present invention comprise: (a) a first polypeptide comprising, from N-terminus to C-terminus (i) a first Fab that specifically binds a T cell antigen, (ii) a first immunoglobulin Fc domain, and (iii) a first scFv that specifically binds a T cell antigen; and (b) a second polypeptide comprising, from N-terminus to C-terminus (i) a second Fab that specifically binds a target antigen, (ii) a second immunoglobulin Fc domain, and (iii) a second scFv that specifically binds a T cell antigen, wherein the first and the second immunoglobulin domains associate with one another via disulfide bonding to form the molecule. An exemplary structure for such a molecule is illustrated in FIG. 1H.

In some embodiments, the multispecific antigen-binding molecules of the present invention comprise: (a) a first polypeptide comprising, from N-terminus to C-terminus (i) a first Fab that specifically binds a T cell antigen, (ii) a first immunoglobulin Fc domain, and (iii) a second Fab that specifically binds a T cell antigen; and (b) a second polypeptide comprising, from N-terminus to C-terminus (i) a third Fab that specifically binds a target antigen, (ii) a second immunoglobulin Fc domain, and (iii) a fourth Fab that specifically binds a T cell antigen, wherein the first and the second immunoglobulin domains associate with one another via disulfide bonding to form the molecule. An exemplary structure for such a molecule is illustrated in FIG. 1I.

In some embodiments, the multispecific antigen-binding molecules of the present invention comprise: (a) a first polypeptide comprising, from N-terminus to C-terminus (i) a first Fab that specifically binds a T cell antigen, (ii) a first immunoglobulin Fc domain, and (iii) a second Fab that specifically binds a T cell antigen; and (b) a second polypeptide comprising, from N-terminus to C-terminus (i) a second Fab that specifically binds a target antigen, and (ii) a second immunoglobulin Fc domain, wherein the first and the second immunoglobulin domains associate with one another via disulfide bonding to form the molecule. An exemplary structure for such a molecule is illustrated in FIG. 1J.

In some embodiments, the multispecific antigen-binding molecules of the present invention comprise: (a) a first polypeptide comprising, from N-terminus to C-terminus (i) a first Fab that specifically binds a T cell antigen, (ii) a first immunoglobulin Fc domain, and (iii) a second Fab that specifically binds a T cell antigen; and (b) a second polypeptide comprising, from N-terminus to C-terminus (i) a third Fab that specifically binds a target antigen, and (ii) a second immunoglobulin Fc domain, wherein the first and the second immunoglobulin domains associate with one another via disulfide bonding to form the molecule. An exemplary structure for such a molecule is illustrated in FIG. 1K.

In some embodiments, the multispecific antigen-binding molecules of the present invention comprise: (a) a first polypeptide comprising, from N-terminus to C-terminus (i) a first Fab that specifically binds a first T cell antigen, (ii) a first immunoglobulin Fc domain, and (iii) a first scFv that specifically binds a second T cell antigen; and (b) a second polypeptide comprising, from N-terminus to C-terminus (i) a second Fab that specifically binds a target antigen, (ii) a second immunoglobulin Fc domain, and (iii) a second scFv that specifically binds a target antigen, wherein the first and the second immunoglobulin domains associate with one another via disulfide bonding to form the molecule. An exemplary structure for such a molecule is illustrated in FIG. 1L.

In some embodiments, the multispecific antigen-binding molecules of the present invention comprise: (a) a first polypeptide comprising, from N-terminus to C-terminus (i) a first Fab that specifically binds a first T cell antigen, (ii) a first immunoglobulin Fc domain, and (iii) a second Fab that specifically binds a second T cell antigen; and (b) a second polypeptide comprising, from N-terminus to C-terminus (i) a third Fab that specifically binds a target antigen, (ii) a second immunoglobulin Fc domain, and (iii) a fourth Fab that specifically binds a target antigen, wherein the first and the second immunoglobulin domains associate with one another via disulfide bonding to form the molecule. An exemplary structure for such a molecule is illustrated in FIG. 1M.

In some embodiments, the multispecific antigen-binding molecules of the present invention comprise: (a) a first polypeptide comprising, from N-terminus to C-terminus (i) a first Fab that specifically binds a first T cell antigen, (ii) a first immunoglobulin Fc domain, and (iii) a first scFv that specifically binds a second T cell antigen; and (b) a second polypeptide comprising, from N-terminus to C-terminus (i) a second Fab that specifically binds a first target antigen, (ii) a second immunoglobulin Fc domain, and (iii) a second scFv that specifically binds a second target antigen different from the first target antigen, wherein the first and the second immunoglobulin domains associate with one another via disulfide bonding to form the molecule. An exemplary structure for such a molecule is illustrated in FIG. 1N.

In some embodiments, the multispecific antigen-binding molecules of the present invention comprise: (a) a first polypeptide comprising, from N-terminus to C-terminus (i) a first Fab that specifically binds a first T cell antigen, (ii) a first immunoglobulin Fc domain, and (iii) a second Fab that specifically binds a second T cell antigen; and (b) a second polypeptide comprising, from N-terminus to C-terminus (i) a third Fab that specifically binds a first target antigen, (ii) a second immunoglobulin Fc domain, and (iii) a fourth Fab that specifically binds a second target antigen different from the first target antigen, wherein the first and the second immunoglobulin domains associate with one another via disulfide bonding to form the molecule. An exemplary structure for such a molecule is illustrated in FIG. 1O.

In some embodiments, the multispecific antigen-binding molecules of the present invention comprise: (a) a first polypeptide comprising, from N-terminus to C-terminus (i) a first Fab that specifically binds a first T cell antigen, (ii) a first immunoglobulin Fc domain, and (iii) a first scFv that specifically binds a second T cell antigen; and (b) a second polypeptide comprising, from N-terminus to C-terminus (i) a second Fab that specifically binds a target antigen, (ii) a second immunoglobulin Fc domain, and (iii) a second scFv that specifically binds a T cell antigen (optionally may bind the first T cell antigen, the second T cell antigen, or a third T cell antigen), wherein the first and the second immunoglobulin domains associate with one another via disulfide bonding to form the molecule. An exemplary structure for such a molecule is illustrated in FIG. 1P.

In some embodiments, the multispecific antigen-binding molecules of the present invention comprise: (a) a first polypeptide comprising, from N-terminus to C-terminus (i) a first Fab that specifically binds a first T cell antigen, (ii) a first immunoglobulin Fc domain, and (iii) a second Fab that specifically binds a second T cell antigen; and (b) a second polypeptide comprising, from N-terminus to C-terminus (i) a third Fab that specifically binds a target antigen, (ii) a second immunoglobulin Fc domain, and (iii) a fourth Fab that specifically binds a T cell antigen (optionally may bind the first T cell antigen, the second T cell antigen, or a third T cell antigen), wherein the first and the second immunoglobulin domains associate with one another via disulfide bonding to form the molecule. An exemplary structure for such a molecule is illustrated in FIG. 1Q.

In some embodiments, the multispecific antigen-binding molecules of the present invention comprise: (a) a first polypeptide comprising, from N-terminus to C-terminus (i) a first Fab that specifically binds a first T cell antigen, (ii) a first immunoglobulin Fc domain, and (iii) a second Fab that specifically binds a second T cell antigen; and (b) a second polypeptide comprising, from N-terminus to C-terminus (i) a second Fab that specifically binds a target antigen, and (ii) a second immunoglobulin Fc domain, wherein the first and the second immunoglobulin domains associate with one another via disulfide bonding to form the molecule. An exemplary structure for such a molecule is illustrated in FIG. 1R.

In some embodiments, the multispecific antigen-binding molecules of the present invention comprise: (a) a first polypeptide comprising, from N-terminus to C-terminus (i) a first Fab that specifically binds a first T cell antigen, (ii) a first immunoglobulin Fc domain, and (iii) a second Fab that specifically binds a second T cell antigen; and (b) a second polypeptide comprising, from N-terminus to C-terminus (i) a third Fab that specifically binds a target antigen, and (ii) a second immunoglobulin Fc domain, wherein the first and the second immunoglobulin domains associate with one another via disulfide bonding to form the molecule. An exemplary structure for such a molecule is illustrated in FIG. 1S.

Unless otherwise defined, and when present, the fourth antigen-binding domain can specifically bind a target antigen or a T cell antigen. In some cases, the third antigen-binding domain and the fourth antigen-binding domain specifically bind distinct target antigens (different epitopes on the same protein, or different proteins). In some cases, the distinct target antigens are expressed on the surface of the same target cell (e.g., tumor cell). In some cases, the third antigen-binding domain and the fourth antigen-binding domain specifically bind the same target antigen (the same epitope on the same protein). In various embodiments, the first and second antigen-binding domains, and the fourth antigen-binding domain (when present, and directed to a T-cell antigen) can bind the same or distinct T-cell antigens, as illustrated in the figures. In some cases, the first, second and fourth antigen-binding domains specifically bind distinct T-cell antigens (different epitopes on the same protein, or different proteins). In some cases, the first, second and fourth antigen-binding domains specifically bind the same T-cell antigen (the same epitope on the same protein). In some cases, the distinct T-cell antigens are a co-stimulatory molecule (e.g., CD28) and a check-point inhibitor (e.g., PD-1) on the surface of a T cell. In such embodiments, the multispecific molecules of the invention can provide a costimulatory signal to the T cell as well as prevent checkpoint inhibition. As used herein, reference to "same" target antigen or T-cell antigen does not necessarily mean that the antigen-binding domains are binding to the same surface molecule, but rather that the antigen-binding domains have the same specificity (e.g., they each bind CD3 or a TA). Similarly, references to a "distinct" target antigen or T-cell antigen mean that it is different from another target antigen (e.g., MAGEA4 vs. EGFR) or another T-cell antigen (e.g., CD28 vs. PD-1), or is another epitope on the same protein.

In any of the embodiments discussed above or herein, the target antigen can be a tumor-associated antigen or an infection-associated antigen (e.g., a viral antigen, a bacterial antigen, a fungal antigen, or an antigen expressed by a parasite). In some cases, the target antigen is a tumor-associated antigen. In some cases, the target antigen is an infection-associated antigen. In some cases, the target antigen is a viral antigen. In some cases, the target antigen is a bacterial antigen. In some cases, the target antigen is a fungal antigen. In some cases, the target antigen is an antigen expressed by a parasite.

In some cases, the target antigen is a peptide in the context of the groove (PiG) of a major histocompatibility complex (MHC) protein. In some embodiments, the PiG is a peptide consisting of about 5 to about 40 amino acid residues, from about 6 to about 30 amino acid residues, from about 8 to about 20 amino acid residues, or about 9, 10, or 11 amino acid residues. In some cases, the PiG is a fragment of a tumor-associated antigen, a viral antigen, a bacterial antigen, a fungal antigen, or a parasite antigen. In various embodiments, the target antigen is a peptide in the context of the groove of any class, subtype or allele of human leukocyte antigen, including any of HLA-A, HLA-B, HLA-C, HLA-DR, HLA-DQ or HLA-DP. In some embodiments, the target antigen is a peptide/MHC complex. In some cases, the peptide in the peptide/MHC complex is a fragment of a tumor-associated antigen, a fragment of a bacterial antigen, a fragment of a viral antigen, a fragment of a fungal antigen, or a fragment of a parasite antigen.

In some cases, the antigen is a tumor-associated antigen or an antigen expressed by a tumor cell. In some embodiments, the tumor-associated antigen is selected from the group consisting of AFP, ALK, BAGE proteins, BIRC5 (survivin), BIRC7, β-catenin, brc-abl, BRCA1, BORIS, CA9, carbonic anhydrase IX, caspase-8, CALR, CCR5, CD19, CD20 (MS4A1), CD22, CD40, CD70, CDK4, CEA, cyclin-B1, CYP1B1, EGFR, EGFRvIII, ErbB2/Her2, ErbB3, ErbB4, ETV6-AML, EpCAM, EphA2, Fra-1, FOLR1, GAGE proteins (e.g., GAGE-1, -2), GD2, GD3, GloboH, glypican-3, GM3, gp100, Her2, HLA/B-raf, HLA/k-ras, HLA/MAGE-A3, hTERT, IL-10, LMP2, MAGE proteins (e.g., MAGE-1, -2, -3, -4, -6, and -12), MART-1, mesothelin, ML-IAP, Muc1, Muc2, Muc3, Muc4, Muc5, Muc16 (CA-125), MUM1, NA17, NY-BR1, NY-BR62, NY-BR85, NY-ESO1, p15, p53, PAP, PAX3, PAX5, PCTA-1, PLAC1, PRLR, PRAME, PSMA (FOLH1), RAGE proteins, Ras, RGS5, Rho, SART-1, SART-3, STEAP1, STEAP2, TAG-72, TGF-β, TMPRSS2, Thompson-nouvelle antigen (Tn), TRP-1, TRP-2, tyrosinase, and uroplakin-3.

In some cases, the antigen is a viral antigen or a bacterial antigen. In some cases, the viral antigen is associated with or expressed by a virus selected from the group consisting of adenovirus, astrovirus, chikungunya, cytomegalo, dengue, ebola, EBV, hantavirus, HBsAg, hepatitis A, hepatitis B, hepatitis C, hepatitis D, hepatitis E, herpes, HIV, HPIV, HTLV, influenza, Japanese encephalitis virus, lassa, measles, metapneumovirus, mumps, norovirus, oropauche, HPV, parvovirus, rotavirus, RSV, rubella, SARS, TBEV, usutu, vaccina, varicella, West Nile, yellow fever, and zika, or the bacterial antigen is derived from a bacterium selected from the group consisting of methicillin-resistant *Staphylococcus Aureus* (MRSA), *Clostridium Difficile*, carbapenum-resistant Enterobacteriaceae, drug-resistant *Neisseria Gonorrhoeae*, multidrug-resistant *Acinetobacter*, drug-resistant *Campylobacter*, Fluconazole-resistant *Candida*, extended-spectrum β-lactamase producing bacteria, Vancomycin-resistant *enterococcus*, multidrug-resistant *pseudomonas Aeruginosa*, drug-resistant non-typhoidal *Salmonella*, drug-resistant *Salmonella* serotype *typhi*, drug-resistant *Shigella*, drug-resistant *Streptococcus Pneumoniae*, drug-resistant tuberculosis, Vancomycin-resistant *Staphylococcus Aureus*, Erythomycin-resistant group A *Streptococcus*, and Clindamycin-resistant group B *Streptococcus*.

In any of the embodiments discussed above or herein, the T cell antigen can be an antigen expressed at the surface of a T cell, a T cell receptor complex antigen, a co-stimulatory molecule or a check point inhibitor on a T cell, CD3, CD27, CD28, 4-1BB or PD-1. In some cases, the T cell antigen is a T cell receptor complex antigen. In some cases, the T cell antigen is CD3. In some cases, the T cell antigen is a co-stimulatory molecule or a check-point inhibitor on a T cell. In some cases, the T cell antigen is selected from the group consisting of CD27, CD28, 4-1BB and PD-1. In some cases, the T cell antigen is selected from the group consisting of CD3, CD27, CD28, 4-1BB and PD-1. In some cases, the T cell antigen is selected from the group consisting of CD28, ICOS, HVEM, CD27, 4-1BB, 0X40, DR3, GITR, CD30, SLAM, CD2, 2B4, CD226, TIM1, and TIM2.

In certain embodiments in which the T cell antigen is CD3, the CD3-binding domain binds to human CD3 and induces human T cell activation. In certain embodiments, the CD3-binding domain binds weakly to human CD3 and induces human T cell activation. In some embodiments, the CD3-binding domain binds weakly to human CD3 and induces tumor-associated antigen-expressing cell killing. In some embodiments, the CD3-binding domain binds or associates weakly with human and cynomolgus (monkey) CD3, yet the binding interaction is not detectable by in vitro assays known in the art. In some embodiments, the CD3-binding domain binds with weak affinity to human CD3. In some embodiments, the CD3-binding domain binds with moderate affinity to human CD3. In some embodiments, the CD3-binding domain binds with high affinity to human CD3. In some embodiments, the CD3-binding domain binds to human CD3 (e.g., at 25° C.) with a $K_D$ of less than about 15 nM as measured by surface plasmon resonance (e.g., mAb-capture or antigen-capture format) or a substantially similar assay. In some embodiments, the CD3-binding domain binds human CD3 with an $K_D$ value of greater than about 15 nM, greater than about 20 nM, greater than about 30 nM, greater than about 40 nM, greater than about 50 nM, greater than about 60 nM, greater than about 100 nM, greater than about 200 nM, or greater than about 300 nM, as measured in a surface plasmon resonance binding assay (e.g., mAb-capture or antigen-capture format) or a substantially similar assay. In some embodiments, the antibodies or antigen-binding fragments of the present invention bind CD3 with a $K_D$ of less than about 5 nM, less than about 2 nM, less than about 1 nM, less than about 800 pM, less than about 600 pM, less than about 500 pM, less than about 400 pM, less than about 300 pM, less than about 200 pM, less than about 180 pM, less than about 160 pM, less than about 140 pM, less than about 120 pM, less than about 100 pM, less than about 80 pM, less than about 60 pM, less than about 40 pM, less than about 20 pM, or less than about 10 pM, as measured by surface plasmon resonance, e.g., using an assay format as defined in Example 3 herein (e.g., mAb-capture or antigen-capture format), or a substantially similar assay.

In some embodiments, the CD3-binding domain exhibits an $EC_{50}$ value of less than less than about 50 nM, less than about 40 nM, less than about 30 nM, less than about 20 nM, less than about 10 nM, less than about 5 nM, less than about 4 nM, less than about 3 nM, less than about 2 nM, less than about 1 nM, less than 900 pM, less than 800 pM, less than 700 pM, less than 600 pM, or less than 500 pM, as measured in an in vitro flow cytometry binding assay. In some embodiments, the CD3-binding domain exhibits an $EC_{50}$ value of about or greater than about 1 nM, 2 nM, 3 nM, 4 nM, 5 nM, 10 nM, 25 nM, 50 nM, 100 nM, 500 nM or 1 pM, as measured in an in vitro flow cytometry binding assay.

In any of the embodiments, the CD3-binding domain can comprise any of the HCVR/LCVR or CDR (e.g., the six CDRs contained within a pair of HCVR/LCVR sequences) amino acid sequences of the anti-CD3 antibodies disclosed in WO 2014/047231 (9250-WO) or WO 2017/053856 (10151WO01), including the antibodies identified as 7195P, 7221G, 7221G5 and 7221G20. In various embodiments, an anti-CD3 antibody identified as a "strong binder" has an affinity for human CD3 in the single digit nanomolar range (e.g., from 1-9 nM) as measured in a surface plasmon resonance assay (e.g., at 25° C. in an antigen-capture format with measurements conducted on a T200 BIACORE instrument). In various embodiments, an anti-CD3 antibody identified as a "moderate binder" has an affinity for human CD3 in the double digit nanomolar range (e.g., from 10-99 nM, optionally from 10-50 nM or 10-25 nM) as measured in a surface plasmon resonance assay. In various embodiments, an anti-CD3 antibody identified as a "weak binder" has an affinity for human CD3 in the three digit nanomolar range (e.g., from 100-999 nM, optionally from 100-500 nM or from 500 nM to 1 μM) as measured in a surface plasmon resonance assay. In various embodiments, an anti-CD3 antibody identified as a "very weak binder" has an affinity for human CD3 that is greater than 10 μM or is undetectable as measured in a surface plasmon resonance assay.

In any of the embodiments, the CD3-binding domain can comprise any of the HCVR/LCVR or CDR (e.g., the six CDRs contained within a pair of HCVR/LCVR sequences) amino acid sequences set forth in the following tables (the "G" versions are taken from WO 2017/053856) In some embodiments, the CD3-binding domains (e.g., in the Fab arm of a molecule having the structure of FIG. 1C or 1F) comprise a cognate light chain corresponding to the target antigen binding domain. In other words, the cognate light chain of the target antigen binding domain is common to both the target antigen-binding domain and the CD3-binding domain (e.g., in the N-terminal Fab domains of the structure of FIG. 1C or 1F).

TABLE 1

Heavy Chain Amino Acid Sequence Identifiers

| Antibody CD3-VH | SEQ ID NOs: | | | |
|---|---|---|---|---|
| Designation | HCVR | CDR1 | CDR2 | CDR3 |
| CD3-VH-G | 2 | 4 | 6 | 8 |
| CD3-VH-G2 | 10 | 12 | 14 | 16 |
| CD3-VH-G3 | 18 | 20 | 22 | 24 |
| CD3-VH-G4 | 26 | 28 | 30 | 32 |
| CD3-VH-G5 | 34 | 36 | 38 | 40 |
| CD3-VH-G8 | 42 | 44 | 46 | 48 |
| CD3-VH-G9 | 50 | 52 | 54 | 56 |
| CD3-VH-G10 | 58 | 60 | 62 | 64 |
| CD3-VH-G11 | 66 | 68 | 70 | 72 |

TABLE 1-continued

Heavy Chain Amino Acid Sequence Identifiers

| Antibody CD3-VH | SEQ ID NOs: | | | |
|---|---|---|---|---|
| Designation | HCVR | CDR1 | CDR2 | CDR3 |
| CD3-VH-G12 | 74 | 76 | 78 | 80 |
| CD3-VH-G13 | 82 | 84 | 86 | 88 |
| CD3-VH-G14 | 90 | 92 | 94 | 96 |
| CD3-VH-G15 | 98 | 100 | 102 | 104 |
| CD3-VH-G16 | 106 | 108 | 110 | 112 |
| CD3-VH-G17 | 114 | 116 | 118 | 120 |
| CD3-VH-G18 | 122 | 124 | 126 | 128 |
| CD3-VH-G19 | 130 | 132 | 134 | 136 |
| CD3-VH-G20 | 138 | 140 | 142 | 144 |
| CD3-VH-G21 | 146 | 148 | 150 | 152 |
| 7195P | 154 | 156 | 158 | 160 |

TABLE 2

Heavy Chain Nucleic Acid Sequence Identifiers

| Antibody CD3-VH | SEQ ID NOs: | | | |
|---|---|---|---|---|
| Designation | HCVR | CDR1 | CDR2 | CDR3 |
| CD3-VH-G | 1 | 3 | 5 | 7 |
| CD3-VH-G2 | 9 | 11 | 13 | 15 |
| CD3-VH-G3 | 17 | 19 | 21 | 23 |
| CD3-VH-G4 | 25 | 27 | 29 | 31 |
| CD3-VH-G5 | 33 | 35 | 37 | 39 |
| CD3-VH-G8 | 41 | 43 | 45 | 47 |
| CD3-VH-G9 | 49 | 51 | 53 | 55 |
| CD3-VH-G10 | 57 | 59 | 61 | 63 |
| CD3-VH-G11 | 65 | 67 | 69 | 71 |
| CD3-VH-G12 | 73 | 75 | 77 | 79 |
| CD3-VH-G13 | 81 | 83 | 85 | 87 |
| CD3-VH-G14 | 89 | 91 | 93 | 95 |
| CD3-VH-G15 | 97 | 99 | 101 | 103 |
| CD3-VH-G16 | 105 | 107 | 109 | 111 |
| CD3-VH-G17 | 113 | 115 | 117 | 119 |
| CD3-VH-G18 | 121 | 123 | 125 | 127 |
| CD3-VH-G19 | 129 | 131 | 133 | 135 |
| CD3-VH-G20 | 137 | 139 | 141 | 143 |
| CD3-VH-G21 | 145 | 147 | 149 | 151 |
| 7195P | 153 | 155 | 157 | 159 |

TABLE 3

Light Chain Amino Acid Sequence Identifiers

| Antibody ULC | SEQ ID NOs: | | | |
|---|---|---|---|---|
| Designation | LCVR | CDR1 | CDR2 | CDR3 |
| Vκ1-39JK5 | 162 | 164 | 166 | 168 |

TABLE 4

Light Chain Nucleic Acid Sequence Identifiers

| Antibody ULC | SEQ ID NOs: | | | |
|---|---|---|---|---|
| Designation | LCVR | CDR1 | CDR2 | CDR3 |
| Vκ1-39JK5 | 161 | 163 | 165 | 167 |

Each of the antibodies set forth in Table 1 comprises a common light chain variable region comprising the amino acid sequence set forth in Table 3. Each of the "G" designated antibodies may also be referred to herein with a "7221" prefix, e.g., 7221G, 7221G5, 7221G20, etc. In the scFv versions of the antigen-binding domains, the amino acid residue at position 44 of the heavy chain variable region may be replaced with a cysteine residue, for example, as shown in SEQ ID NO: 169 (the modified heavy chain corresponding to 7195P) or SEQ ID NO: 170 (the modified heavy chain corresponding to 7221G).

The multispecific antigen-binding molecules (e.g., bispecific or trispecific or tetraspecific) of the present invention comprise two polypeptide chains, each of which includes a multimerizing domain that facilitates association of the two polypeptide chains (e.g., via interchain disulfide bonding) to form a single multispecific antigen-binding molecule. In any of the embodiments discussed above or herein, the first and second multimerizing domains can be immunoglobulin Fc domains (e.g. of human IgG isotype). In some cases, the first and second multimerizing domains associate with one another via disulfide bonding. In some embodiments, the first multimerizing domain and the second multimerizing domain are human IgG1 or human IgG4 Fc domains. In some cases, the first and second multimerizing domains comprise a hinge domain, a CH2 domain and a CH3 domain of human IgG1 or human IgG4.

In some embodiments, the first multimerizing domain or the second multimerizing domain comprises an amino acid substitution that reduces affinity for Protein A binding compared to a wild-type Fc domain of the same isotype (e.g., human IgG1 or human IgG4). In some cases, the amino acid substitution comprises an H435R modification, or H435R and Y436F modifications (EU numbering). In some cases, the first multimerizing domain comprises the H435R and Y436F modifications. In some cases, the second multimerizing domain comprises the H435R and Y436F modifications.

In some embodiments, the first polypeptide, the second polypeptide, or both the first and the second polypeptides comprise a modified hinge domain that reduces binding affinity for an Fcγ receptor relative to a wild-type hinge domain of the same isotype (e.g., human IgG1 or human IgG4).

In various embodiments in which the multimerizing domain comprises a heavy chain constant region including a hinge domain, the constant region may be chimeric, combining sequences derived from more than one immunoglobulin isotype. For example, a chimeric Fc domain can comprise part or all of a $C_H2$ sequence derived from a human IgG1, human IgG2 or human IgG4 $C_H2$ region, and part or all of a $C_H3$ sequence derived from a human IgG1, human IgG2 or human IgG4. A chimeric Fc domain can also contain a chimeric hinge region. For example, a chimeric hinge may comprise an "upper hinge" sequence, derived from a human IgG1, a human IgG2 or a human IgG4 hinge region, combined with a "lower hinge" sequence, derived from a human IgG1, a human IgG2 or a human IgG4 hinge region. A particular example of a chimeric Fc domain that can be included in any of the antigen-binding molecules set forth herein comprises, from N- to C-terminus: [IgG4 $C_H1$]-[IgG4 upper hinge]-[IgG2 lower hinge]-[IgG4 CH2]-[IgG4 CH3]. Another example of a chimeric Fc domain that can be included in any of the antigen-binding molecules set forth herein comprises, from N- to C-terminus: [IgG1 $C_H1$]-[IgG1 upper hinge]-[IgG2 lower hinge]-[IgG4 CH2]-[IgG1 CH3]. These and other examples of chimeric Fc domains that can be included in any of the antigen-binding molecules of the present invention are described in WO 2014/121087 (8550-WO). Chimeric Fc domains having these general structural arrangements, and variants thereof, can have altered Fc receptor binding, which in turn affects Fc effector function.

In various embodiments in which the multimerizing domain comprises a heavy chain constant region including a hinge domain, positions 233-236 within the hinge domain may be G, G, G and unoccupied; G, G, unoccupied, and unoccupied; G, unoccupied, unoccupied, and unoccupied; or all unoccupied, with positions numbered by EU numbering. Optionally, the heavy chain constant region comprises from N-terminal to C-terminal the hinge domain, a CH2 domain and a CH3 domain. Optionally, the heavy chain constant region comprises from N-terminal to C-terminal a CH1 domain, the hinge domain, a CH2 domain and a CH3 domain. Optionally, the CH1 region, if present, remainder of the hinge region, if any, CH2 region and CH3 region are the same human isotype. Optionally, the CH1 region, if present, remainder of the hinge region, if any, CH2 region and CH3 region are human IgG1. Optionally, the CH1 region, if present, remainder of the hinge region, if any, CH2 region and CH3 region are human IgG2. Optionally, the CH1 region if present, remainder of the hinge region, if any, CH2 region and CH3 region are human IgG4. Optionally, the constant region has a CH3 domain modified to reduce binding to protein A. These and other examples of multimerizing heavy chain constant regions that can be included in any of the antigen-binding molecules of the present invention are described in WO 2016/161010 (10140WO01).

In embodiments of the present invention, the association of one multimerizing domain with another multimerizing domain facilitates the association between the two antigen-binding domains, thereby forming a multispecific antigen-binding molecule. The multimerizing domain may be any macromolecule, protein, polypeptide, peptide, or amino acid that has the ability to associate with a second multimerizing domain of the same or similar structure or constitution. For example, a multimerizing domain may be a polypeptide comprising an immunoglobulin $C_H3$ domain. A non-limiting example of a multimerizing component is an Fc portion of an immunoglobulin (comprising a CH2-CH3 domain), e.g., an Fc domain of an IgG selected from the isotypes IgG1, IgG2, IgG3, and IgG4, as well as any allotype within each isotype group.

In some embodiments, the first and second multimerizing domains may be of the same IgG isotype such as, e.g., IgG1/IgG1, IgG2/IgG2, IgG4/IgG4. Alternatively, the first and second multimerizing domains may be of different IgG isotypes such as, e.g., IgG1/IgG2, IgG1/IgG4, IgG2/IgG4, etc.

In certain embodiments, the multimerizing domain is an Fc fragment or an amino acid sequence of from 1 to about 200 amino acids in length containing at least one cysteine residue. In other embodiments, the multimerizing domain is a cysteine residue, or a short cysteine-containing peptide. Other multimerizing domains include peptides or polypeptides comprising or consisting of a leucine zipper, a helix-loop motif, or a coiled-coil motif.

The multimerizing domains, e.g., Fc domains (with or without a hinge), may comprise one or more amino acid changes (e.g., insertions, deletions or substitutions) as compared to the wild-type, naturally occurring version of the Fc domain. For example, the invention includes bispecific antigen-binding molecules comprising one or more modifications in the Fc domain that results in a modified Fc domain having a modified binding interaction (e.g., enhanced or diminished) between Fc and FcRn. In one embodiment, the bispecific antigen-binding molecule comprises a modification in a $C_H2$ or a $C_H3$ region, wherein the modification increases the affinity of the Fc domain to FcRn in an acidic environment (e.g., in an endosome where pH ranges from about 5.5 to about 6.0). Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., L/R/S/P/Q or K) and/or 434 (e.g., H/F or Y); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P).

The present invention also includes multispecific antigen-binding molecules comprising a first Ig $C_H3$ domain and a second Ig $C_H3$ domain, wherein the first and second Ig $C_H3$ domains differ from one another by at least one amino acid, and wherein at least one amino acid difference reduces binding of the bispecific antibody to Protein A as compared to a bi-specific antibody lacking the amino acid difference. In one embodiment, the first Ig $C_H3$ domain binds Protein A and the second Ig $C_H3$ domain contains a mutation that reduces or abolishes Protein A binding such as an H95R modification (by IMGT exon numbering; H435R by EU numbering). The second $C_H3$ may further comprise a Y96F modification (by IMGT; Y436F by EU). See, for example, U.S. Pat. No. 8,586,713. Further modifications that may be found within the second $C_H3$ include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies.

Preparation of Antigen-Binding Domains and Construction of Bispecific Molecules

Antigen-binding domains specific for particular antigens can be prepared by any antibody generating technology known in the art. Once obtained, different antigen-binding domains, specific for two or more different antigens (e.g., CD3 and a target antigen), can be appropriately arranged relative to one another to produce the structures of the multispecific antigen-binding molecules of the present invention using routine methods. In certain embodiments, one or more of the individual components (e.g., heavy and light chains or parts thereof) of the multispecific antigen-binding molecules of the invention are derived from chimeric, humanized or fully human antibodies. Methods for making such antibodies are well known in the art. For example, one or more of the heavy and/or light chains of the multispecific antigen-binding molecules of the present invention can be prepared using VELOCIMMUNE™ technology. Using VELOCIMMUNE™ technology (or any other human antibody generating technology), high affinity chimeric antibodies to a particular antigen (e.g., CD3 or a target antigen) are initially isolated having a human variable region and a mouse constant region. The antibodies are characterized and selected for desirable characteristics, including affinity, selectivity, epitope, etc. The mouse constant regions are replaced with a desired human constant region to generate fully human heavy and/or light chains that can be incorporated into the multispecific antigen-binding molecules of the present invention.

Genetically engineered animals may be used to make human multispecific antigen-binding molecules. For example, a genetically modified mouse can be used which is incapable of rearranging and expressing an endogenous mouse immunoglobulin light chain variable sequence, wherein the mouse expresses only one or two human light chain variable domains encoded by human immunoglobulin sequences operably linked to the mouse kappa constant gene at the endogenous mouse kappa locus. Such genetically modified mice can be used to produce fully human multispecific antigen-binding molecules comprising two different heavy chains that associate with an identical light chain that comprises a variable domain derived from one of two different human light chain variable region gene segments. (See, e.g., US 2011/0195454). Fully human refers to an antibody, or antigen-binding fragment or immunoglobulin domain thereof, comprising an amino acid sequence encoded by a DNA derived from a human sequence over the entire length of each polypeptide of the antibody or antigen-binding fragment or immunoglobulin domain thereof. In some instances, the fully human sequence is derived from a protein endogenous to a human. In other instances, the fully human protein or protein sequence comprises a chimeric sequence wherein each component sequence is derived from human sequence. While not being bound by any one theory, chimeric proteins or chimeric sequences are generally designed to minimize the creation of immunogenic epitopes in the junctions of component sequences, e.g. compared to any wild-type human immunoglobulin regions or domains.

In various embodiments, the methods and techniques discussed above are used to generate antibodies to a T-cell antigen and a target antigen, and the antigen-binding domains of these antibodies (e.g., the HCVR, LCVR, or CDRs) are used to produce the multispecific antigen-binding molecules as discussed herein or having, e.g., the structures illustrated in FIGS. 1C and 1E-1S.

Binding Properties of the Antigen-Binding Domains

As used herein, the term "binding" in the context of the binding of an antibody (e.g. a corresponding antibody), immunoglobulin, antigen-binding domain or multispecific antigen-binding molecule to, e.g., a predetermined antigen, such as a cell surface protein or fragment thereof, typically refers to an interaction or association between a minimum of two entities or molecular structures, such as an antigen-binding domain/antigen interaction.

For instance, binding affinity typically corresponds to a $K_D$ value of about $10^{-7}$ M or less, such as about $10^{-8}$ M or less, such as about $10^{-9}$ M or less when determined by, for instance, surface plasmon resonance (SPR) technology in a BIAcore 3000 instrument using the antigen as the ligand and the antibody, Ig, antibody-binding domain or multispecific antigen-binding molecule as the analyte (or anti-ligand). Flow cytometry assays are also routinely used.

Accordingly, the antibody (e.g., a corresponding antibody), antigen-binding domain or multispecific antigen-binding molecule of the invention binds to the predetermined antigen or cell surface molecule having an affinity corresponding to a $K_D$ value that is at least ten-fold lower than its affinity for binding to a non-specific antigen (e.g., BSA, casein). According to the present invention, the affinity of an antibody (e.g., a corresponding antibody), antigen-binding domain or multispecific antigen-binding molecule corresponding to a $K_D$ value that is equal to or less than ten-fold lower than a non-specific antigen may be considered non-detectable binding, however such an antibody may be paired with a second antigen binding arm for the production of a bispecific antibody of the invention.

The term "$K_D$" (M) refers to the dissociation equilibrium constant of a particular antibody (or antigen-binding domain)-antigen interaction, or the dissociation equilibrium constant of an antibody (or antigen-binding domain) or antibody-binding fragment binding to an antigen. There is an inverse relationship between $K_D$ and binding affinity, therefore the smaller the $K_D$ value, the higher, i.e. stronger, the affinity. Thus, the terms "higher affinity" or "stronger affinity" relate to a higher ability to form an interaction and therefore a smaller $K_D$ value, and conversely the terms "lower affinity" or "weaker affinity" relate to a lower ability to form an interaction and therefore a larger $K_D$ value. In some circumstances, a higher binding affinity (or $K_D$) of a particular molecule (e.g. antibody or antigen-binding domain) to its interactive partner molecule (e.g. antigen X) compared to the binding affinity of the molecule (e.g. antibody or antigen-binding domain) to another interactive partner molecule (e.g. antigen Y) may be expressed as a binding ratio determined by dividing the larger $K_D$ value (lower, or weaker, affinity) by the smaller $K_D$ (higher, or stronger, affinity), for example expressed as 5-fold or 10-fold greater binding affinity, as the case may be.

The term "$k_d$" (sec−1 or 1/s) refers to the dissociation rate constant of a particular antibody (or antigen-binding domain)-antigen interaction, or the dissociation rate constant of an antibody or antibody-binding domain. Said value is also referred to as the $k_{off}$ value.

The term "$k_a$" (M−1×sec−1 or 1/M) refers to the association rate constant of a particular antibody (or antigen-binding domain)-antigen interaction, or the association rate constant of an antibody or antibody-binding domain.

The term "$K_A$" (M−1 or 1/M) refers to the association equilibrium constant of a particular antibody (or antigen-binding domain)-antigen interaction, or the association equilibrium constant of an antibody or antibody-binding domain. The association equilibrium constant is obtained by dividing the $k_a$ by the $k_d$.

The term "EC50" or "$EC_{50}$" refers to the half maximal effective concentration, which includes the concentration of an antibody (or antigen-binding domain or multispecific molecule) which induces a response halfway between the baseline and maximum after a specified exposure time. The $EC_{50}$ essentially represents the concentration of an antibody (or antigen-binding domain or multispecific molecule) where 50% of its maximal effect is observed. In certain embodiments, the $EC_{50}$ value equals the concentration of a multispecific molecule of the invention that gives half-maximal binding to cells expressing CD3 or target antigen (e.g., tumor-associated antigen), as determined by e.g. a flow cytometry binding assay. Thus, reduced or weaker binding is observed with an increased $EC_{50}$, or half maximal effective concentration value.

In one embodiment, decreased binding can be defined as an increased $EC_{50}$ molecule concentration which enables binding to the half-maximal amount of target cells.

In another embodiment, the $EC_{50}$ value represents the concentration of a molecule of the invention that elicits half-maximal depletion of target cells by T cell cytotoxic activity. Thus, increased cytotoxic activity (e.g. T cell-mediated tumor cell killing) is observed with a decreased $EC_{50}$, or half maximal effective concentration value.

pH-Dependent Binding

The present invention includes antigen-binding domains and multispecific antigen-binding molecules with pH-dependent binding characteristics. For example, a molecule of the present invention may exhibit reduced binding to a T-cell antigen or a target antigen at acidic pH as compared to neutral pH. Alternatively, molecules of the invention may exhibit enhanced binding to a T-cell antigen or a target antigen at acidic pH as compared to neutral pH. The expression "acidic pH" includes pH values less than about 6.2, e.g., about 6.0, 5.95, 5.9, 5.85, 5.8, 5.75, 5.7, 5.65, 5.6, 5.55, 5.5, 5.45, 5.4, 5.35, 5.3, 5.25, 5.2, 5.15, 5.1, 5.05, 5.0, or less. As used herein, the expression "neutral pH" means a pH of about 7.0 to about 7.4. The expression "neutral pH" includes pH values of about 7.0, 7.05, 7.1, 7.15, 7.2, 7.25, 7.3, 7.35, and 7.4.

In certain instances, "reduced binding . . . at acidic pH as compared to neutral pH" is expressed in terms of a ratio of the $K_D$ value of the molecule (or antigen-binding domain) binding to its antigen at acidic pH to the $K_D$ value of the molecule (or antigen-binding domain) binding to its antigen at neutral pH (or vice versa). For example, a molecule or antigen-binding domain may be regarded as exhibiting "reduced binding to a T-cell antigen or a target antigen at acidic pH as compared to neutral pH" for purposes of the present invention if the molecule or antigen-binding domain exhibits an acidic/neutral $K_D$ ratio of about 3.0 or greater. In certain exemplary embodiments, the acidic/neutral $K_D$ ratio for a molecule or antigen-binding domain of the present invention can be about 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 20.0. 25.0, 30.0, 40.0, 50.0, 60.0, 70.0, 100.0 or greater.

Multispecific molecules with pH-dependent binding characteristics may be obtained, e.g., by screening a population of corresponding antibodies for reduced (or enhanced) binding to a particular antigen at acidic pH as compared to neutral pH. Additionally, modifications of the antigen-binding domain at the amino acid level may yield molecules with pH-dependent characteristics. For example, by substituting one or more amino acids of an antigen-binding domain (e.g., within a CDR) with a histidine residue, a molecule with reduced antigen-binding at acidic pH relative to neutral pH may be obtained.

Biological Characteristics of the Multispecific Antigen-Binding Molecules

The present invention can include multispecific antigen-binding molecules and antigen-binding domains thereof that are capable of simultaneously binding to a human T-cell antigen (e.g., CD3) and a human target antigen or antigens (e.g., a tumor-associated antigen).

The present invention can include multispecific antigen-binding molecules that bind a human T-cell antigen (e.g., CD3) and induce T cell activation in the presence of target cells. For example, in some embodiments, the present invention includes multispecific antigen-binding molecules that bind a human T-cell antigen (e.g., CD3) and induce T cell cytotoxic activity in the presence of cells expressing the target antigen or target antigens (e.g., a tumor-associated antigen).

The present invention can include multispecific antigen-binding molecules that bind a human T-cell antigen (e.g., CD3) and induce T cell activation without increasing cytokine production relative to a conventionally structured bispecific anti-CD3×anti-TA antibody (e.g., FIG. 1A).

The present invention can include multispecific antigen-binding molecules that are capable of depleting or reducing cell populations in which the cells express the target antigen or target antigens. The multispecific antigen-binding molecules of the present invention are capable of inducing T-cell mediated cytotoxicity more potently than molecules having conventional bispecific antibody formats (e.g., FIGS. 1A and 1B).

The present invention can include multispecific antigen-binding molecules that bind a human T-cell antigen (e.g., CD3) and two distinct target antigens (e.g., a molecule having the structure of FIG. 1F), and induce cytotoxic activity and/or T-cell activation in the presence of cells expressing the two target antigens.

Many cancers express a variety of intracellular antigens that are processed inside the cell by the proteosome and associated peptides are presented at the surface of the cell in the context of HLA molecules. Targeting peptides from different proteins may be used to increase the specificity of the multispecific molecules of the present invention. In some cases, cancers characterized by PiG antigens or low density cancer antigens escape conventional cancer therapies because they are often present in low target copy numbers within tumors. Additionally, solid tumors characterized by PiGs or low density cancer antigens can be more resistant to therapy and more difficult to treat because they are not cell surface antigens, but are present in grooves within the cancer related peptide. Thus, use of a multispecific molecule of the present invention targeting two distinct antigens (e.g., low density antigens) can effectively target PiGs and/or low density cancer antigens to increase/enhance efficacy of therapy in cancers, especially those cancers characterized by solid tumors.

In various embodiments, the multispecific antigen-binding molecules of the present invention are capable of inducing T-cell mediated cytotoxicity in cell populations when the density of the target antigen ranges from about 100 copies per cell to about 1 million copies per cell or more. In some cases, the target antigen is present at a copy number/cell of about 100, about 200, about 300, about 400, about 500, about 1000, about 2000, about 3000, about 4000, about 5000, about 6000, about 7000, about 8000, about 9000, about 10000, about 15000, about 20000, about 25000, about 30000, about 35000, about 40000, about 45000, about 50000, about 75000, about 100000 (i.e., 100K), about 200K, about 300K, about 400K, about 500K, about 600K, about 700K, about 800K, about 900K, about 1 million, about 2 million, about 3 million, about 4 million, about 5 million, or about 10 million.

Without intending to be bound by theory, the inventors postulate that the improved cytotoxic potency of the molecular format of the present invention is a function of the presence of two T-cell antigen (e.g., CD3) binding domains on a single chain of the molecule. In particular, it is hypothesized that the geometry of the molecular structures of the present invention selectively induces lytic synapse formation at low concentrations without inducing stimulatory synapse formation, the latter of which is responsible for cytokine production from cytotoxic T lymphocytes.

Epitope Mapping and Related Technologies

The epitope on the T-cell antigen (e.g., CD3) and/or the target antigen (e.g., a tumor-associated antigen) to which the antigen-binding molecules of the present invention bind may consist of a single contiguous sequence of 3 or more (e.g., 3, 4, 5, 6, 7, 8, 9, 10, 11, 12, 13, 14, 15, 16, 17, 18, 19, 20 or more) amino acids of a protein. Alternatively, the epitope may consist of a plurality of non-contiguous amino acids (or amino acid sequences) of the protein. The molecules of the invention may interact with, e.g., amino acids contained within a single CD3 chain (e.g., CD3-epsilon, CD3-delta or CD3-gamma), or may interact with amino acids on two or more different CD3 chains. The term "epitope," as used herein, refers to an antigenic determinant that interacts with a specific antigen binding site in the variable region of an antigen-binding domain known as a paratope. A single antigen may have more than one epitope. Thus, different antigen-binding domains may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstances, an epitope may include moieties of saccharides, phosphoryl groups, or sulfonyl groups on the antigen.

Various techniques known to persons of ordinary skill in the art can be used to determine whether an antigen-binding domain of a molecule "interacts with one or more amino acids" within a polypeptide or protein. Exemplary techniques include, e.g., routine cross-blocking assay such as that described Antibodies, Harlow and Lane (Cold Spring Harbor Press, Cold Spring Harb., NY), alanine scanning mutational analysis, peptide blots analysis (Reineke, 2004, Methods Mol Biol 248:443-463), and peptide cleavage analysis. In addition, methods such as epitope excision, epitope extraction and chemical modification of antigens can be employed (Tomer, 2000, Protein Science 9:487-496). Another method that can be used to identify the amino acids within a polypeptide with which an antigen-binding domain of a molecule interacts is hydrogen/deuterium exchange detected by mass spectrometry. In general terms, the hydrogen/deuterium exchange method involves deuterium-labeling the protein of interest, followed by binding the molecule to the deuterium-labeled protein. Next, the protein/molecule complex is transferred to water to allow hydrogen-deuterium exchange to occur at all residues except for the residues protected by the molecule (which remain deuterium-labeled). After dissociation of the molecule, the target protein is subjected to protease cleavage and mass spectrometry analysis, thereby revealing the deuterium-labeled residues which correspond to the specific amino acids with which the molecule interacts. See, e.g., Ehring (1999) Analytical Biochemistry 267(2):252-259; Engen and Smith (2001) Anal. Chem. 73:256A-265A. X-ray crystallography of the antigen/molecule complex may also be used for epitope mapping purposes.

Bioequivalents

The present invention includes multispecific antigen-binding molecules that are bioequivalent to any of the exemplary multispecific antigen-binding molecules set forth herein. Two antigen-binding proteins are considered bioequivalent if, for example, they are pharmaceutical equivalents or pharmaceutical alternatives whose rate and extent of absorption do not show a significant difference when administered at the same molar dose under similar experimental conditions, either single does or multiple dose. Some antigen-binding proteins will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, and potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and in vitro methods. Bioequivalence measures include, e.g., (a) an in vivo test in humans or other mammals, in which the concentration of the antigen-binding protein or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antigen-binding protein (or its target) is measured as a function of time; and (d) in a well-controlled clinical trial that establishes safety, efficacy, or bioavailability or bioequivalence of an antigen-binding protein.

Bioequivalent variants of the exemplary multispecific antigen-binding molecules set forth herein may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antigen-binding proteins may include variants of the exemplary multispecific antigen-binding molecules set forth herein comprising amino acid changes which modify the glycosylation characteristics of the molecules, e.g., mutations which eliminate or remove glycosylation.

Species Selectivity and Species Cross-Reactivity

According to certain embodiments of the invention, antigen-binding molecules are provided which bind to human T cell antigen (e.g., CD3) but not to the same antigen from other species. Also provided are antigen-binding molecules which bind to human target antigens (e.g., tumor antigens) but not to the same target antigens from other species. The present invention also includes antigen-binding molecules that bind to human antigens and corresponding antigens from one or more non-human species.

According to certain exemplary embodiments of the invention, antigen-binding molecules are provided which bind to human CD3 and/or a human tumor antigen and may bind or not bind, as the case may be, to one or more of mouse, rat, guinea pig, hamster, gerbil, pig, cat, dog, rabbit, goat, sheep, cow, horse, camel, cynomolgus, marmoset, rhesus or chimpanzee CD3 and/or tumor antigen. For example, in a particular exemplary embodiment of the present invention, multispecific antigen-binding molecules are provided comprising a first antigen-binding domain that binds human CD3 and cynomolgus CD3, and a second antigen-binding domain that specifically binds a human tumor antigen.

Immunoconjugates

The present invention encompasses antigen-binding molecules conjugated to a therapeutic moiety ("immunoconjugate"), such as a cytotoxin, a chemotherapeutic drug, an immunosuppressant or a radioisotope. Cytotoxic agents include any agent that is detrimental to cells. Examples of suitable cytotoxic agents and chemotherapeutic agents for forming immunoconjugates are known in the art, (see for example, WO 05/103081).

Therapeutic Formulation and Administration

The present invention provides pharmaceutical compositions comprising the multispecific antigen-binding molecules of the present invention. The pharmaceutical compositions of the invention are formulated with suitable carriers, excipients, and other agents that provide improved transfer, delivery, tolerance, and the like. A multitude of appropriate formulations can be found in the formulary known to all pharmaceutical chemists: Remington's Pharmaceutical Sciences, Mack Publishing Company, Easton, PA These formulations include, for example, powders, pastes, ointments, jellies, waxes, oils, lipids, lipid (cationic or anionic) containing vesicles (such as LIPOFECTIN™, Life Technologies, Carlsbad, CA), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antigen-binding molecule administered to a patient may vary depending upon the age and the size of the patient, target disease, conditions, route of administration, and the like. The preferred dose is typically calculated according to body weight or body surface area. When a multispecific antigen-binding molecule of the present invention is used for therapeutic purposes in an adult patient, it may be advantageous to intravenously administer the multispecific antigen-binding molecule of the present invention normally at a single dose of about 0.01 to about 20 mg/kg body weight, more preferably about 0.02 to about 7, about 0.03 to about 5, or about 0.05 to about 3 mg/kg body weight. Depending on the severity of the condition, the frequency and the duration of the treatment can be adjusted. Effective dosages and schedules for administering a multispecific antigen-binding molecule may be determined empirically; for example, patient progress can be monitored by periodic assessment, and the dose adjusted accordingly. Moreover, interspecies scaling of dosages can be performed using well-known methods in the art (e.g., Mordenti et al., 1991, *Pharmaceut. Res.* 8:1351).

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al., 1987, J. Biol. Chem. 262:4429-4432). Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pens and autoinjector delivery devices have applications in the subcutaneous delivery of a pharmaceutical composition of the present invention. Examples include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, IN), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, NJ), OPTIPEN™, OPTIPEN PRO™, OPTIPEN STARLET™, and OPTICLIK™ (sanofi-aventis, Frankfurt, Germany), to name only a few. Examples of disposable pen delivery devices having applications in subcutaneous delivery of a pharmaceutical composition of the present invention include, but are not limited to the SOLOSTAR™ pen (sanofi-aventis), the FLEXPEN™ (Novo Nordisk), and the KWIKPEN™ (Eli Lilly), the SURECLICK™ Autoinjector (Amgen, Thousand Oaks, CA), the PENLET™ (Haselmeier, Stuttgart, Germany), the EPIPEN (Dey, L. P.), and the HUMIRA™ Pen (Abbott Labs, Abbott Park IL), to name only a few.

In certain situations, the pharmaceutical composition can be delivered in a controlled release system. In one embodiment, a pump may be used (see Langer, supra; Sefton, 1987, CRC Crit. Ref. Biomed. Eng. 14:201). In another embodiment, polymeric materials can be used; see, Medical Applications of Controlled Release, Langer and Wise (eds.), 1974, CRC Pres., Boca Raton, Florida. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antigen-binding molecule or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antigen-binding molecule contained is generally about 5 to about 500 mg per dosage form in a unit dose; especially in the form of injection, it is preferred that the aforesaid antigen-binding molecule is contained in about 5 to about 100 mg and in about 10 to about 250 mg for the other dosage forms.

Therapeutic Uses of the Antigen-Binding Molecules

The present invention includes methods comprising administering to a subject in need thereof a therapeutic composition comprising a multispecific antigen-binding molecule that specifically binds a T-cell antigen (e.g., CD3) and a target antigen (e.g., a tumor-associated antigen). The therapeutic composition can comprise any of the multispecific antigen-binding molecules as disclosed herein and a pharmaceutically acceptable carrier or diluent. As used herein, the expression "a subject in need thereof" means a human or non-human animal that exhibits one or more symptoms or indicia of cancer, or who otherwise would benefit from an inhibition or reduction in target antigen activity or a depletion of target-antigen positive cells (e.g., tumor cells).

The multispecific antigen-binding molecules of the invention (and therapeutic compositions comprising the same) are useful, inter alia, for treating any disease or disorder in which stimulation, activation and/or targeting of an immune response would be beneficial. In particular, the multispecific antigen-binding molecules of the present invention may be used for the treatment, prevention and/or amelioration of any disease or disorder associated with or mediated by target antigen expression or activity or the proliferation of target-antigen positive cells. The mechanism of action by which the therapeutic methods of the invention are achieved includes killing of the cells expressing the target antigen in the presence of T cells.

The multispecific antigen-binding molecules of the present invention may be used to treat a disease or disorder associated with target antigen expression including, e.g., a cancer. Analytic/diagnostic methods known in the art, such as tumor scanning, etc., may be used to ascertain whether a patient harbors a tumor cell that is positive for the target antigen. In some cases, the cancer is selected from a solid tumor, cervical cancer, head and neck squamous cell carcinoma, melanoma, prostate cancer, acute myeloid leukemia, pancreatic cancer, colon cancer, acute lymphocytic leukemia, a non-Hodgkin's lymphoma, gastric cancer, post-transplant lymphoproliferative disorder, ovarian cancer, lung cancer, squamous cell carcinoma, non-small cell lung cancer esophageal cancer, bladder cancer, nasopharyngeal cancer, uterine cancer, liver cancer, testicular cancer, or breast cancer.

The present invention also includes methods for treating residual cancer in a subject. As used herein, the term "residual cancer" means the existence or persistence of one or more cancerous cells in a subject following treatment with an anti-cancer therapy.

According to certain aspects, the present invention provides methods for treating a disease or disorder associated with target antigen expression (e.g., a cancer) comprising administering one or more of the multispecific antigen-binding molecules described elsewhere herein to a subject after the subject has been determined to have a target antigen positive cancer. For example, the present invention includes methods for treating a cancer comprising administering a multispecific antigen-binding molecule to a patient 1 day, 2 days, 3 days, 4 days, 5 days, 6 days, 1 week, 2 weeks, 3 weeks or 4 weeks, 2 months, 4 months, 6 months, 8 months, 1 year, or more after the subject has received other immunotherapy or chemotherapy.

Combination Therapies and Formulations

The present invention provides methods which comprise administering a pharmaceutical composition comprising any of the exemplary multispecific antigen-binding molecules described herein in combination with one or more additional therapeutic agents. Exemplary additional therapeutic agents that may be combined with or administered in combination with an antigen-binding molecule of the present invention include, e.g., an anti-tumor agent (e.g. chemotherapeutic agents). In certain embodiments, the second therapeutic agent may be a monoclonal antibody, an antibody drug conjugate, a bispecific antibody conjugated to an anti-tumor agent, a checkpoint inhibitor, or combinations thereof. Other agents that may be beneficially administered in combination with the antigen-binding molecules of the invention include cytokine inhibitors, including small-molecule cytokine inhibitors and antibodies that bind to cytokines such as IL-1, IL-2, IL-3, IL-4, IL-5, IL-6, IL-8, IL-9, IL-10, IL-11, IL-12, IL-13, IL-17, IL-18, or to their respective receptors. The pharmaceutical compositions of the present invention (e.g., pharmaceutical compositions comprising a multispecific antigen-binding molecule as disclosed herein) may also be administered as part of a therapeutic regimen comprising one or more therapeutic combinations selected from a monoclonal antibody that may interact with a different antigen on the cell surface, a bispecific antibody that has one arm that binds to an antigen on the tumor cell surface and the other arm binds to an antigen on a T cell, an antibody drug conjugate, a bispecific antibody conjugated with an anti-tumor agent, a checkpoint inhibitor, for example, one that targets, PD-1 or CTLA-4, or combinations thereof. In certain embodiments, the checkpoint inhibitors may be selected from PD-1 inhibitors, such as pembrolizumab (Keytruda), nivolumab (Opdivo), or cemiplimab (REGN2810). In certain embodiments, the checkpoint inhibitors may be selected from PD-L1 inhibitors, such as atezolizumab (Tecentriq), avelumab (Bavencio), or Durvalumab (Imfinzi)). In certain embodiments, the checkpoint inhibitors may be selected from CTLA-4 inhibitors, such as ipilimumab (Yervoy). Other combinations that may be used in conjunction with an antibody of the invention are described above.

The present invention also includes therapeutic combinations comprising any of the antigen-binding molecules mentioned herein and an inhibitor of one or more of VEGF, Ang2, DLL4, EGFR, ErbB2, ErbB3, ErbB4, EGFRvIII, cMet, IGF1R, IL-10, B-raf, PDGFR-α, PDGFR-β, FOLH1 (PSMA), PRLR, STEAP1, STEAP2, TMPRSS2, MSLN, CA9, uroplakin, or any of the aforementioned cytokines, wherein the inhibitor is an aptamer, an antisense molecule, a ribozyme, an siRNA, a peptibody, a nanobody, an antibody, a bispecific antibody or an antibody fragment (e.g., Fab fragment; F(ab')$_2$ fragment; Fd fragment; Fv fragment; scFv; dAb fragment; or other engineered molecules, such as diabodies, triabodies, tetrabodies, minibodies and minimal recognition units). The antigen-binding molecules of the invention may also be administered and/or co-formulated in combination with antivirals, antibiotics, analgesics, corticosteroids and/or NSAIDs. The antigen-binding molecules of the invention may also be administered as part of a treatment regimen that also includes radiation treatment and/or conventional chemotherapy.

The additional therapeutically active component(s) may be administered just prior to, concurrent with, or shortly after the administration of an antigen-binding molecule of the present invention; (for purposes of the present disclosure, such administration regimens are considered the administration of an antigen-binding molecule "in combination with" an additional therapeutically active component).

The present invention includes pharmaceutical compositions in which an antigen-binding molecule of the present invention is co-formulated with one or more of the additional therapeutically active component(s) as described elsewhere herein.

Administration Regimens

According to certain embodiments of the present invention, multiple doses of a multispecific antigen-binding molecule may be administered to a subject over a defined time course. The methods according to this aspect of the invention comprise sequentially administering to a subject multiple doses of an antigen-binding molecule of the invention. As used herein, "sequentially administering" means that each dose of an antigen-binding molecule is administered to the subject at a different point in time, e.g., on different days separated by a predetermined interval (e.g., hours, days, weeks or months). The present invention includes methods which comprise sequentially administering to the patient a single initial dose of an antigen-binding molecule, followed by one or more secondary doses of the antigen-binding molecule, and optionally followed by one or more tertiary doses of the antigen-binding molecule.

The terms "initial dose," "secondary doses," and "tertiary doses," refer to the temporal sequence of administration of the antigen-binding molecule of the invention. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of the antigen-binding molecule, but generally may differ from one another in terms of frequency of administration. In certain embodiments, however, the amount of an antigen-binding molecule contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

In one exemplary embodiment of the present invention, each secondary and/or tertiary dose is administered 1 to 26 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, 15, 15½, 16, 16½, 17, 17½, 18, 18½, 19, 19½, 20, 20½, 21, 21½, 22, 22½, 23, 23½, 24, 24½, 25, 25½, 26, 26½, or more) weeks after the immediately preceding dose. The phrase "the immediately preceding dose," as used herein, means, in a sequence of multiple administrations, the dose of antigen-binding molecule which is administered to a patient prior to the administration of the very next dose in the sequence with no intervening doses.

The methods according to this aspect of the invention may comprise administering to a patient any number of secondary and/or tertiary doses of an antigen-binding molecule. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 2 weeks after the immediately preceding dose. Similarly, in embodiments involving multiple tertiary doses, each tertiary dose may be administered at the same frequency as the other tertiary doses. For example, each tertiary dose may be administered to the patient 2 to 4 weeks after the immediately preceding dose. Alternatively, the frequency at which the secondary and/or tertiary doses are administered to a patient can vary over the course of the treatment regimen. The frequency of administration may also be adjusted during the course of treatment by a physician depending on the needs of the individual patient following clinical examination.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Method for Binding by Flow Cytometry: In the following examples, binding for the various molecules was determined using the following flow cytometry method. Flow cytometric analysis was utilized to determine binding of MAGEA4×CD3 multispecific molecules to RAJI/HLA-A2/B2M/MAGEA4(peptide a), A375/hHLA-A2/B2M/MAGEA4(peptide b), RAJI/HLA-A2/B2M/NY-ESO-1, and JURKAT cells, followed by detection with an APC-labeled anti-human IgG antibody. Briefly, $1\times10^5$ cells/well were incubated for 30 minutes at 4° C. with a serial dilution of MAGEA4×CD3 multispecific molecules or Isotype control (a human IgG4 stealth antibody that binds a human antigen with no cross-reactivity to human MAGEA4 or CD3). After incubation, the cells were washed twice with cold PBS containing 1% filtered FBS and a PE-conjugated anti-human secondary antibody was added to the cells and incubated for an additional 30 minutes. Wells containing no antibody or secondary only were used as a control. After incubation, cells were washed, re-suspended in 200 µL cold PBS containing 1% filtered FBS and analyzed by flow cytometry on a BD FACS Canto II.

Method for Cytotoxicity Assay: In the following examples, cytotoxicity of the various molecules was determined using the following cytotoxicity assay. In order to monitor the killing of MAGEA4+ cells in the presence of MAGEA4×CD3 as single agents or in combination with an EGFRxCD28 bispecific antibody and/or a PD-1 antibody, A375 cells, *ScaBER* cells, NCI-H1755 metastatic (from liver) cells, and NCI-H1755 cells were labeled with 1 uM of the fluorescent tracking dye Violet Cell Tracker. After labeling, cells were plated overnight at 37° C. Separately, human PBMCs were plated in supplemented RPMI media at $1\times10^6$ cells/mL and incubated overnight at 37° C. in order to enrich for lymphocytes by depleting adherent macrophages, dendritic cells, and some monocytes. The next day, target cells were co-incubated with adherent cell-depleted naïve PBMC (Effector/Target cell 10:1 ratio), a serial dilution of MAGEA4×CD3 multispecific molecules and a fixed concentration of EGFRxCD28 and/or anti-PD1 antibodies for 96 hours at 37° C. Cells were removed from cell culture plates using Trypsin-EDTA dissociation buffer, and analyzed by FACS on a FACS BD LSRFortessa-X20. For FACS analysis, cells were stained with a dead/live Near IR Reactive (Invitrogen) dye. 5E05 counting beads were added to each well immediately before FACS analysis. 1E05 beads were collected for each sample. For the assessment of specificity of killing, cells were gated on live Violet labeled populations. Percent of live population was recorded and used for the calculation of survival.

Example 1: T Cell Activation is Dependent on the Presence of Target Cells

T cell activation was evaluated for each of the molecular formats illustrated in FIGS. 1A, 1B and 1C. T cell activation and upregulation of the PD-1 marker were assessed by incubating cells with directly conjugated antibodies to CD2, CD4, CD8, CD25 and PD-1, and by reporting the percent of late activated (CD25+/CD8+) T cells and PD-1+/CD4+ T cells out of total T cells (CD2+).

As shown in FIG. 2, the exemplary multispecific molecule of the present invention (FIG. 1C structure) did not activate T cells in the absence of target cells. The "ZERO" represent a T cell only control.

Example 2: Cytotoxicity of Multispecific Molecules Relative to Conventional Formats Cytotoxicity of an exemplary multispecific molecule of the present invention (FIG. 1C structure) was measured as discussed above, and compared to the cytotoxicity of conventionally formatted molecules having the same antigen-binding domains (FIGS. 1A and 1B). The CD3-binding domains used in this example have a moderate binding affinity to human CD3. The target antigen binding domain used in this example binds to a MAGEA4 (Melanoma-Associated Antigen A4) peptide. The "Control" is a positive control that targets the scaffold of all HLA molecules to provide a maximum cytotoxicity against which to compare the other formats.

Figure 3:
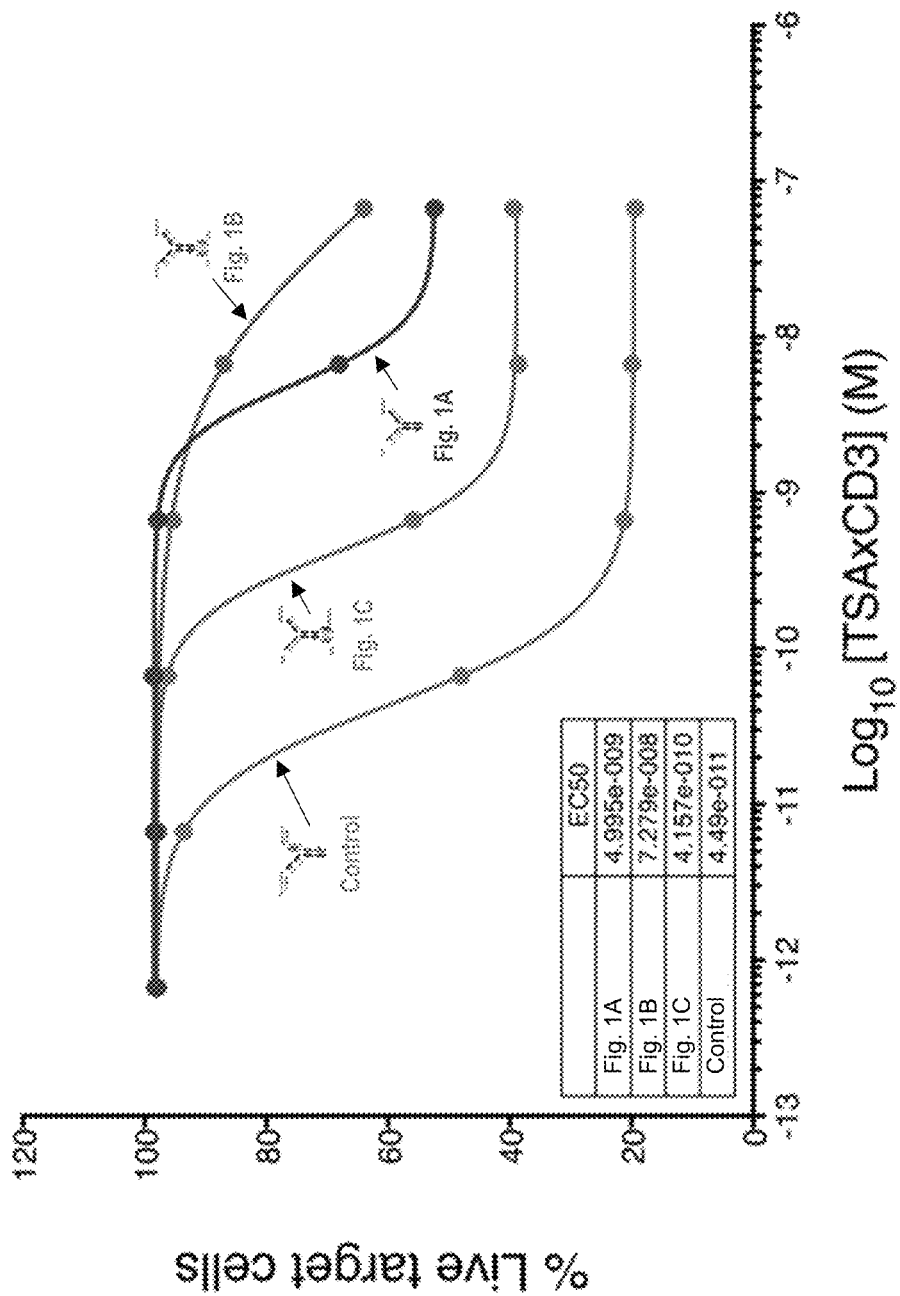
FIG. 3 shows the cytotoxic activity of molecules having each of the formats illustrated in FIGS. 1A, 1B and 1C, in the presence of human PBMC and target cells (A375), compared to a positive control that induces maximal cell killing. The CD3-binding domains of the molecules comprise the variable regions of a 7221G anti-CD3 antibody. The molecule having the structure of FIG. 1C was significantly more potent than the molecules having the structures of FIGS. 1A and 1B.

As illustrated in FIG. 3, the exemplary multispecific molecule of the present invention (FIG. 1C structure) more potently killed target cells than did the molecules having conventional bispecific formats (FIG. 1A structure, and FIG. 1B structure).

Example 3: Cytotoxicity of Multispecific Molecules Relative to Conventional Formats in Combination with an Anti-PD-1 Antibody, a Co-Stimulatory Bispecific Antibody, or Both Cytotoxicity of an exemplary multispecific molecule of the present invention (FIG. 1C structure) was measured as discussed above, and compared to the cytotoxicity of conventionally formatted molecules having the same antigen-binding domains (FIGS. 1A and 1B) in combination with an anti-PD-1 antibody, a co-stimulatory bispecific EGFR× CD28 antibody, or both an anti-PD-1 antibody and a costimulatory bispecific EGFR×CD28 antibody. The positive control, and the CD3 and target antigen-binding domains were as discussed above in Example 2.

Figure 4A:
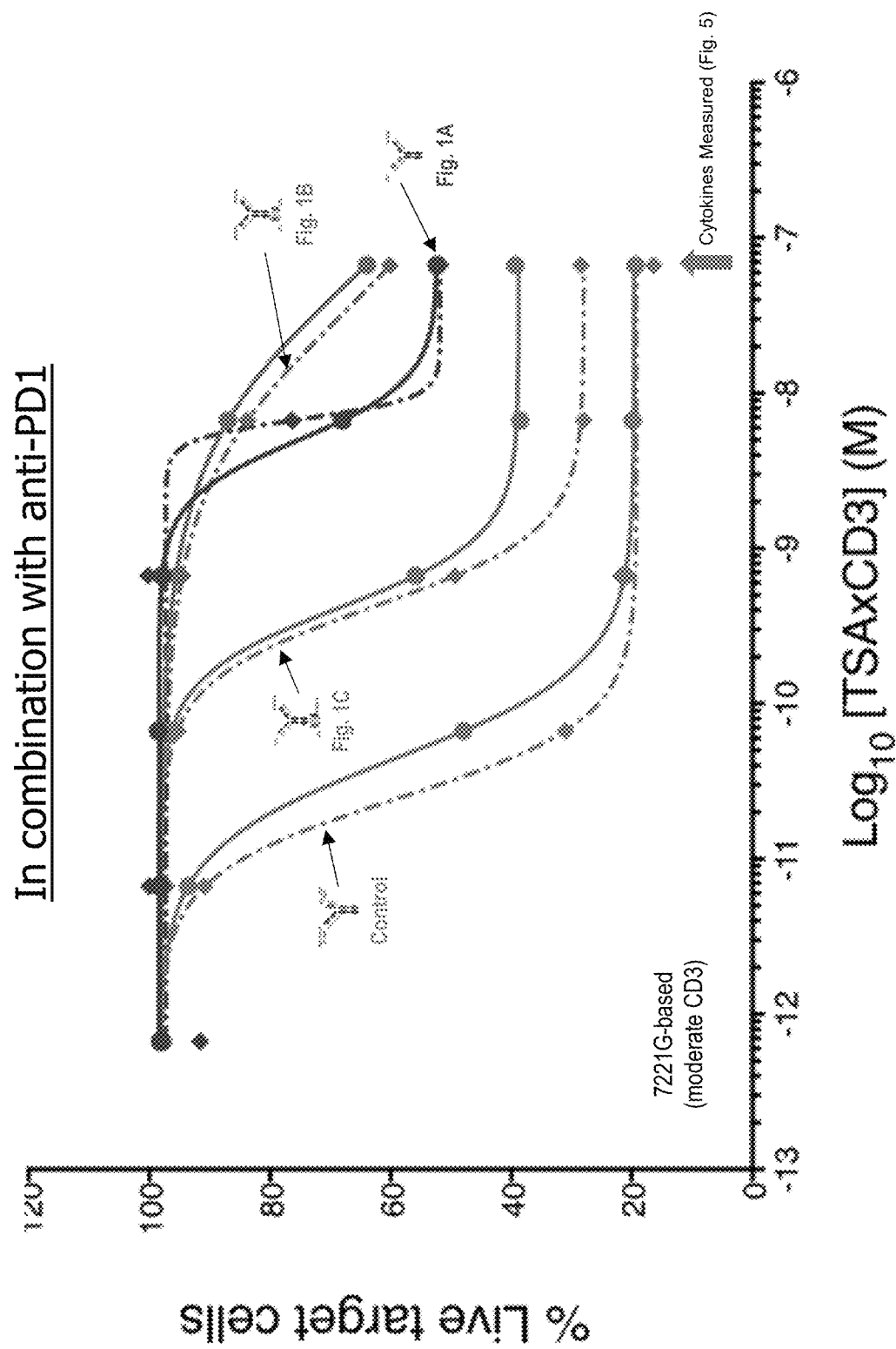
FIGS. 4A, 4B and 4C show the cytotoxic activity of molecules having each of the formats illustrated in FIGS. 1A, 1B and 1C, in the presence of human PBMC and target cells (A375), in combination with an anti-PD-1 antibody (FIG. 4A), a co-stimulatory bispecific EGFR×CD28 antibody (FIG. 4B), or both an anti-PD-1 antibody and a co-stimulatory bispecific EGFR×CD28 antibody (FIG. 4C) compared to a positive control that induces maximal cell killing. The CD3-binding domains of the molecules comprise the variable regions of a 7221G anti-CD3 antibody. The molecule having the structure of FIG. 1C was significantly more potent in combination with these additional antibodies than the molecules having the structures of FIGS. 1A and 1B.
Figure 4B:
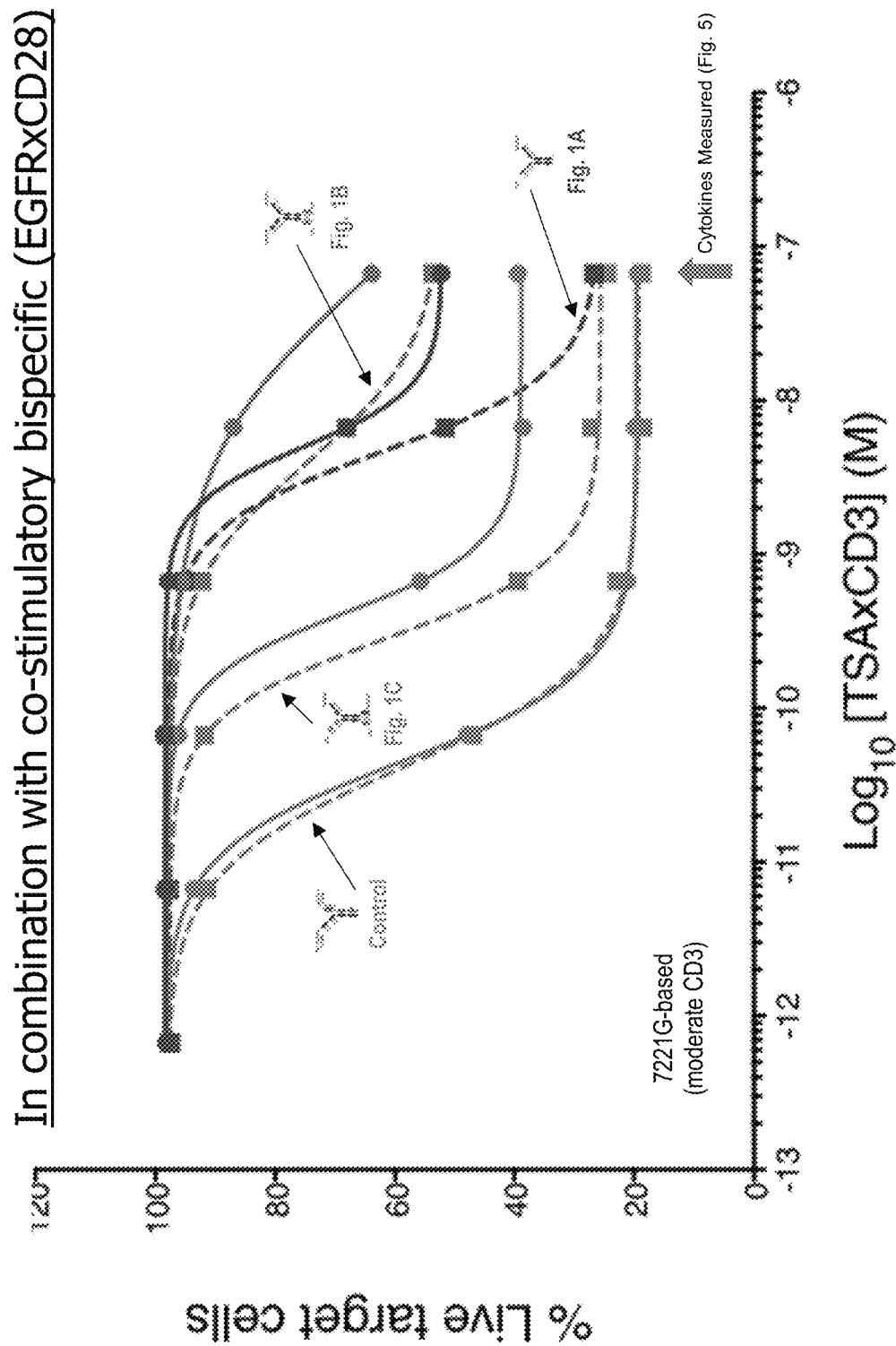
Figure 4C:
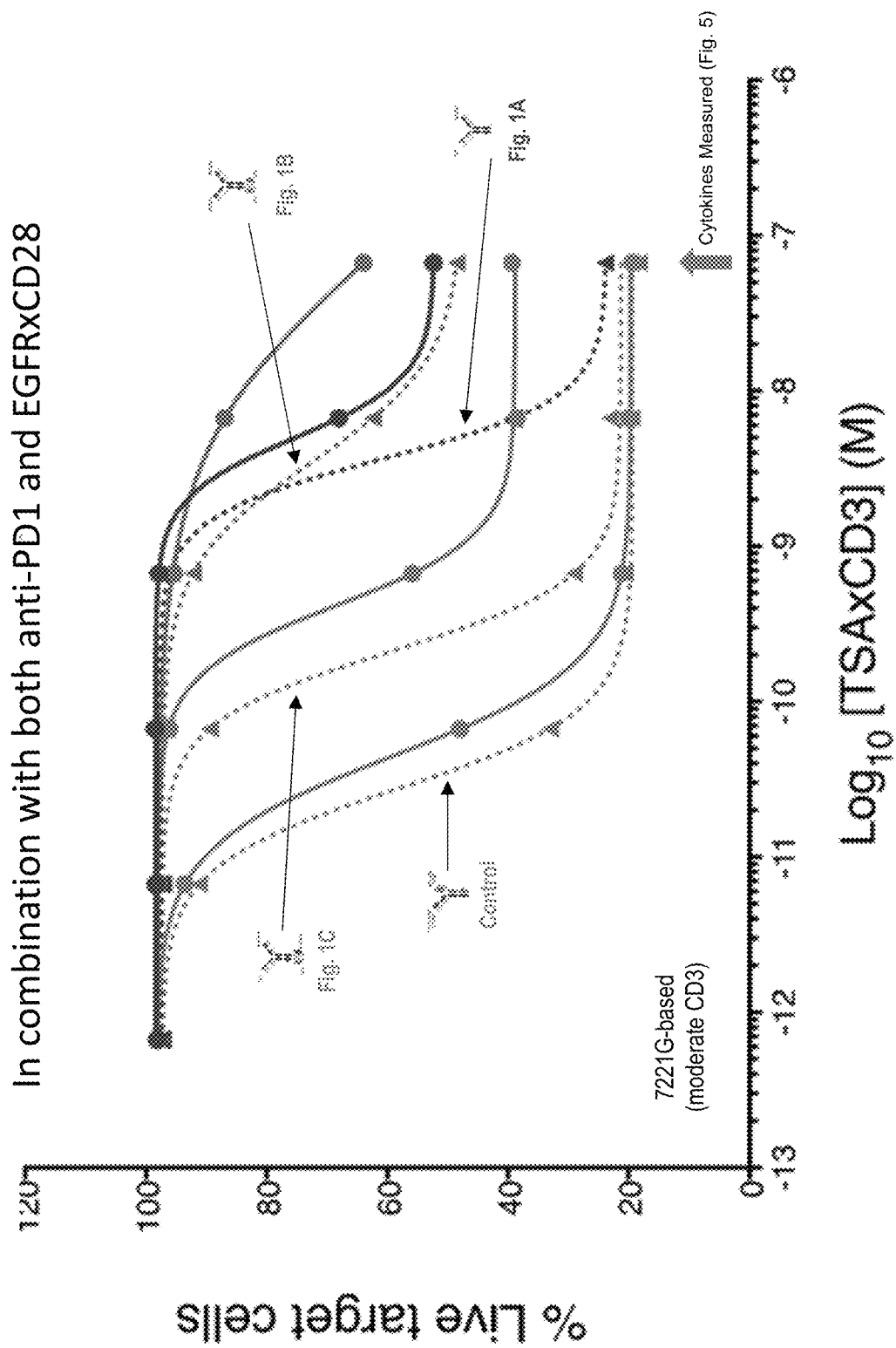

As illustrated in FIGS. 4A, 4B and 4C, the addition of an anti-PD-1 antibody, a co-stimulatory bispecific EGFR× CD28 antibody, or both, further enhanced the potency of the exemplary multispecific molecule of the present invention (FIG. 1C structure). The solid lines represent the cytotoxicity of the single agent (as shown in FIG. 3), and the dashed lines represent the cytotoxicity of the respective combination.

Figure 5:
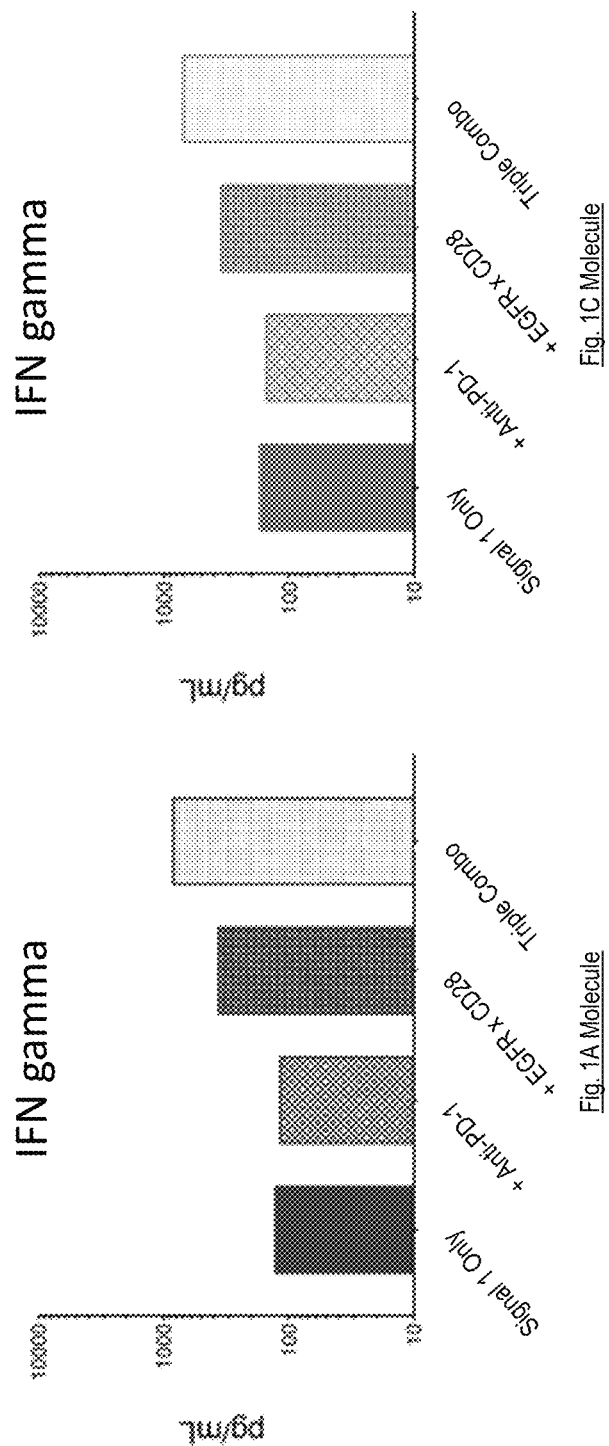
FIG. 5 shows the measured cytokine levels of the molecule having the structure of FIG. 1C (right panel) compared to the molecule having the structure of FIG. 1A (left panel) at the point of maximal antibody concentration shown in FIGS. 4A, 4B and 4C. The CD3-binding domains of the molecules comprise the variable regions of a 7221G anti-CD3 antibody. The molecule having the structure of FIG. 1C does not show greater levels of cytokine release in spite of the significantly greater cytotoxic activity.
Figures 6A, 6B:
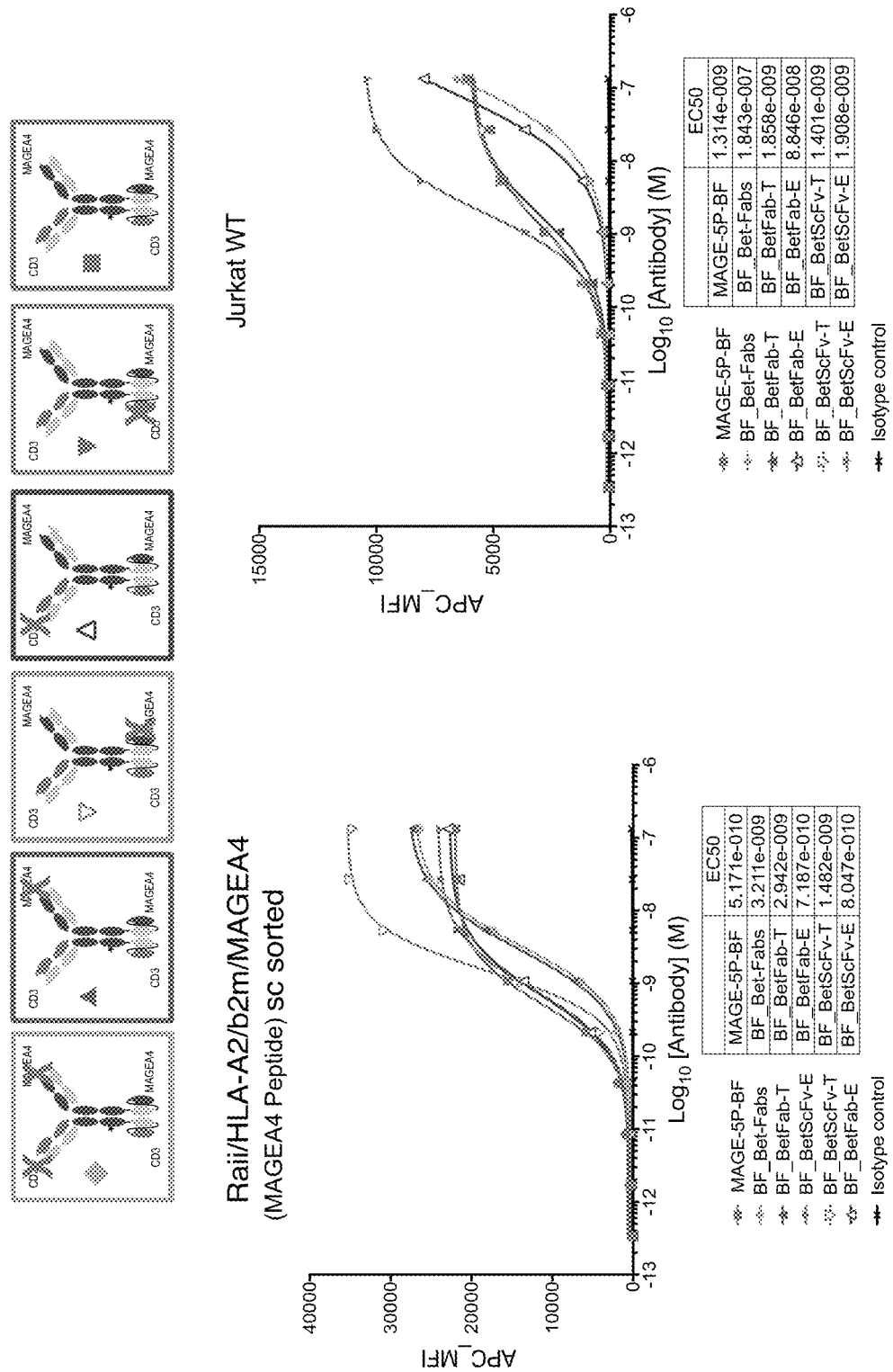
FIGS. 6A, 6B, 6C and 6D show binding of the molecule having the structure of FIG. 1C and modified versions of this molecule (with inactive domains—noted by an X in the legend) to Raji cells (FIG. 6A) or A375 cells (FIG. 6C) overexpressing a MAGEA4 peptide, or CD3+ Jurkat cells (FIGS. 6B and 6D). The CD3-binding domains of the molecules illustrated in FIGS. 6A and 6B comprise the variable regions of a 7195P anti-CD3 antibody. The CD3-binding domains of the molecules illustrated in FIGS. 6C and 6D comprise the variable regions of a 7221G anti-CD3 antibody.
Figures 6C, 6D:
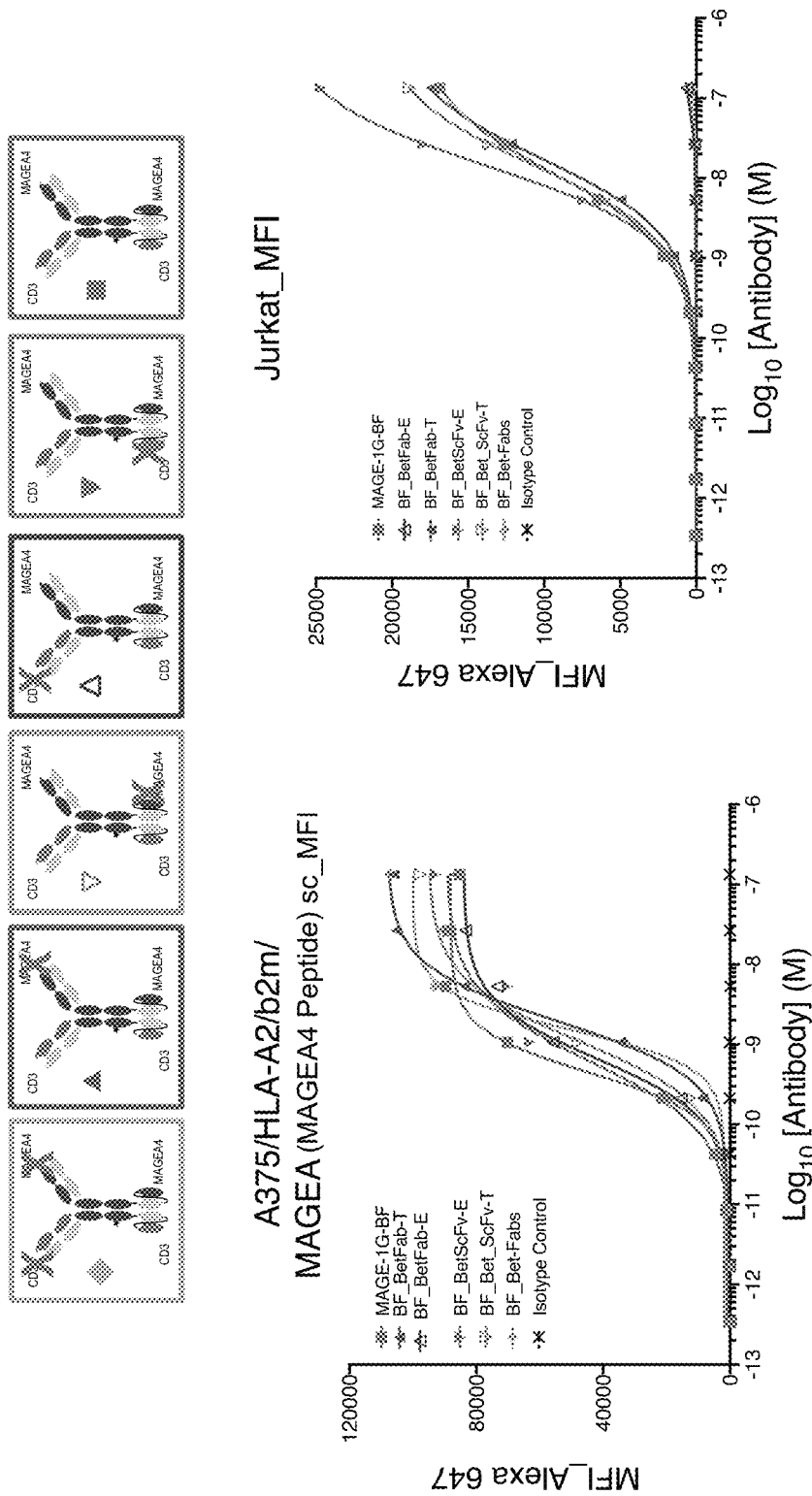

In addition to cytotoxicity, the supernatant of the assay wells from the human PBMC assay were assessed for Th1/Th2 cytokine release using the BD cytometric bead array human kit and following the manufacturer's protocol. As illustrated in FIG. 5, the greater cytotoxicity of the exemplary multispecific molecules of the present invention (FIG. 1C structure) did not result in any greater cytokine release as compared to the conventional bispecific antibody format (FIG. 1A structure).

This set of experiments confirms that: (a) at maximum concentration in the cytotoxicity assay, the molecule having the structure of FIG. 1C exhibited greater potency than did the molecule having the structure of FIG. 1A with comparable levels of cytokine release; (b) the EC50 for the cytotoxicity of the molecule having the structure of FIG. 1C (single agent) was lower than that observed for the molecule having the structure of FIG. 1A (single agent); (c) at maximum concentration in the cytotoxicity assay, the molecule having the structure of FIG. 1C exhibited greater potency in combination with an anti-PD-1 antibody than did the molecule having the structure of FIG. 1A (anti-PD-1 combo) with comparable levels of cytokine release; (d) the EC50 for the cytotoxicity of the molecule having the structure of FIG. 1C in combination with an anti-PD-1 antibody was lower than that observed for the molecule having the structure of FIG. 1A (anti-PD-1 combo); (e) at maximum concentration in the cytotoxicity assay, the molecule having the structure of FIG. 1C exhibited greater potency in combination with an anti-EGFR×CD28 bispecific antibody than did the molecule having the structure of FIG. 1A (anti-EGFR×CD28 combo) with comparable levels of cytokine release; (f) the EC50 for the cytotoxicity of the molecule having the structure of FIG. 1C in combination with an anti-EGFR×CD28 bispecific antibody was lower than that observed for the molecule having the structure of FIG. 1A (anti-EGFR×CD28 combo); (g) at maximum concentration in the cytotoxicity assay, the molecule having the structure of FIG. 1C exhibited greater potency in combination with an anti-PD-1 antibody and an anti-EGFR×CD28 bispecific antibody than did the molecule having the structure of FIG. 1A (triple combo) with comparable levels of cytokine release; (h) the EC50 for the cytotoxicity of the molecule having the structure of FIG. 1C in combination with an anti-PD-1 antibody and an anti-EGFR×CD28 bispecific antibody was lower than that observed for the molecule having the structure of FIG. 1A (triple combo).

Example 4: Potency of the Multispecific Molecules is Enhanced by Two Effector Binding Domains Binding of an exemplary multispecific molecule (FIG. 1C structure) to target cells overexpressing a MAGEA4 peptide and CD3+ Jurkat cells was measured as discussed above. Binding to these cells was also evaluated for modifications of the FIG. 1C structure in which one or more of the antigen-binding domains was made inactive. The inactive domains are illustrated with an "X" in the legend of the figures.

As illustrated in FIGS. 6A-6D, the binding data showed that the combination of two antigen-binding domains (e.g., a single Fab and a single scFv) bound to the target cells with greater affinity (lower EC50) than did a molecule with a single Fab domain or molecule with a single scFv domain. As expected, the isotype control molecule showed no binding. No distinction in the binding pattern was observed irrespective of the source of the anti-CD3 binding domain.

Figure 7A:
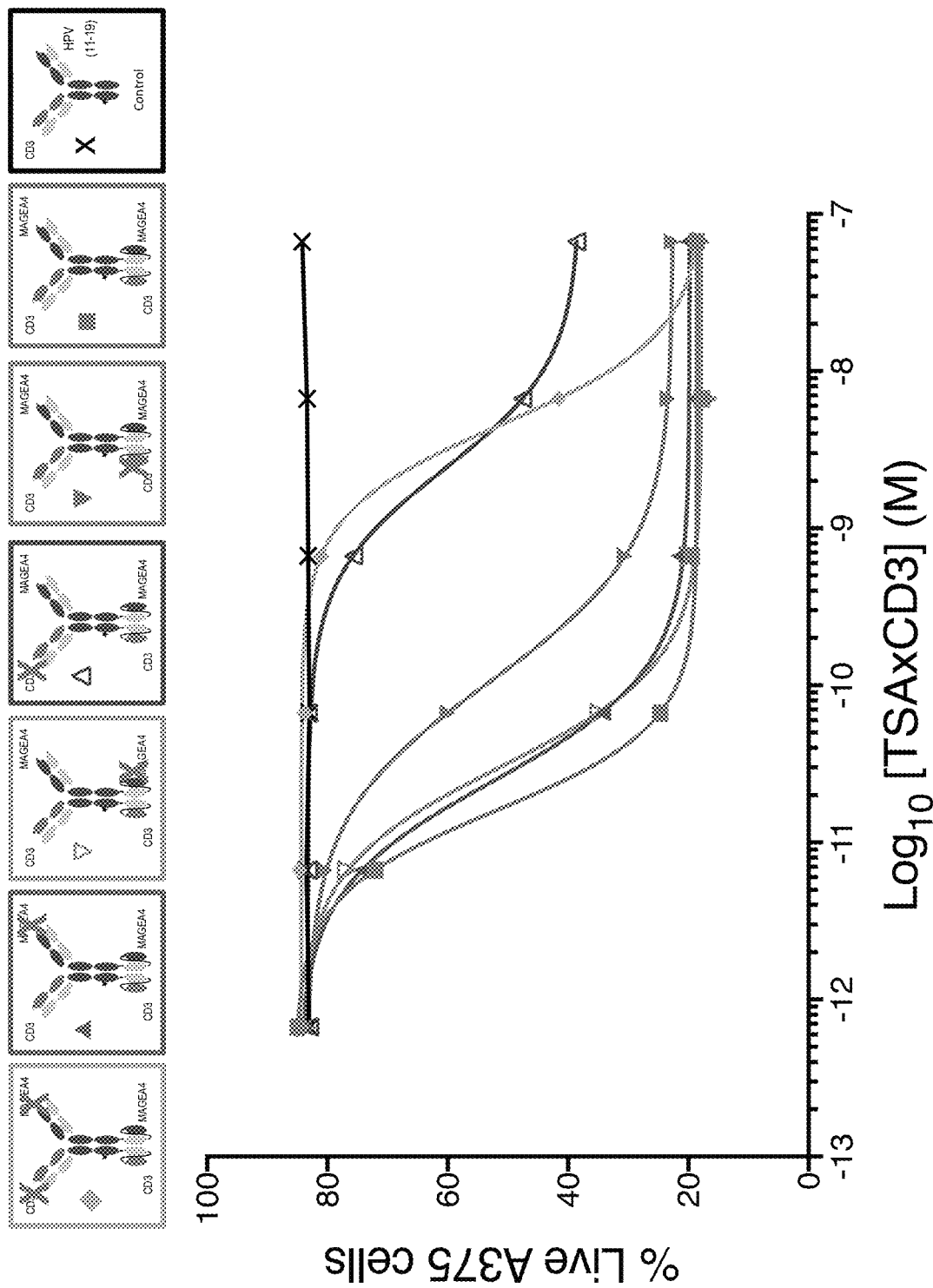
FIGS. 7A and 7B show the cytotoxic activity of the same molecules shown in FIGS. 6A and 6B (FIG. 7A), and FIGS. 6C and 6D (FIG. 7B). The molecule having the structure of FIG. 1C showed the greatest cytotoxic potency, followed by the molecules with two active T-cell antigen (e.g., CD3) binding domains. A similar pattern of cytotoxicity was observed irrespective of the source of the anti-CD3 binding domains.
Figure 7B:
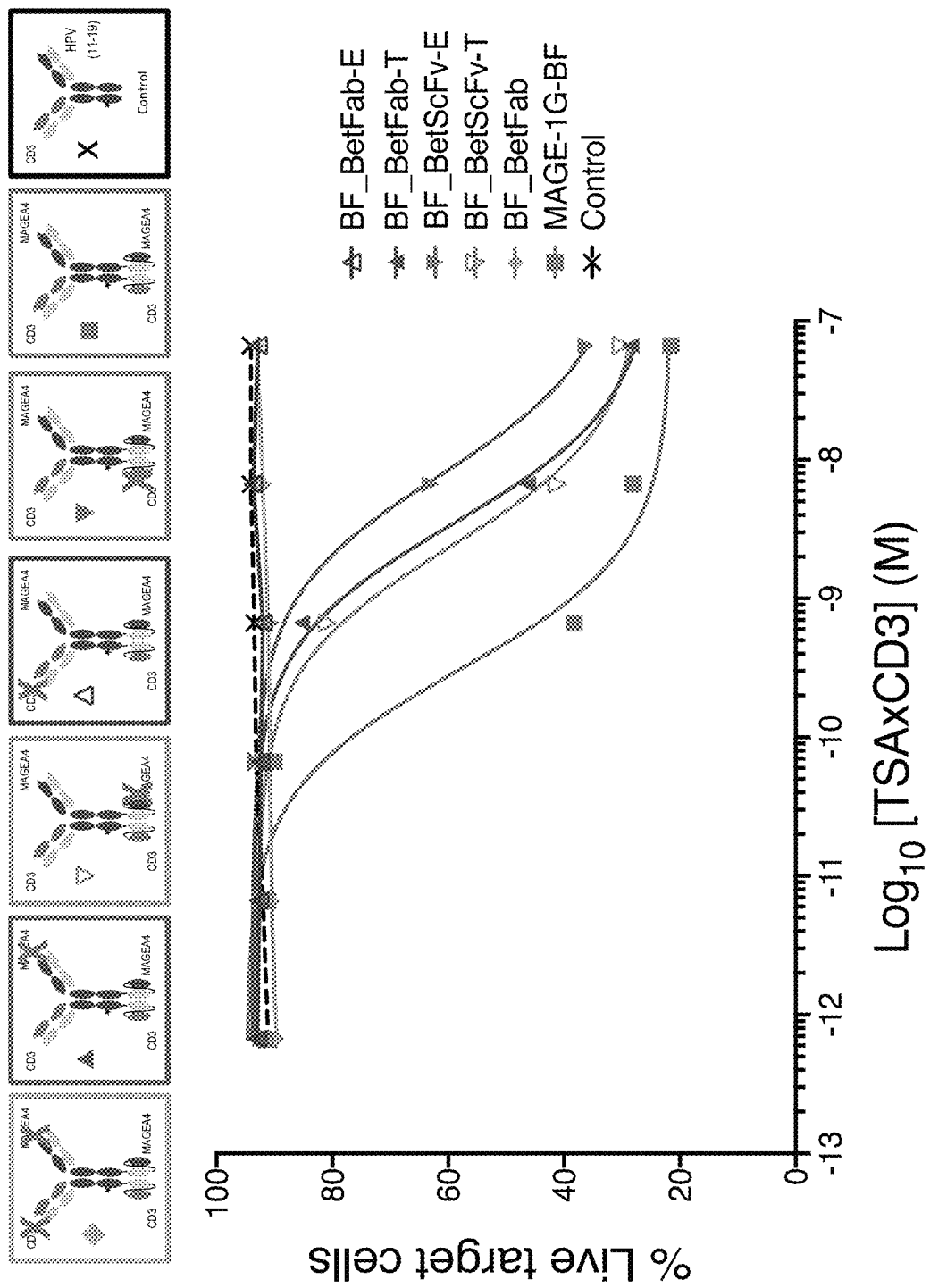

In addition to binding, cytotoxicity of these molecules was also determined using the method discussed above. As illustrated in FIGS. 7A and 7B, the exemplary multispecific molecule (FIG. 1C structure) of the present invention showed the greatest cytotoxic potency, followed by the two modified molecules comprising two T-cell antigen (CD3) binding domains but only a single target antigen (MAGEA4) binding domain (scFv or Fab). Again, the same cytotoxic pattern was observed irrespective of the source of the anti-CD3 binding domain. The negative control (FIG. 1A format) comprised an irrelevant target antigen binding domain.

Example 5: C-Terminal scFv Domains Enhance Potency of the Multispecific Molecules Relative to C-Terminal Fab Domains Binding of an exemplary multispecific molecule (FIG. 1C structure) to target cells overexpressing a MAGEA4 peptide and CD3+ Jurkat cells was measured as discussed above. Binding to these cells was also evaluated for modifications of the FIG. 1C structure to replace the C-terminal scFv domains with Fab domains (FIG. 1E structure), or in which the N-terminal Fab domains were made inactive. The inactive domains are illustrated with an "X" in the legend of the figures.

Figures 8A, 8B:
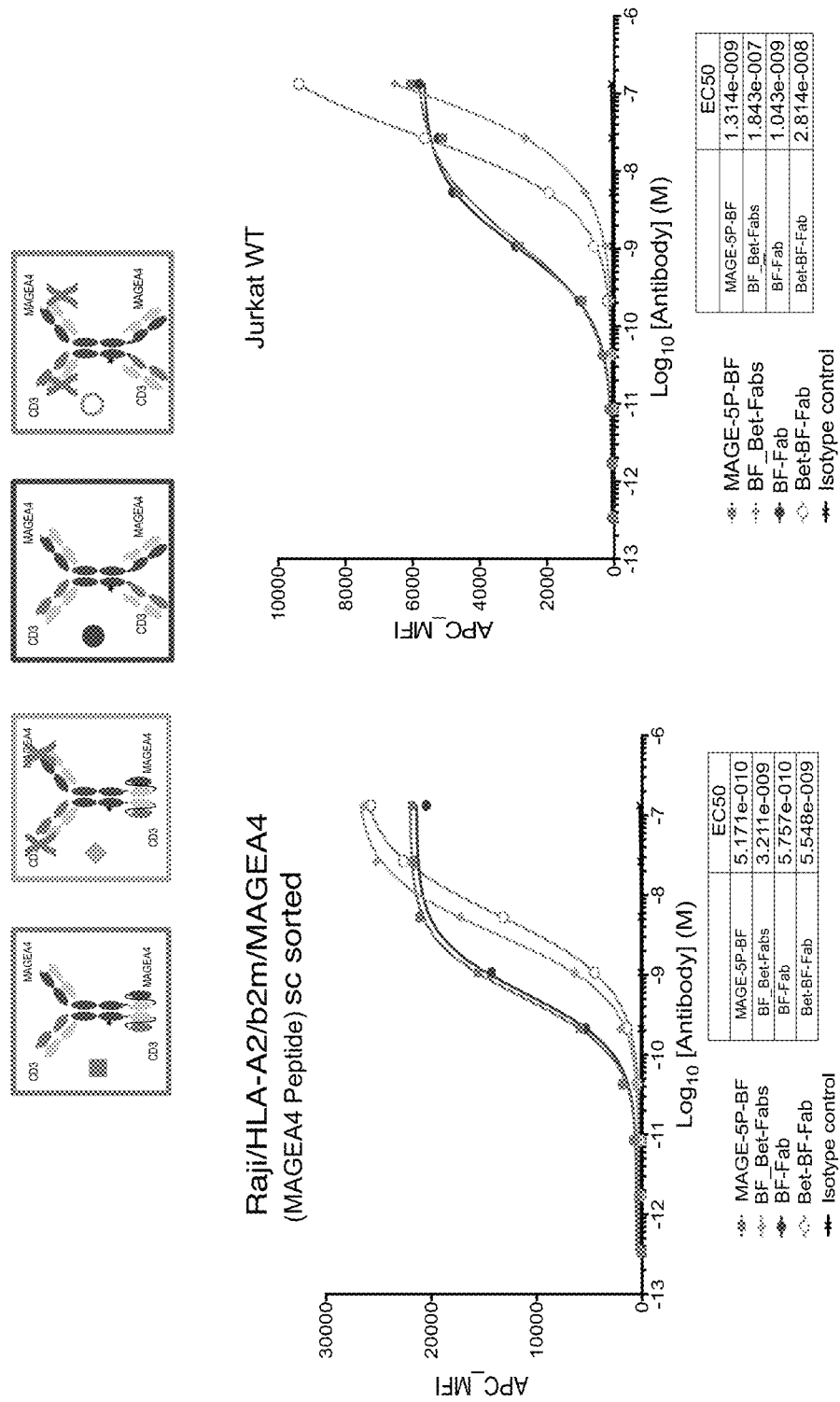
FIGS. 8A and 8B show binding of the molecule having the structure of FIG. 1C and modified versions of this molecule (with C-terminal Fab domains or inactive domains—noted by an X in the legend) to Raji cells overexpressing a MAGEA4 peptide (FIG. 8A) or CD3+ Jurkat cells (FIG. 8B). The CD3-binding domains of the molecules comprise the variable regions of a 7195P anti-CD3 antibody.

Similarly to the binding discussed in Example 4, and as illustrated in FIGS. 8A and 8B, the binding data showed that the combination of two antigen-binding domains (e.g., a single Fab and a single scFv, or two Fabs) bound to the target cells with greater affinity (lower EC50) than did a molecule with a single Fab domain or molecule with a single scFv domain. As shown in the tables of FIGS. 8A and 8B, the molecules having the structures of FIG. 1C and FIG. 1E bind with comparable binding titrations.

Figure 9:
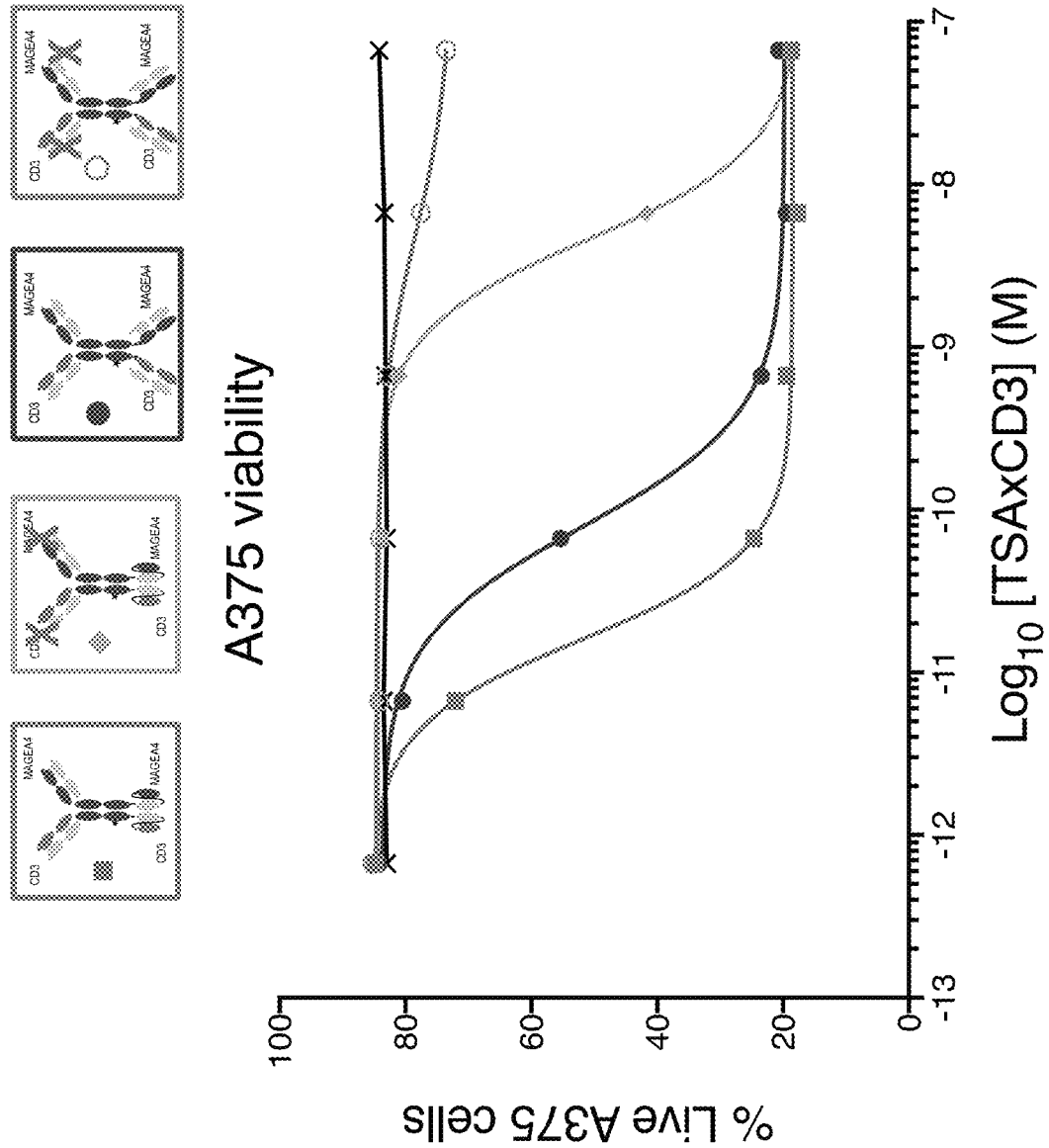
FIG. 9 shows the cytotoxic activity of the same molecules shown in FIGS. 8A and 8B. The CD3-binding domains of the molecules comprise the variable regions of a 7195P anti-CD3 antibody. The molecule having the structure of FIG. 1C showed the greatest cytotoxic potency, followed by the molecule having the structure of FIG. 1E.

In addition to binding, cytotoxicity of these molecules was also determined using the method discussed above. As illustrated in FIG. 9, the exemplary multispecific molecule (FIG. 1C structure) of the present invention showed the greatest cytotoxic potency, followed by the modified molecule comprising C-terminal Fab domains in place of the two scFv domains.

Example 6: Single Chain Bivalency for T-Cell Antigen Enhances Potency of the Multispecific Molecules Relative to Multiple Chain Bivalency Binding of an exemplary multispecific molecule (FIG. 1C structure) to target cells overexpressing a MAGEA4 peptide and CD3+ Jurkat cells was measured as discussed above. Binding to these cells was also evaluated for the molecule having the structure illustrated in FIG. 1D, in which the MAGEA4-binding domain and the CD3-binding domain are swapped such that the two sets of antigen-binding domains are located on two separate polypeptide chains.

As illustrated in FIGS. 10A and 10B, the binding data showed similar binding of the two molecular structures to each of the two cell types.

Figures 11A, 11B:
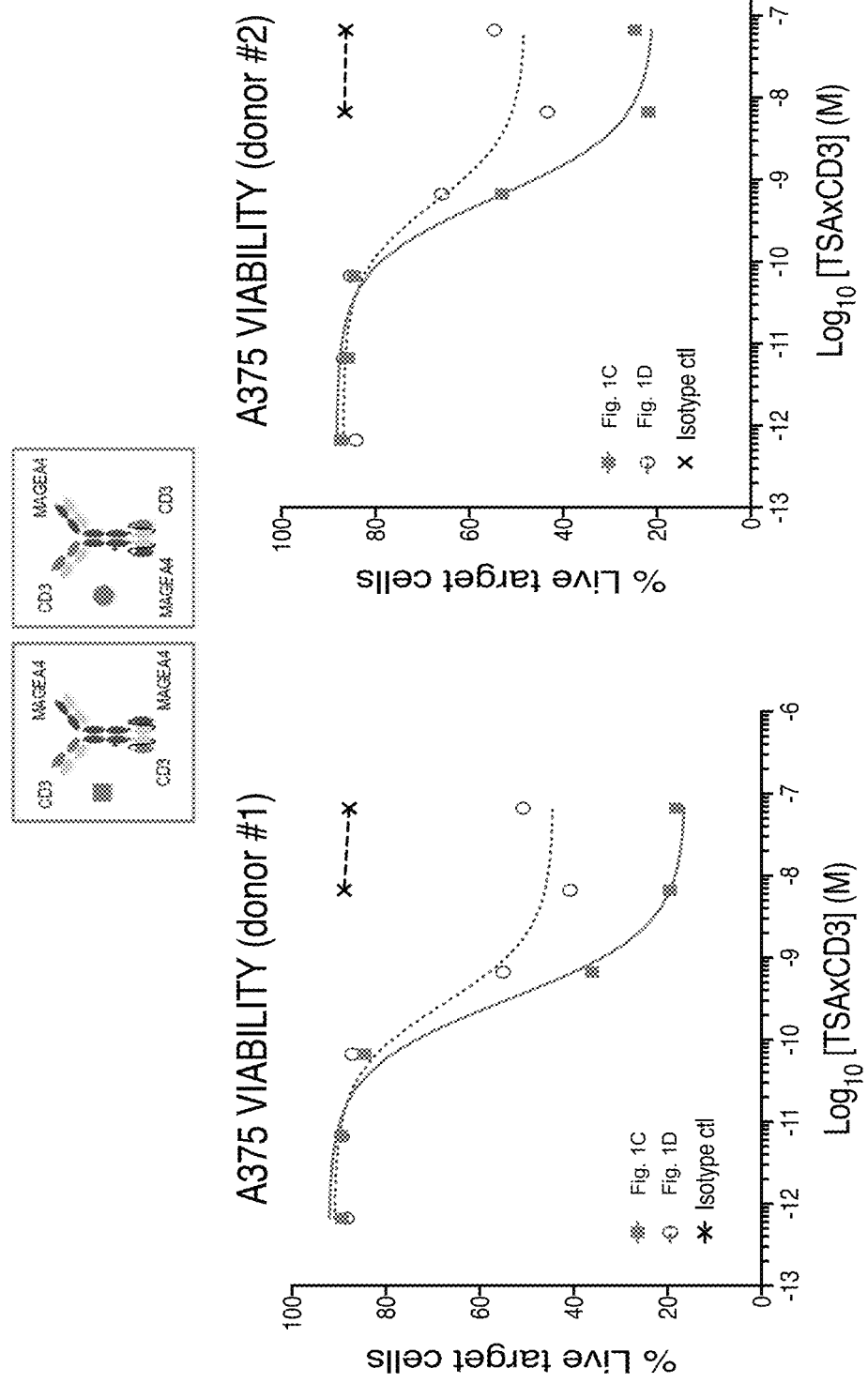
FIGS. 11A and 11B show the cytotoxic activity of the same molecules shown in FIGS. 10A and 10B on A375 cells from two different donor sources. The CD3-binding domains of the molecules comprise the variable regions of a 7221G anti-CD3 antibody. The molecule having the structure of FIG. 1C was more potent than the molecule having the structure of FIG. 1D.

In addition to binding, cytotoxicity of these molecules was also determined using the method discussed above. As illustrated in FIGS. 11A and 11B, the exemplary multispecific molecule (FIG. 1C structure) of the present invention showed the greater cytotoxic potency relative to the molecule having the structure of FIG. 1D, confirming that the presence of two T-cell antigen binding domains on a single polypeptide chain provides enhanced cytotoxic potency.

Example 7: Relative Cytotoxicity of Multispecific Molecules Targeting One or Two Antigens Relative to Conventional Formats Alone or in Combination with an Anti-PD-1 Antibody and a Co-Stimulatory Bispecific Antibody Cytotoxicity of two exemplary multispecific molecules of the present invention (FIG. 1C and FIG. 1F structures) was measured as discussed above, and compared to the cytotoxicity of a conventionally formatted molecule (FIG. 1A), alone or in combination with an anti-PD-1 antibody and a co-stimulatory bispecific EGFRxCD28 antibody. This example uses a positive control with greater specificity than that used in prior Examples to show the greater distinction between the molecules having the structures of FIGS. 1C and 1F, and the combinations of these molecules with the co-stimulatory bispecific antibody and the anti-PD-1 antibody. The CD3 antigen-binding domains used in this example have a strong binding affinity to human CD3, and the target antigen-binding domains (MAGEA4a) were as discussed above in Example 2. The negative control (FIG. 1A format) comprised an irrelevant target antigen binding domain. The second target antigen binding domain (MAGEA4b) used in this example for the molecule having the structure of FIG. 1F binds to an epitope of MAGEA4 that is completely distinct from the epitope bound by the first target antigen binding domain.

As illustrated in FIGS. 12A and 12B, the multispecific molecule that targets two different low density antigens on tumor cells shows increased potency relative to the multispecific molecule that targets only a single tumor antigen, and both molecules show greater potency than the conventionally formatted molecule having the structure of FIG. 1A. The addition of an anti-PD-1 antibody and a co-stimulatory bispecific EGFRxCD28 antibody further enhanced the potency of the exemplary multispecific molecules of the present invention (FIGS. 1C and 1F structures).

Figure 13:
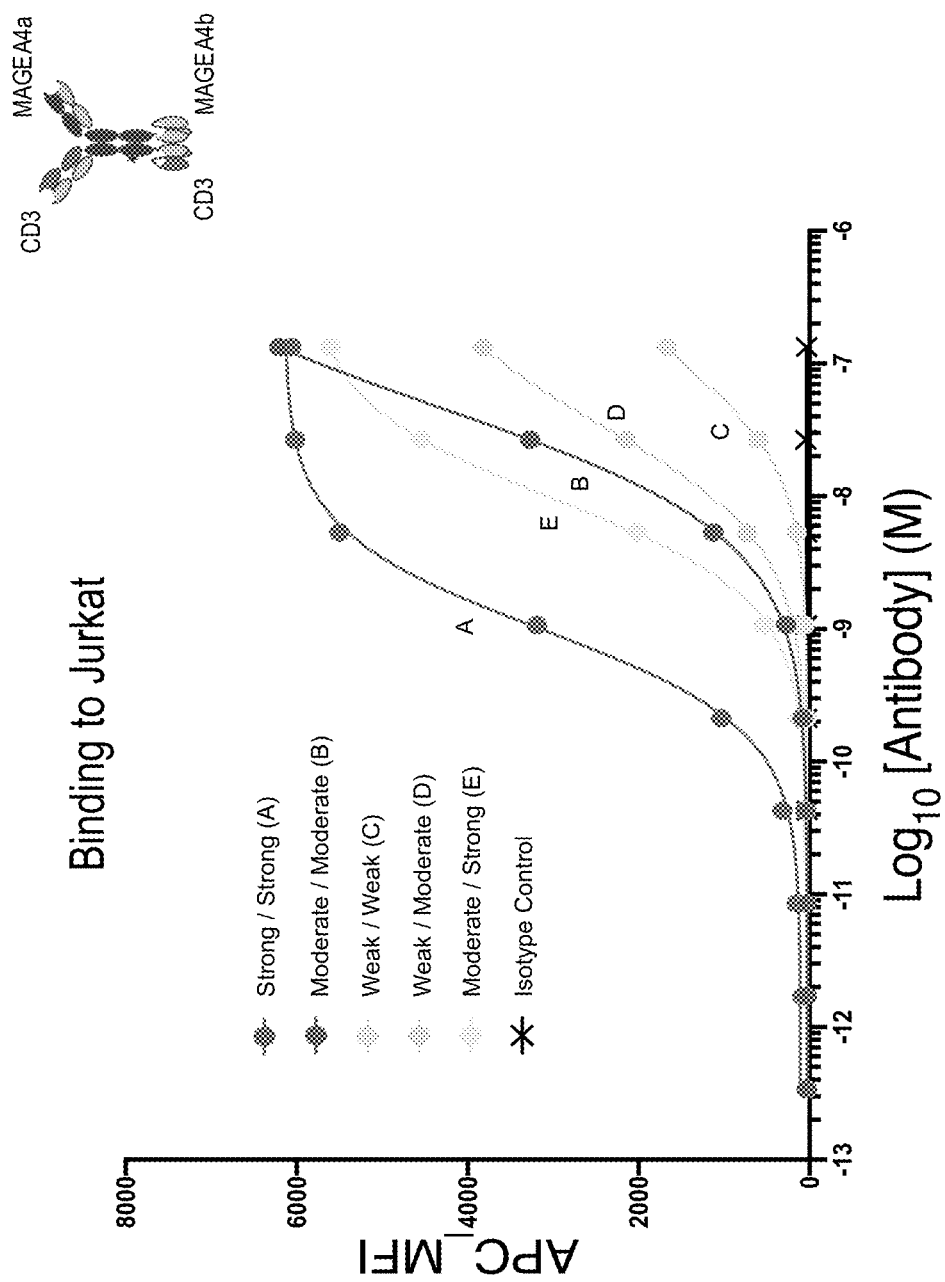
FIG. 13 shows the relative binding affinity for molecules having the structure of FIG. 1F, in which the CD3-binding domains are derived from anti-CD3 antibodies with strong, moderate, or weak binding affinity to CD3. The "strong" binding domains are derived from the 7195P anti-CD3 antibody. The "moderate" binding domains are derived from the 7221G anti-CD3 antibody. The "weak" binding domains are derived from the 7221G20 anti-CD3 antibody. The references to, e.g., "strong/strong" refer, respectively, to the Fab anti-CD3 binding domain and the scFc anti-CD3 binding domain. As expected, binding to CD3-positive Jurkat cells correlates with the strength of the affinity of the anti-CD3 binding domains in the molecules.
Figure 14A:
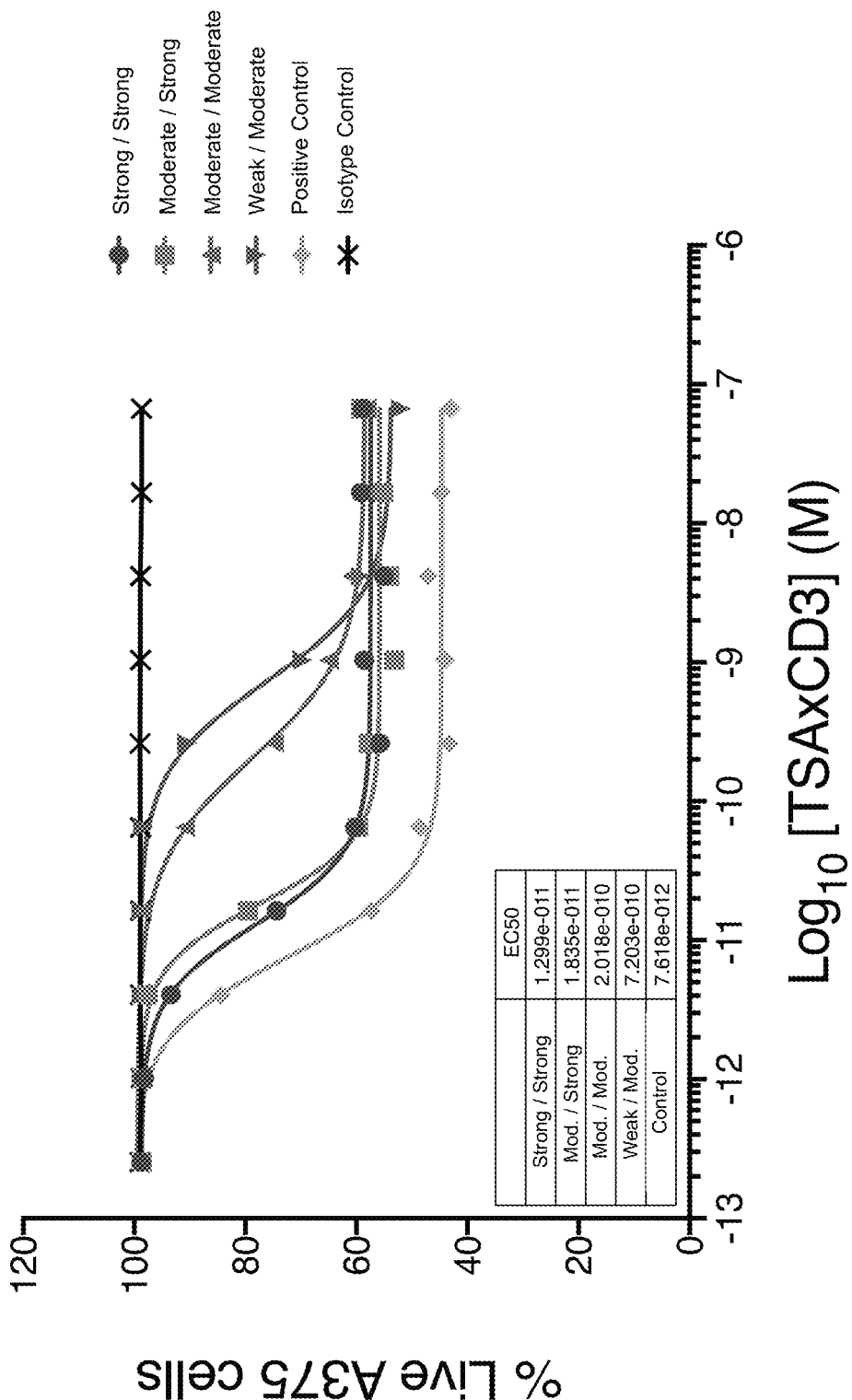
FIGS. 14A and 14B show the relative cytotoxic activity and potency of the molecules shown in FIG. 13 in MAGEA4-positive A375 cells. The molecules were tested individually (FIG. 14A), and in combination with a co-stimulatory bispecific EGFR×CD28 and an anti-PD-1 antibody (FIG. 14B), as discussed in Example 8. There is a clear correlation between the strength of the anti-CD3 binding domains and the potency of the molecules. The "Control" is a positive control that targets the scaffold of all HLA molecules to provide a maximum cytotoxicity against which to compare the other molecules.
Figure 14B:
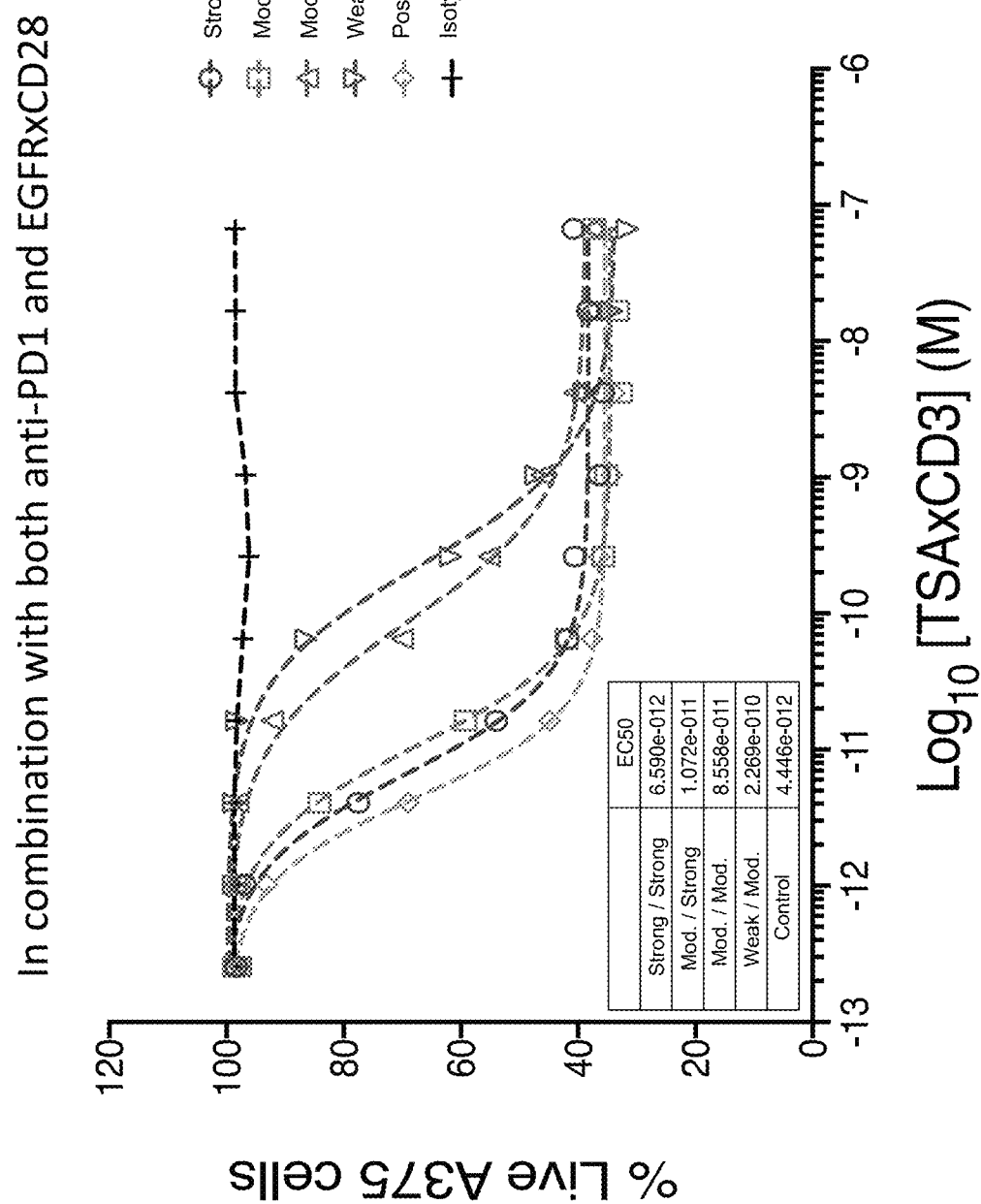
Figure 15A:
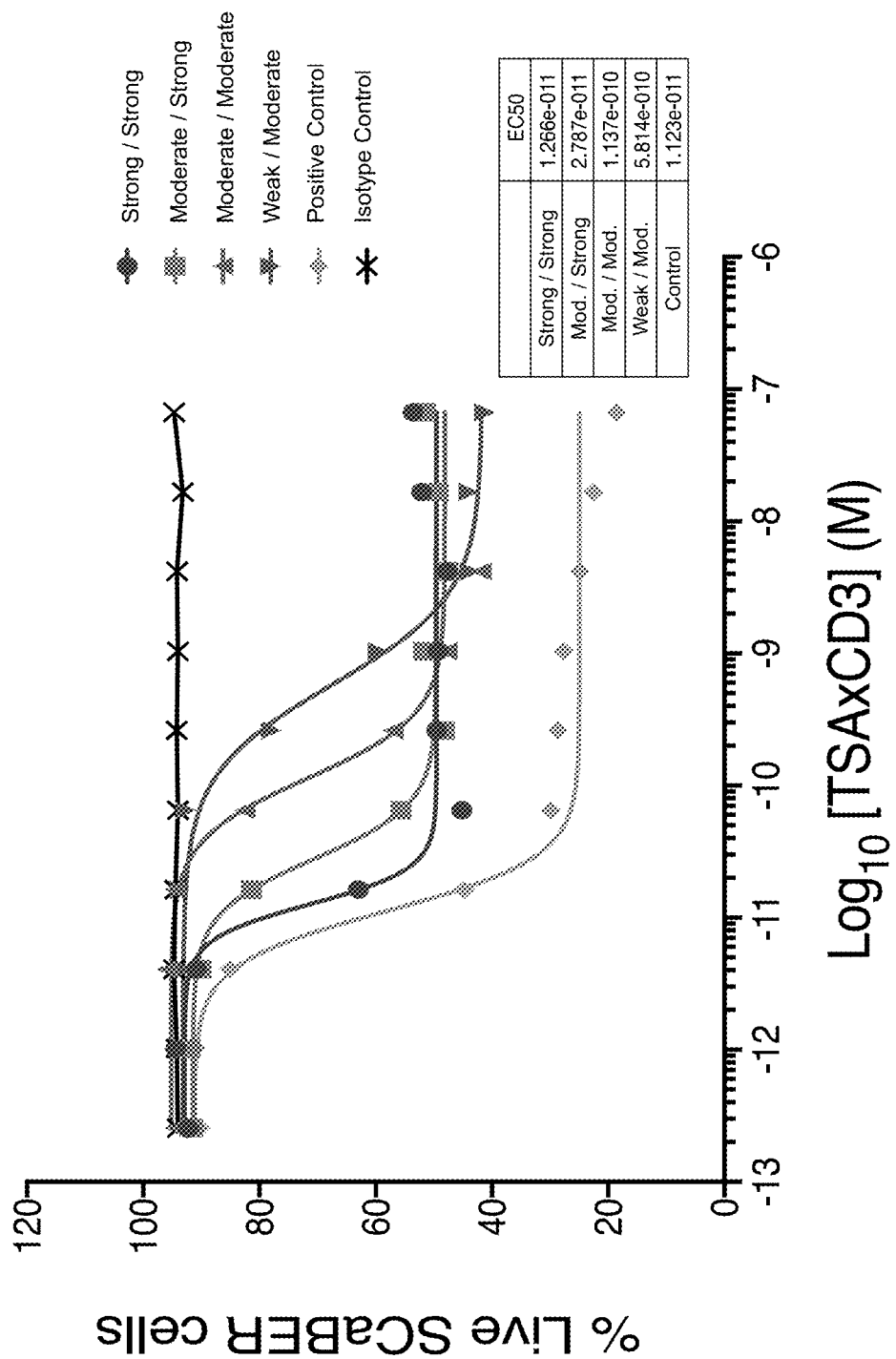
FIGS. 15A and 15B show the relative cytotoxic activity and potency of the molecules shown in FIG. 13 in MAGEA4-positive ScaBER cells. The molecules were tested individually (FIG. 15A), and in combination with a co-stimulatory bispecific EGFR×CD28 and an anti-PD-1 antibody (FIG. 15B), as discussed in Example 8. There is a clear correlation between the strength of the anti-CD3 binding domains and the potency of the molecules. The "Control" is a positive control that targets the scaffold of all HLA molecules to provide a maximum cytotoxicity against which to compare the other molecules.
Figure 15B:
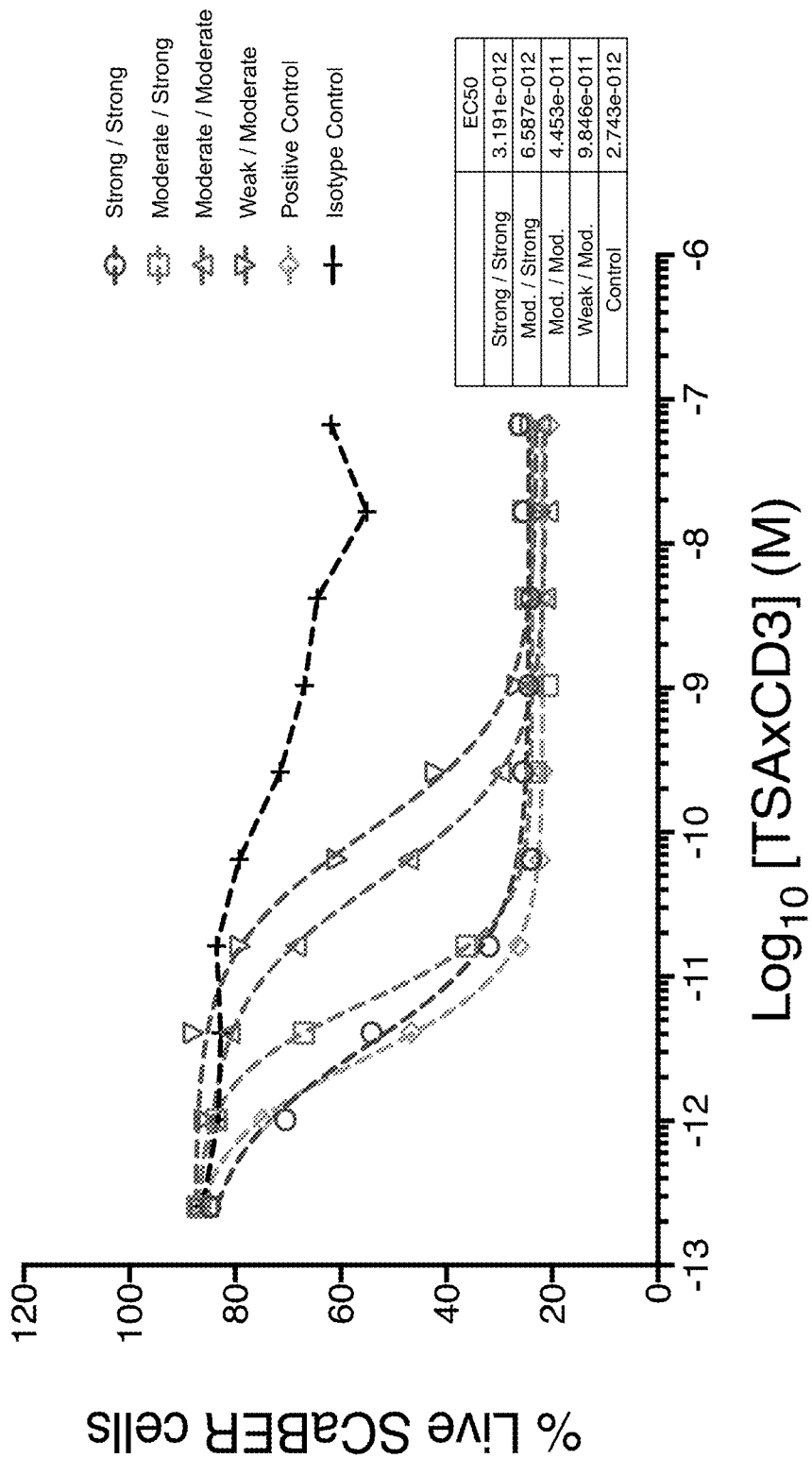

Example 8: Relative Cytotoxicity of Multispecific Molecules Correlates to the Affinity of the T-Cell Antigen Binding Domain Exemplary multispecific molecules having the structure of FIG. 1F (as shown in FIG. 13) were prepared with anti-CD3 binding domains of varying affinity. Five molecules were prepared according to the following parameters:
Molecule A with CD3 arms 7195P (strong) fab and 7195P (strong) scfv;
Molecule B with CD3 arms 7221G (moderate) fab and 7221G (moderate) scfv;
Molecule C with CD3 arms 7221G20 (weak) fab and 7221G20 (weak) scfv;
Molecule D with CD3 arms 7221G20 (weak) fab and 7221G (moderate) scfv; and
Molecule E with CD3 arms 7221G (moderate) fab and 7195P (strong) scfv.

The range of binding titration to T cells from these five molecules was tested by flow cytometry, and correlates with the strength of the CD3 binding domains, as shown in FIG. 13 relative to an isotype control.

In a cytotoxicity assay targeting two different MAGEA4+ cell lines (A375 and ScaBER), the potency of the molecules was shown to decrease when the strength of the effector arm (e.g., anti-CD3 binding domain) decreases, as single agent, or in combination with an EGFRxCD28 bispecific antibody and an anti-PD1 antibody, as shown in FIGS. 14A, 14B, 15A and 15B. Each of the molecules contained the same target antigen binding domains (to non-overlapping MAGEA4 peptide 1 and MAGEA4 peptide 2).

Example 9: Relative Cytotoxicity of Multispecific Molecules Targeting Two Antigens Relative to Conventional Formats Alone or in Combination with an Anti-PD-1 Antibody and a Co-Stimulatory Bispecific Antibody Cytotoxicity of three exemplary multispecific molecules of the present invention (FIG. 1C and FIG. 1F structures) was measured as discussed above, and compared to the cytotoxicity of a conventionally formatted molecule (FIG. 1A), alone or in combination with an anti-PD-1 antibody and a co-stimulatory bispecific EGFRxCD28 antibody. This example uses a positive control with the structure of FIG. 1A that binds CD3 and HLA. The CD3 antigen-binding domains used in this example have a strong binding affinity to human CD3 (derived from 7195P), and the target antigen-binding domains are to one or two non-overlapping MAGEA4 (Melanoma-Associated Antigen A4) peptides (MAGEA4Aa and MAGEA4b) or to a peptide of NY-ESO-1 (New York esophageal squamous cell carcinoma 1). Two isotype negative controls (FIG. 1A format and FIG. 1C format) comprising irrelevant target antigen binding domains were also included.

Figure 16A:
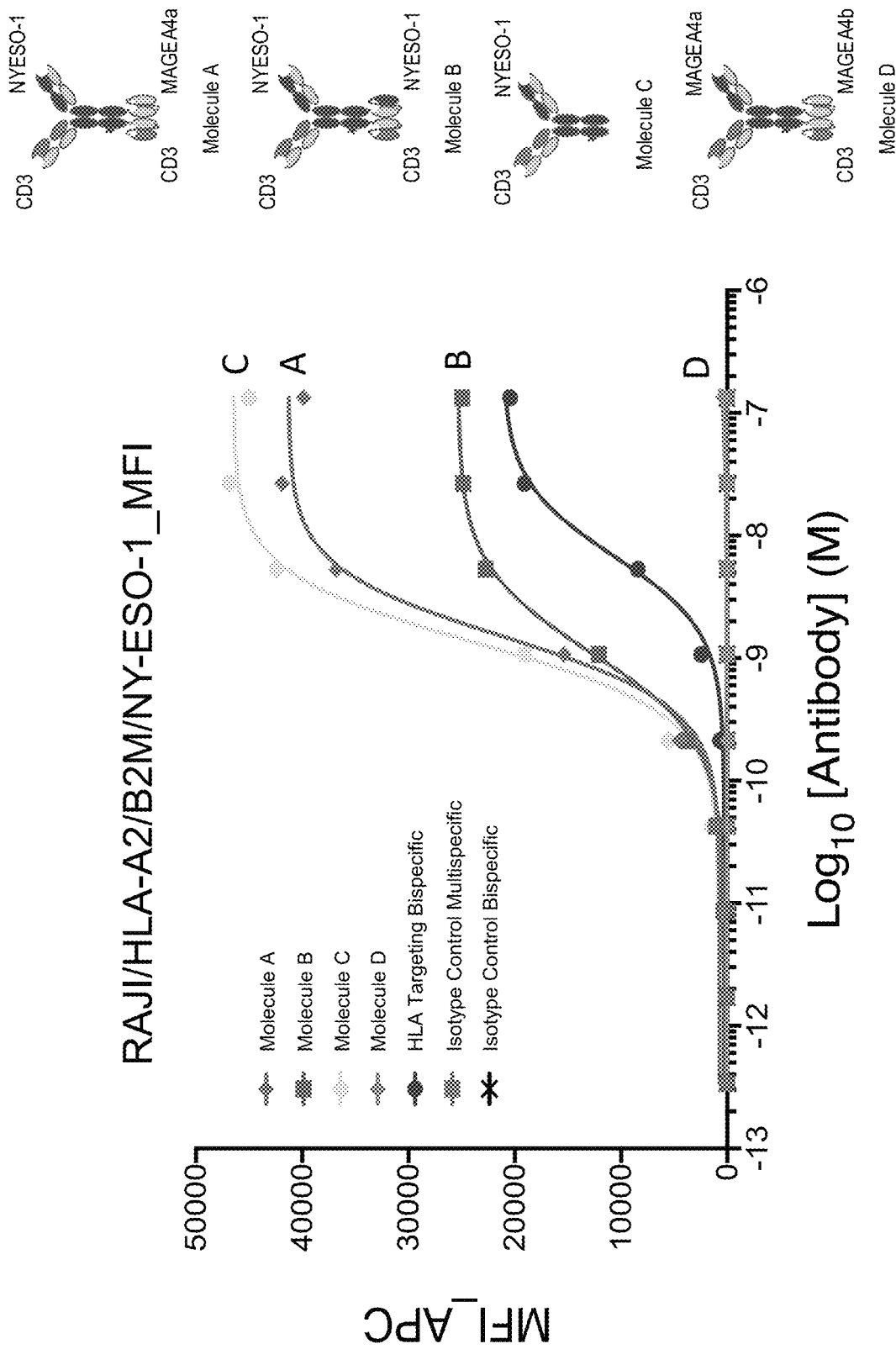

As illustrated in FIGS. 16A, 16B and 16C, the molecules bound, as expected, to NY-ESO-1, MAGEA4a, or MAGEA4b expressing cells by flow cytometry.

Figures 17A, 17B:
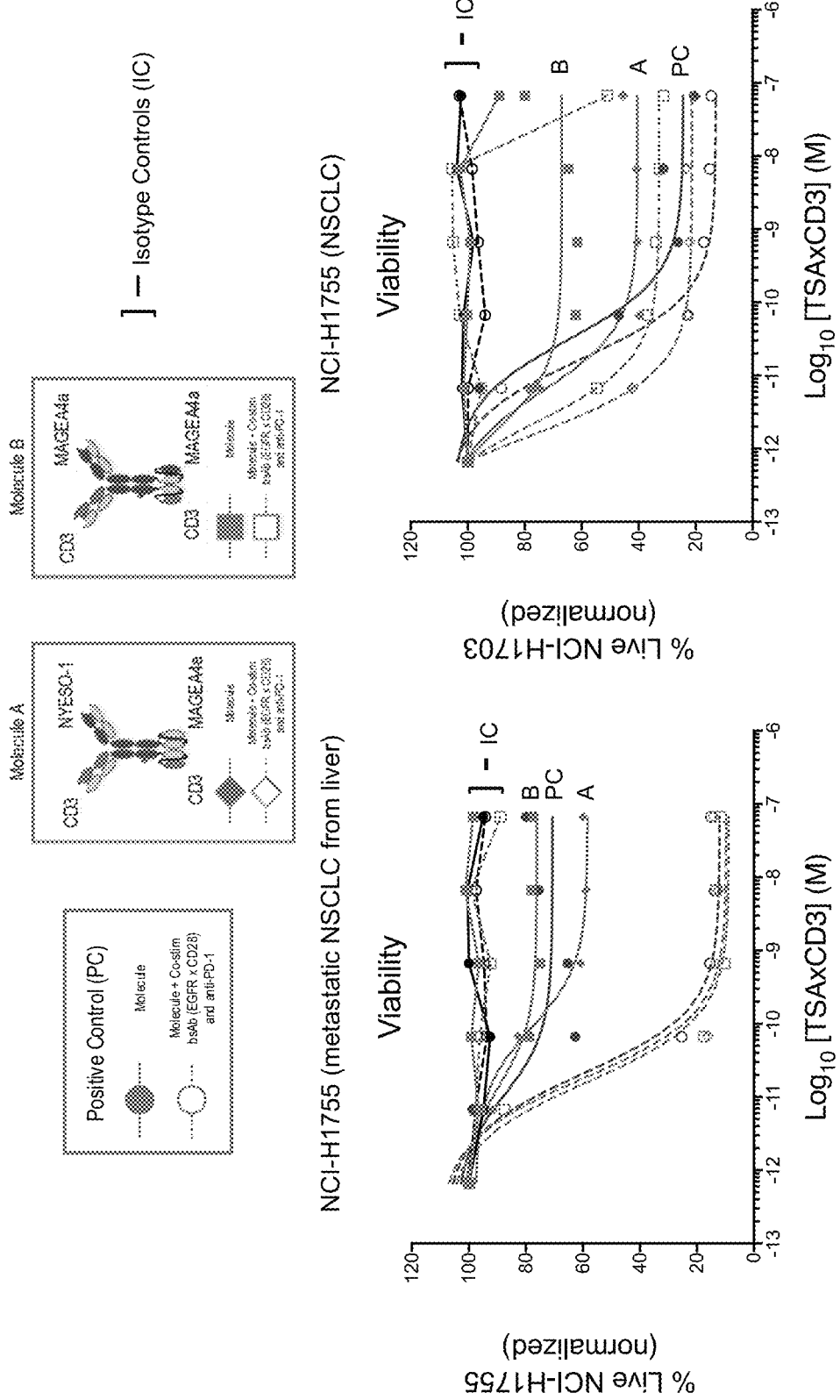
FIGS. 17A and 17B show the relative cytotoxic activity and potency of molecules having the structures of FIG. 1C and FIG. 1F, respectively, as compared to a positive control having the structure of FIG. 1A, which binds HLA molecules and CD3. The isotype controls included a molecule with the structure of FIG. 1C with binding domains to an irrelevant target antigen, and a molecule with the structure of FIG. 1A with binding domains to CD3 and an irrelevant target antigen. The molecules were tested individually, and in combination with a co-stimulatory bispecific EGFR× CD28 antibody and an anti-PD-1 antibody, as discussed in Example 9. The CD3-binding domains of the molecules comprise the variable regions of a 7195P anti-CD3 antibody. The molecule having the structure of FIG. 1F targets two different antigens (NYESO-1 and MAGEA4) with the two TA antigen-binding domains, whereas the molecule having the structure of FIG. 1C targets a single antigen with both of the two TA antigen-binding domains. The molecule having the structure of FIG. 1F and targeting two different antigens was more potent than the molecule having the structure of FIG. 1C. In each case, the combination of these molecules with the co-stimulatory bispecific antibody and the anti-PD-1 antibody produced even greater cytotoxic potency, relative to the molecule alone, similar to the results shown in FIGS. 4A-4C.
Figures 17C, 17D:
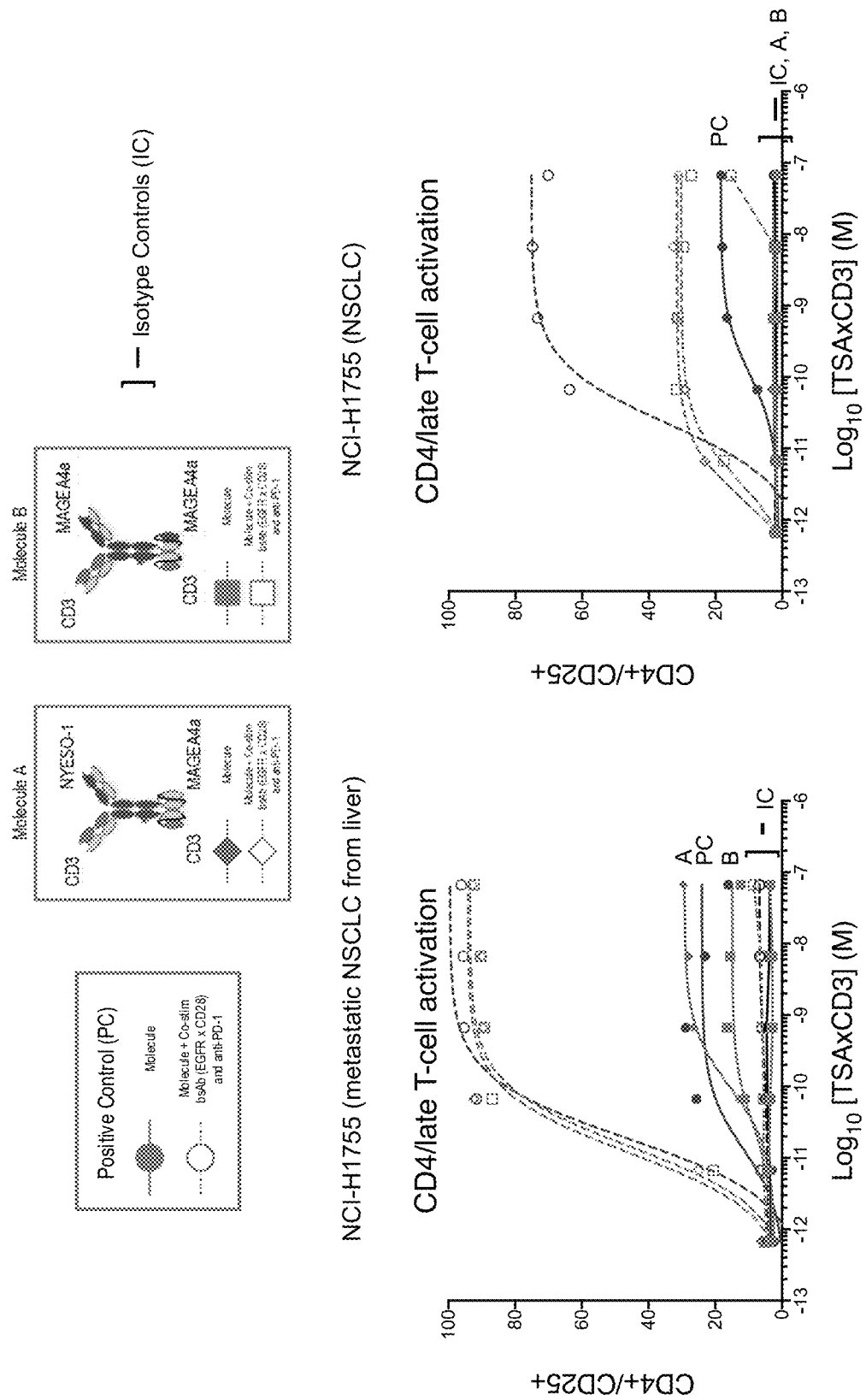
FIGS. 17C and 17D shown the relative T-cell activation of the molecules discussed in connection with FIGS. 17A and 17B.

As illustrated in FIGS. 17A and 17B, the multispecific molecules targeting two distinct antigens (Molecule A) or two different epitopes of a single antigen (Molecule B) potently induced cytotoxicity of both metastatic non-small cell lung cancer (NSCLC) cells (FIG. 17A) and NSCLC cells (FIG. 17B), with the multispecific molecule targeting two distinct antigens (Molecule A) showing increased potency relative to the multispecific molecule targeting two distinct epitopes of the same antigen (Molecule B). The addition of an anti-PD-1 antibody and a co-stimulatory bispecific EGFRxCD28 antibody further enhanced the potency of the exemplary multispecific molecules of the present invention (FIG. 1F structures). The relative induction of T-cell activation of these molecules was also evaluated, and is shown in FIGS. 17C (in metastatic NSCLC cells) and 17D (in NSCLC cells).

Figures 18A, 18B:
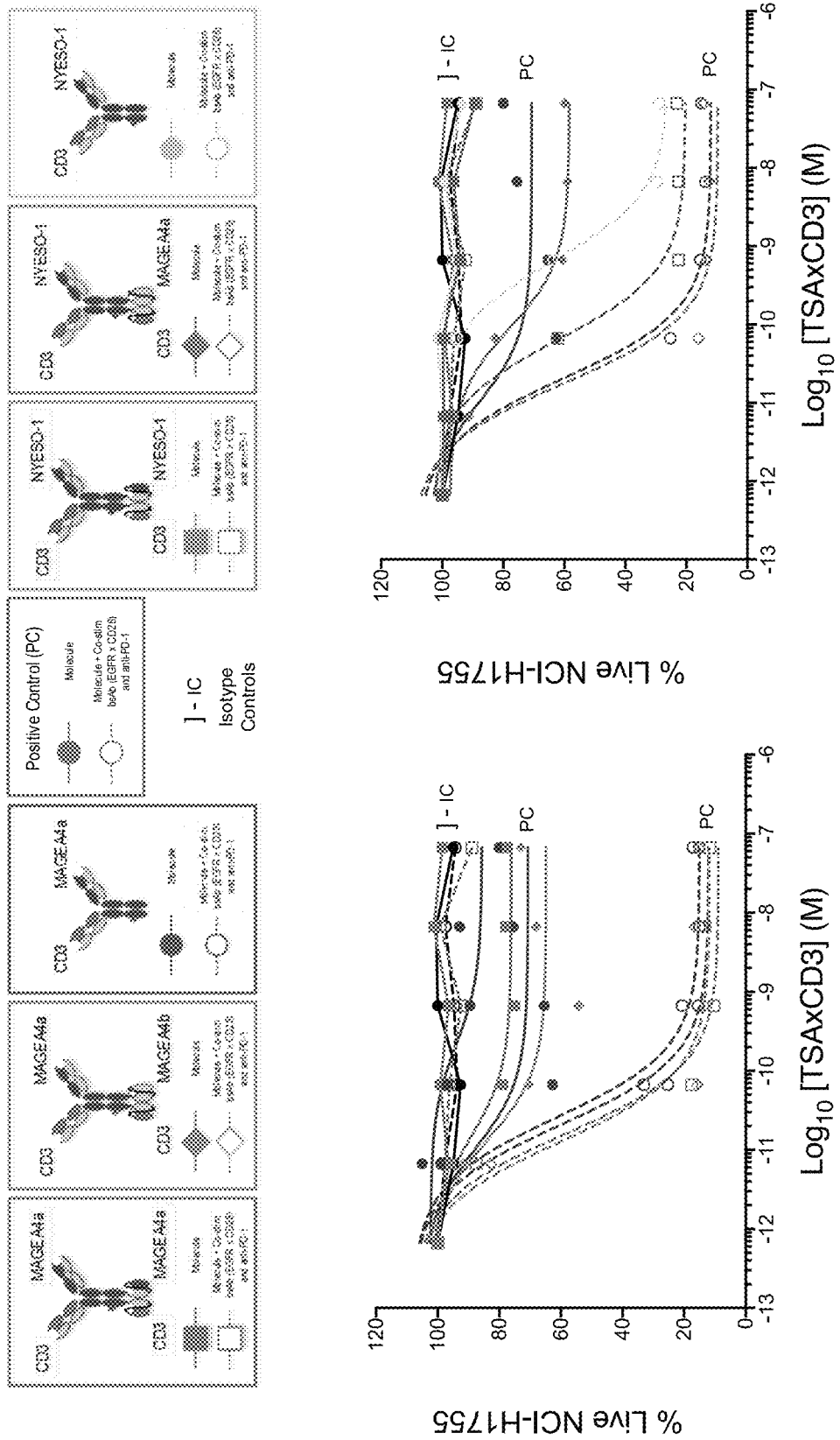
FIGS. 18A and 18B show the relative cytotoxic activity and potency of molecules having the structures of FIG. 1C and FIG. 1F, respectively, as compared to a molecule having the structure of FIG. 1A. The positive control is a molecule with the structure of FIG. 1A that binds human leukocyte antigen (HLA) molecules and CD3. The isotype controls included a molecule with the structure of FIG. 1C with binding domains to an irrelevant target antigen, and a molecule with the structure of FIG. 1A with binding domains to CD3 and an irrelevant target antigen. The molecules were tested individually, and in combination with a co-stimulatory bispecific EGFR×CD28 antibody and an anti-PD-1 antibody, as discussed in Example 9. The CD3-binding domains of the molecules comprise the variable regions of a 7195P anti-CD3 antibody.

The relative cytotoxic activity and potency of multispecific molecules targeting one or two antigens (distinct epitopes or distinct antigens), and having the structures of FIGS. 1C and 1F, was compared to the cytotoxicity of a conventionally formatted molecule (FIG. 1A), alone or in combination with an anti-PD-1 antibody and a co-stimulatory bispecific EGFRxCD28 antibody. The positive control and the isotype controls were as discussed above in this Example. As illustrated in FIGS. 18A and 18B, the multispecific molecules were more potent than the conventionally formatted molecules, and the multispecific molecules targeting two distinct epitopes (FIG. 18A) or two distinct antigens (FIG. 18B) were more potent than the multispecific molecules targeting the same antigen at both target antigen-binding domains. The relative induction of T-cell activation of these molecules is shown in FIGS. 18C, 18D, 18E and 18F.

Example 10: Relative Cytotoxicity of Multispecific Molecule Targeting Two Antigens Relative to a Combination of Conventionally Formatted Molecules Targeting the Same Antigens Cytotoxicity of an exemplary multispecific molecule of the present invention (FIG. 1F structure) targeting two different antigens was measured as discussed above, and compared to the cytotoxicity of a combination of conventionally formatted molecules (FIG. 1A structure) targeting the same two antigens, alone or in combination with an anti-PD-1 antibody and a co-stimulatory bispecific EGFR×CD28 antibody.

Figure 19A:
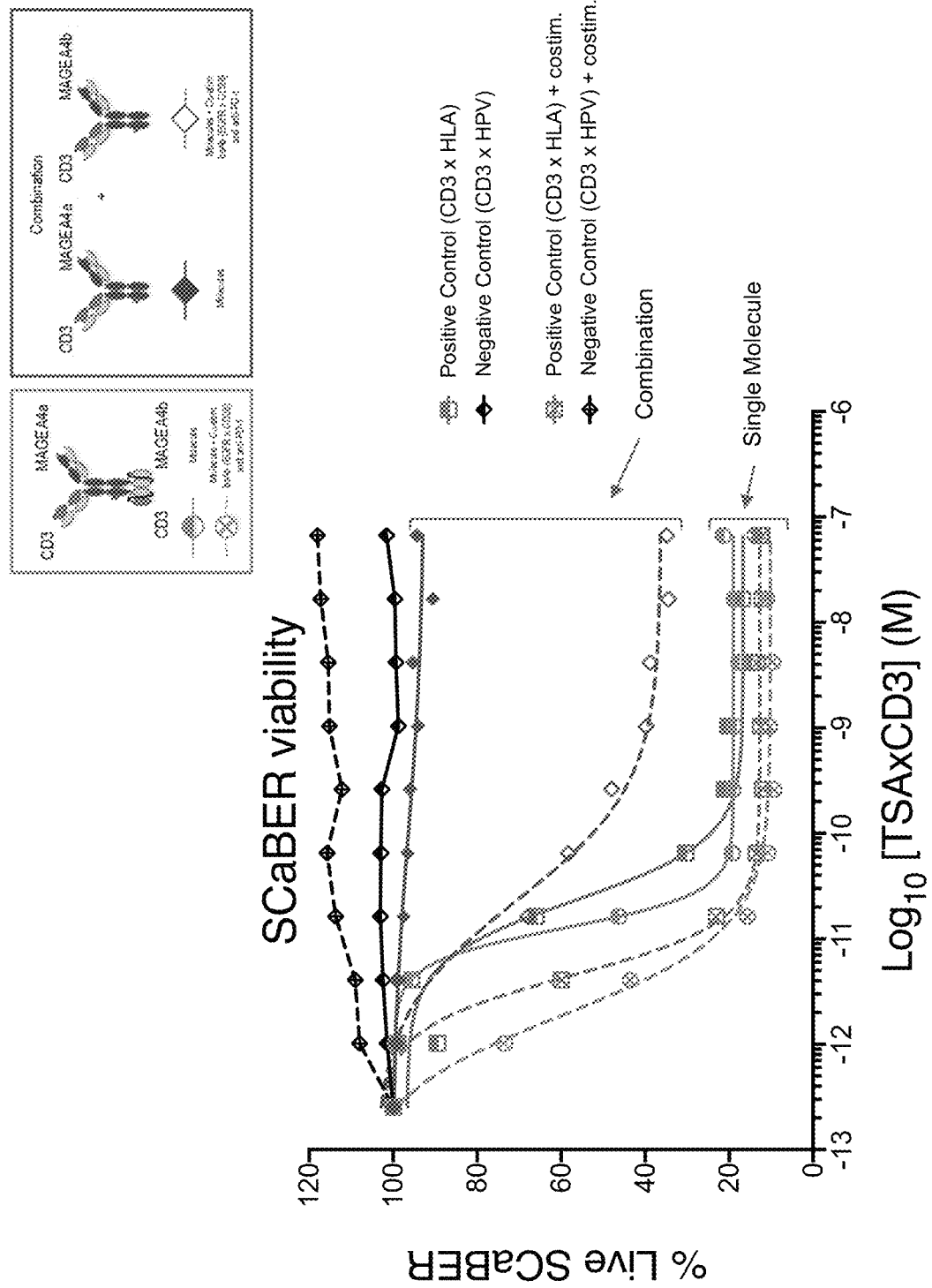
FIGS. 19A and 19B show the cytotoxic activity and potency, and T-cell activation, respectively, of a molecule having the structure of FIG. 1F relative to a combination of two molecules having the structure of FIG. 1A, in which the combination of the two molecules binds the same pair of target antigens as the molecule having the structure of FIG. 1F.
Figure 19B:
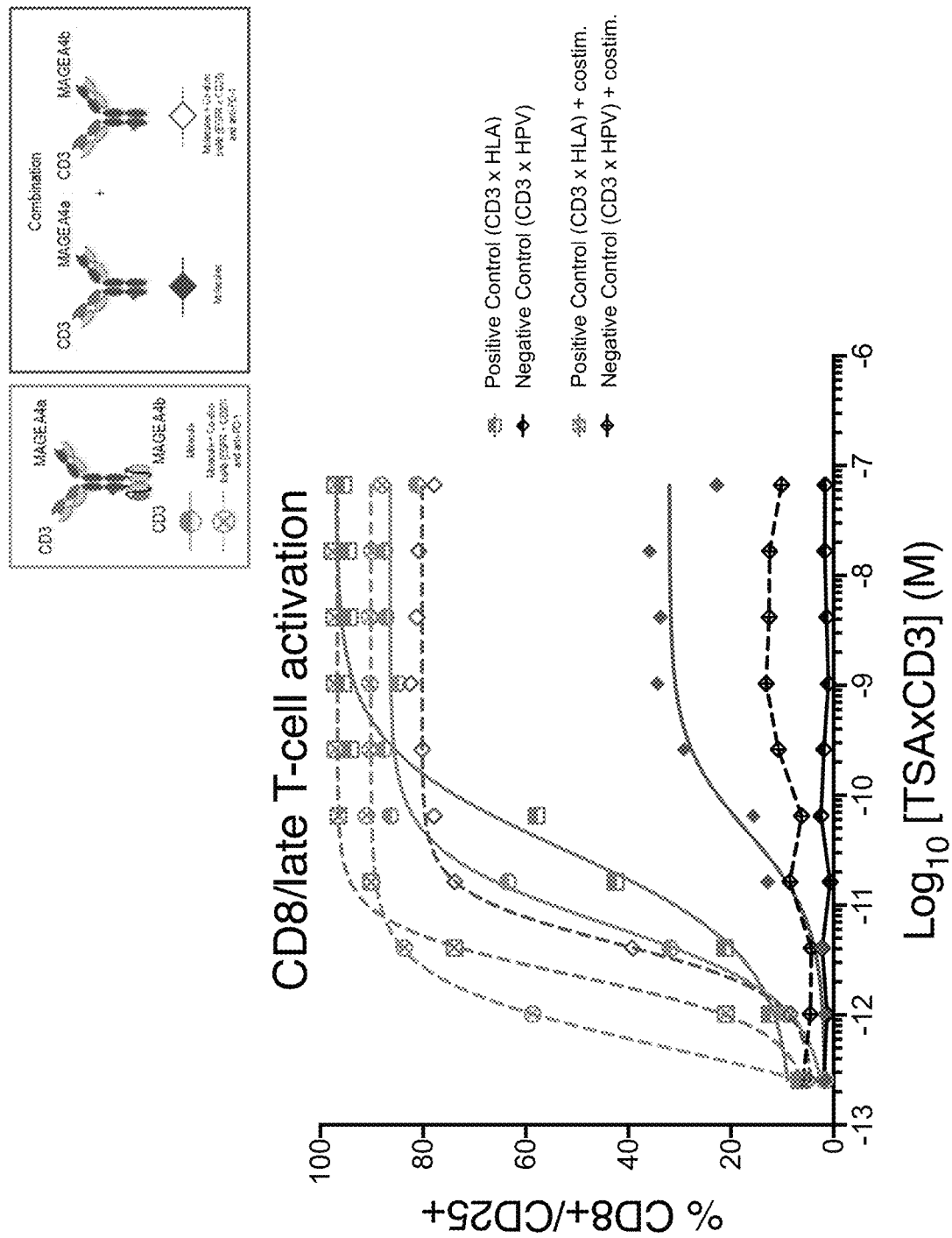

The cytotoxicity assay targeted MAGEA4 expressing-SCaBER cells (Bladder), and demonstrated that the multispecific molecule targeting both MAGEA4a and MAGEA4b (which are non-overlapping peptides of MAGEA4) was more potent than the combination of conventionally-formatted bispecific antibodies targeting the same two MAGEA4 peptides, as shown in FIG. 19A. The addition of an anti-PD-1 antibody and a co-stimulatory bispecific EGFR×CD28 antibody further enhanced the potency of the exemplary multispecific molecule of the present invention (FIG. 1F structure). The relative induction of T-cell activation by these same molecules is shown in FIG. 19B.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

What is claimed is:

1. A method of treating an infection, comprising administering to a subject in need thereof, a multispecific antigen-binding molecule, comprising:
   (a) a first polypeptide comprising, from N-terminus to C-terminus (i) a first antigen-binding domain that specifically binds human CD3, wherein the first antigen-binding domain comprises an immunoglobulin Fab domain comprising a heavy chain variable region (HCVR) and a heavy chain CH1 domain paired with a light chain variable region (LCVR) and a light chain CL domain; (ii) a first multimerizing domain comprising an immunoglobulin Fc domain; and (iii) a second antigen-binding domain that specifically binds human CD3, wherein the second antigen-binding domain is a single chain variable fragment (scFv) domain comprising a HCVR and a LCVR connected by a peptide linker; and
   (b) a second polypeptide comprising, from N-terminus to C-terminus (i) a third antigen-binding domain that specifically binds an infection-associated antigen, wherein the third antigen-binding domain comprises an immunoglobulin Fab domain comprising a HCVR and a heavy chain CH1 domain paired with a LCVR and a light chain CL domain; (ii) a second multimerizing domain comprising an immunoglobulin Fc domain; and (iii) a fourth antigen-binding domain that specifically binds an infection-associated antigen, wherein the fourth antigen-binding domain is a scFv domain comprising a HCVR and a LCVR connected by a peptide linker,
   wherein the first and the second multimerizing domains associate with one another to form the molecule.

2. The method of claim 1, wherein the peptide linker is from 10 to 30 amino acids.

3. The method of claim 1, wherein the peptide linker is a (G4S)$_n$ linker, wherein n is from 1 to 10, selected from the group consisting of SEQ ID NOs: 171, 172, 173, 174, 175, 176, 177, 178, 179, and 180.

4. The method of claim 1, wherein the scFv domains comprise a HCVR comprising a cysteine mutation at residue 44 according to Kabat numbering, and a LCVR comprising a cysteine mutation at residue 100 according to Kabat numbering.

5. The method of claim 1, wherein the scFv domains are connected to the C-terminus of the first and second multimerizing domains, respectively, via a linker of from 5 to 25 amino acids.

6. The method of claim 1, wherein the scFv domains are connected to the C-terminus of the first and second multimerizing domains, respectively, via a linker of from 10 to 30 amino acids.

7. The method of claim 1, wherein the scFv domains are connected to the C-terminus of the first and second multimerizing domains, respectively, via a (G4S)$_n$ linker, wherein n is 1-10, selected from the group consisting of SEQ ID NOs: 171, 172, 173, 174, 175, 176, 177, 178, 179, and 180.

8. The method of claim 7, wherein the linker is a (G4S)$_3$ linker consisting of the amino acid sequence of SEQ ID NO: 173.

9. The method of claim 3, wherein the peptide linker is a (G4S)$_4$ linker consisting of the amino acid sequence of SEQ ID NO: 174.

10. The method of claim 1, wherein each antigen-binding domain that specifically binds human CD3 comprises a HCVR comprising an amino acid sequence selected from the group consisting of SEQ ID NO: 2, SEQ ID NO: 34, SEQ ID NO: 138, SEQ ID NO: 154.

11. The method of claim 1, wherein the first and second multimerizing domains associate with one another via disulfide bonding.

12. The method of claim 1, wherein the first multimerizing domain and the second multimerizing domain are human IgG1 or human IgG4 Fc domains.

13. The method of claim 1, wherein the first multimerizing domain or the second multimerizing domain, but not both the first multimerizing domain and the second multimerizing domain, comprises an amino acid substitution that reduces affinity for Protein A binding compared to a wild-type Fc domain of the same isotype.

14. The method of claim 13, wherein the amino acid substitution comprises an H435R modification according to EU numbering, or H435R and Y436F modifications according to EU numbering.

15. The method of claim 14, wherein the first multimerizing domain comprises the H435R and Y436F modifications.

16. The method of claim 1, wherein the first polypeptide, the second polypeptide, or both the first and the second polypeptides comprise a modified hinge domain that reduces binding affinity for an Fcγ receptor relative to a wild-type hinge domain of the same isotype.

17. The method of claim 1, wherein the infection-associated antigen is a peptide complexed with a major histocompatibility complex (MHC) protein.

18. The method of claim 1, wherein the infection-associated antigen is present at a density of from 100 to 5000 copies per target cell.

19. The method of claim 1, wherein the infection-associated antigen is present at a density of from 1000 to 20,000 copies per target cell.

20. The method of claim 1, wherein the molecule is administered in combination with a second therapeutic agent comprising a bispecific antigen-binding molecule comprising a first antigen-binding domain that binds a target antigen (TA) and a second antigen-binding domain that binds a T-cell antigen.

21. The method of claim 20, wherein the second therapeutic agent comprises a bispecific anti-TA×anti-CD28 antibody.

22. The method of claim 21, wherein the second therapeutic agent comprises a bispecific anti-EGFR×anti-CD28 antibody.

23. The method of claim 1, wherein the molecule is administered in combination with a second therapeutic agent comprising an antibody that binds a check-point inhibitor on a T cell.

24. The method of claim 23, wherein the second therapeutic agent comprises an anti-PD-1 antibody.

25. The method of claim 1, wherein the infection is a viral infection and the infection-associated antigen is a viral antigen.

26. The method of claim 1, wherein the infection is a bacterial infection and the infection-associated antigen is a bacterial antigen.

27. The method of claim 1, wherein the infection is a fungal infection and the infection-associated antigen is a fungal antigen.

28. The method of claim 1, wherein the infection is a parasite infection and the infection-associated antigen is an antigen expressed by a parasite.

* * * * *

SEQUENCE LISTING

<160> NUMBER OF SEQ ID NOS: 180

<210> SEQ ID NO 1
<211> LENGTH: 372
<212> TYPE: DNA
<213> ORGANISM: Artificial Sequence
<220> FEATURE:
<223> OTHER INFORMATION: synthetic

<400> SEQUENCE: 1
gaagtacagc ttgtagaatc cggcggagga ctggtacaac ctggaagaag tcttagactg    60
agttgcgcag ctagtgggtt tacattcgac gattacagca tgcattgggt gaggcaagct   120
cctggtaaag gattggaatg ggttagcggg atatcatgga actcaggaag caagggatac   180
gccgacagcg tgaaaggccg atttacaata tctagggaca acgcaaaaaa ctctctctac   240
cttcaaatga actctcttag ggcagaagac acagcattgt attattgcgc aaaatacggc   300
agtggttatg gcaagtttta tcattatgga ctggacgtgt ggggacaagg gacaacagtg   360
acagtgagta gc                                                       372

<210> SEQ ID NO 2
<211> LENGTH: 124
<212> TYPE: PRT
<213> ORGANISM: Artificial Sequence
<220> FEATURE:
<223> OTHER INFORMATION: synthetic

<400> SEQUENCE: 2

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ser Met His Trp Val Arg Gln Ala Pro Gly Lys Gly Leu Glu Trp Val
        35                  40                  45

Ser Gly Ile Ser Trp Asn Ser Gly Ser Lys Gly Tyr Ala Asp Ser Val
    50                  55                  60

Lys Gly Arg Phe Thr Ile Ser Arg Asp Asn Ala Lys Asn Ser Leu Tyr
65                  70                  75                  80

```
Leu Gln Met Asn Ser Leu Arg Ala Glu Asp Thr Ala Leu Tyr Tyr Cys
                85                  90                  95

Ala Lys Tyr Gly Ser Gly Tyr Gly Lys Phe Tyr His Tyr Gly Leu Asp
            100                 105                 110

Val Trp Gly Gln Gly Thr Thr Val Thr Val Ser Ser
        115                 120

<210> SEQ ID NO 3
<211> LENGTH: 24
<212> TYPE: DNA
<213> ORGANISM: Artificial Sequence
<220> FEATURE:
<223> OTHER INFORMATION: synthetic

<400> SEQUENCE: 3
gggtttacat tcgacgatta cagc                                          24

<210> SEQ ID NO 4
<211> LENGTH: 8
<212> TYPE: PRT
<213> ORGANISM: Artificial Sequence
<220> FEATURE:
<223> OTHER INFORMATION: synthetic

<400> SEQUENCE: 4

Gly Phe Thr Phe Asp Asp Tyr Ser
1               5

<210> SEQ ID NO 5
<211> LENGTH: 24
<212> TYPE: DNA
<213> ORGANISM: Artificial Sequence
<220> FEATURE:
<223> OTHER INFORMATION: synthetic

<400> SEQUENCE: 5
atatcatgga actcaggaag caag                                          24

<210> SEQ ID NO 6
<211> LENGTH: 8
<212> TYPE: PRT
<213> ORGANISM: Artificial Sequence
<220> FEATURE:
<223> OTHER INFORMATION: synthetic

<400> SEQUENCE: 6

Ile Ser Trp Asn Ser Gly Ser Lys
1               5

<210> SEQ ID NO 7
<211> LENGTH: 51
<212> TYPE: DNA
<213> ORGANISM: Artificial Sequence
<220> FEATURE:
<223> OTHER INFORMATION: synthetic

<400> SEQUENCE: 7
gcaaaatacg gcagtggtta tggcaagttt tatcattatg gactggacgt g            51

<210> SEQ ID NO 8
<211> LENGTH: 17
<212> TYPE: PRT
<213> ORGANISM: Artificial Sequence
<220> FEATURE:
<223> OTHER INFORMATION: synthetic
```

-continued

<400> SEQUENCE: 8

Ala Lys Tyr Gly Ser Gly Tyr Gly Lys Phe Tyr His Tyr Gly Leu Asp
1               5                   10                  15
Val

<210> SEQ ID NO 9
<211> LENGTH: 372
<212> TYPE: DNA
<213> ORGANISM: Artificial Sequence
<220> FEATURE:
<223> OTHER INFORMATION: synthetic

<400> SEQUENCE: 9
gaagtacagt tggtagaatc tggaggagga ctcgtgcaac caggacgatc attgcggttg      60
agttgtgctg ctagtggatt cacattcgac gactatgcta tgcattgggt aagacaggct     120
ccaggaaaag gactcgaatg ggtgtcagga ataagttgga actccggaag cattgggtac     180
gcagattcag tcaaagggcg attcaccata tcccgagata cgctaagaa ctcactttac      240 cttcaaatga actctcttcg agcagaggac actgcacttt attattgcgc taaggacggc     300
tccggttatg gatatttta ttattatgga atggacgtat ggggacaagg cactactgtt      360
accgttagtt cc                                                         372

<210> SEQ ID NO 10
<211> LENGTH: 124
<212> TYPE: PRT
<213> ORGANISM: Artificial Sequence
<220> FEATURE:
<223> OTHER INFORMATION: synthetic

<400> SEQUENCE: 10

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Gly Ser Gly Tyr Gly Tyr Phe Tyr Tyr Tyr Gly Met Asp
            100                 105                 110

Val Trp Gly Gln Gly Thr Thr Val Thr Val Ser Ser
        115                 120

<210> SEQ ID NO 11
<211> LENGTH: 24
<212> TYPE: DNA
<213> ORGANISM: Artificial Sequence
<220> FEATURE:
<223> OTHER INFORMATION: synthetic

<400> SEQUENCE: 11
ggattcacat tcgacgacta tgct                                             24

```
<210> SEQ ID NO 12
<211> LENGTH: 8
<212> TYPE: PRT
<213> ORGANISM: Artificial Sequence
<220> FEATURE:
<223> OTHER INFORMATION: synthetic

<400> SEQUENCE: 12

Gly Phe Thr Phe Asp Asp Tyr Ala
1               5

<210> SEQ ID NO 13
<211> LENGTH: 24
<212> TYPE: DNA
<213> ORGANISM: Artificial Sequence
<220> FEATURE:
<223> OTHER INFORMATION: synthetic

<400> SEQUENCE: 13
ataagttgga actccggaag catt                                         24

<210> SEQ ID NO 14
<211> LENGTH: 8
<212> TYPE: PRT
<213> ORGANISM: Artificial Sequence
<220> FEATURE:
<223> OTHER INFORMATION: synthetic

<400> SEQUENCE: 14

Ile Ser Trp Asn Ser Gly Ser Ile
1               5

<210> SEQ ID NO 15
<211> LENGTH: 51
<212> TYPE: DNA
<213> ORGANISM: Artificial Sequence
<220> FEATURE:
<223> OTHER INFORMATION: synthetic

<400> SEQUENCE: 15
gctaaggacg gctccggtta tggatatttt tattattatg gaatggacgt a           51

<210> SEQ ID NO 16
<211> LENGTH: 17
<212> TYPE: PRT
<213> ORGANISM: Artificial Sequence
<220> FEATURE:
<223> OTHER INFORMATION: synthetic

<400> SEQUENCE: 16

Ala Lys Asp Gly Ser Gly Tyr Gly Tyr Phe Tyr Tyr Tyr Gly Met Asp
1               5                   10                  15
Val

<210> SEQ ID NO 17
<211> LENGTH: 372
<212> TYPE: DNA
<213> ORGANISM: Artificial Sequence
<220> FEATURE:
<223> OTHER INFORMATION: synthetic

<400> SEQUENCE: 17
gaagtacaac tggtcgaatc tggaggaggt cttgttcaac tggtcgatc acttcgcctt    60 tcttgtgccg cttctggttt cactttcgac gattatagca tgcattgggt acgacaggct  120
cccggaaaag ggctggaatg ggtgtcagga attagttgga actcaggaag tattggatac  180
```

```
gctgattcag tcaaaggacg cttcacaatc tcaagggaca acgctaaaaa ctcactttat    240
ttgcaaatga actctctccg cgctgaagat accgctctct attattgcgc caaagatggg    300
tctggttacg gttattttta ctactatgga atggacgttt ggggccaagg aacaactgtc    360
acagtatcat cc                                                        372
```

```
<210> SEQ ID NO 18
<211> LENGTH: 124
<212> TYPE: PRT
<213> ORGANISM: Artificial Sequence
<220> FEATURE:
<223> OTHER INFORMATION: synthetic

<400> SEQUENCE: 18
```

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ser Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Gly Ser Gly Tyr Gly Tyr Phe Tyr Tyr Tyr Gly Met Asp
            100                 105                 110

Val Trp Gly Gln Gly Thr Thr Val Thr Val Ser Ser
        115                 120

```
<210> SEQ ID NO 19
<211> LENGTH: 24
<212> TYPE: DNA
<213> ORGANISM: Artificial Sequence
<220> FEATURE:
<223> OTHER INFORMATION: synthetic

<400> SEQUENCE: 19
ggtttcactt tcgacgatta tagc                                            24

<210> SEQ ID NO 20
<211> LENGTH: 8
<212> TYPE: PRT
<213> ORGANISM: Artificial Sequence
<220> FEATURE:
<223> OTHER INFORMATION: synthetic

<400> SEQUENCE: 20
```

Gly Phe Thr Phe Asp Asp Tyr Ser
1               5

```
<210> SEQ ID NO 21
<211> LENGTH: 24
<212> TYPE: DNA
<213> ORGANISM: Artificial Sequence
<220> FEATURE:
<223> OTHER INFORMATION: synthetic

<400> SEQUENCE: 21
attagttgga actcaggaag tatt                                            24
```

<210> SEQ ID NO 22
<211> LENGTH: 8
<212> TYPE: PRT
<213> ORGANISM: Artificial Sequence
<220> FEATURE:
<223> OTHER INFORMATION: synthetic

<400> SEQUENCE: 22

Ile Ser Trp Asn Ser Gly Ser Ile
1               5

<210> SEQ ID NO 23
<211> LENGTH: 51
<212> TYPE: DNA
<213> ORGANISM: Artificial Sequence
<220> FEATURE:
<223> OTHER INFORMATION: synthetic

<400> SEQUENCE: 23
gccaaagatg ggtctggtta cggttatttt tactactatg gaatggacgt t         51

<210> SEQ ID NO 24
<211> LENGTH: 17
<212> TYPE: PRT
<213> ORGANISM: Artificial Sequence
<220> FEATURE:
<223> OTHER INFORMATION: synthetic

<400> SEQUENCE: 24

Ala Lys Asp Gly Ser Gly Tyr Gly Tyr Phe Tyr Tyr Tyr Gly Met Asp
1               5                   10                  15

Val

<210> SEQ ID NO 25
<211> LENGTH: 372
<212> TYPE: DNA
<213> ORGANISM: Artificial Sequence
<220> FEATURE:
<223> OTHER INFORMATION: synthetic

<400> SEQUENCE: 25
gaagttcaac ttgtggaaag tggcggagga ttggttcaac caggacgttc attgaggctt     60
tcatgcgcag cttccggatt tacatttgac gattacgcaa tgcactgggt tagacaggca    120
ccaggaaaag gactggagtg ggtgagcggg atttcatgga acagcggcag tatcggttat    180
gcagactcag ttaaaggaag attcaccatc agtagagaca cgcaaaaaa ttcccttttat    240 ctccaaatga actctcttag ggccgaagat acagcattgt actactgcgc aaaagacgga    300
tcaggttacg gaaaatttta ctactatggt atggatgtat ggggtcaggg aaccacagta    360
actgtatcaa gc                                                        372

<210> SEQ ID NO 26
<211> LENGTH: 124
<212> TYPE: PRT
<213> ORGANISM: Artificial Sequence
<220> FEATURE:
<223> OTHER INFORMATION: synthetic

<400> SEQUENCE: 26

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Gly Ser Gly Tyr Gly Lys Phe Tyr Tyr Tyr Gly Met Asp
            100                 105                 110

Val Trp Gly Gln Gly Thr Thr Val Thr Val Ser Ser
        115                 120

<210> SEQ ID NO 27
<211> LENGTH: 24
<212> TYPE: DNA
<213> ORGANISM: Artificial Sequence
<220> FEATURE:
<223> OTHER INFORMATION: synthetic

<400> SEQUENCE: 27
ggatttacat ttgacgatta cgca                                           24

<210> SEQ ID NO 28
<211> LENGTH: 8
<212> TYPE: PRT
<213> ORGANISM: Artificial Sequence
<220> FEATURE:
<223> OTHER INFORMATION: synthetic

<400> SEQUENCE: 28

Gly Phe Thr Phe Asp Asp Tyr Ala
1               5

<210> SEQ ID NO 29
<211> LENGTH: 24
<212> TYPE: DNA
<213> ORGANISM: Artificial Sequence
<220> FEATURE:
<223> OTHER INFORMATION: synthetic

<400> SEQUENCE: 29
atttcatgga acagcggcag tatc                                           24

<210> SEQ ID NO 30
<211> LENGTH: 8
<212> TYPE: PRT
<213> ORGANISM: Artificial Sequence
<220> FEATURE:
<223> OTHER INFORMATION: synthetic

<400> SEQUENCE: 30

Ile Ser Trp Asn Ser Gly Ser Ile
1               5

<210> SEQ ID NO 31
<211> LENGTH: 51
<212> TYPE: DNA
<213> ORGANISM: Artificial Sequence
<220> FEATURE:
<223> OTHER INFORMATION: synthetic

<400> SEQUENCE: 31
gcaaaagacg gatcaggtta cggaaaattt tactactatg gtatggatgt a    51

<210> SEQ ID NO 32
<211> LENGTH: 17
<212> TYPE: PRT
<213> ORGANISM: Artificial Sequence
<220> FEATURE:
<223> OTHER INFORMATION: synthetic

<400> SEQUENCE: 32

Ala Lys Asp Gly Ser Gly Tyr Gly Lys Phe Tyr Tyr Tyr Gly Met Asp
1               5                   10                  15
Val

<210> SEQ ID NO 33
<211> LENGTH: 372
<212> TYPE: DNA
<213> ORGANISM: Artificial Sequence
<220> FEATURE:
<223> OTHER INFORMATION: synthetic

<400> SEQUENCE: 33
gaagtgcaac tcgttgaaag cggaggagga ctggtccagc ccggcagatc tctcagattg    60
tcttgcgctg catccggatt tacatttgac gactattcaa tgcactgggt acggcaagcc   120
ccaggtaaag gactcgaatg ggtaagcggc atatcttgga actcaggcag tattggctac   180
gcagattcag taaaggaag attcactatt tcaaggata atgctaagaa cagtctctac   240
ttgcaaatga atagcttgcg cgcagaagat acagcacttt attattgtgc aaaagatgga   300
agcggttatg gaaatttta ttattatggt atggatgtat ggggtcaagg tacaacagtt   360
actgtgtcaa gt                                                       372

<210> SEQ ID NO 34
<211> LENGTH: 124
<212> TYPE: PRT
<213> ORGANISM: Artificial Sequence
<220> FEATURE:
<223> OTHER INFORMATION: synthetic

<400> SEQUENCE: 34

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ser Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Gly Ser Gly Tyr Gly Lys Phe Tyr Tyr Tyr Gly Met Asp
            100                 105                 110

Val Trp Gly Gln Gly Thr Thr Val Thr Val Ser Ser
        115                 120

```
<210> SEQ ID NO 35
<211> LENGTH: 24
<212> TYPE: DNA
<213> ORGANISM: Artificial Sequence
<220> FEATURE:
<223> OTHER INFORMATION: synthetic

<400> SEQUENCE: 35
ggatttacat ttgacgacta ttca                                          24

<210> SEQ ID NO 36
<211> LENGTH: 8
<212> TYPE: PRT
<213> ORGANISM: Artificial Sequence
<220> FEATURE:
<223> OTHER INFORMATION: synthetic

<400> SEQUENCE: 36

Gly Phe Thr Phe Asp Asp Tyr Ser
1               5

<210> SEQ ID NO 37
<211> LENGTH: 24
<212> TYPE: DNA
<213> ORGANISM: Artificial Sequence
<220> FEATURE:
<223> OTHER INFORMATION: synthetic

<400> SEQUENCE: 37
atatcttgga actcaggcag tatt                                          24

<210> SEQ ID NO 38
<211> LENGTH: 8
<212> TYPE: PRT
<213> ORGANISM: Artificial Sequence
<220> FEATURE:
<223> OTHER INFORMATION: synthetic

<400> SEQUENCE: 38

Ile Ser Trp Asn Ser Gly Ser Ile
1               5

<210> SEQ ID NO 39
<211> LENGTH: 51
<212> TYPE: DNA
<213> ORGANISM: Artificial Sequence
<220> FEATURE:
<223> OTHER INFORMATION: synthetic

<400> SEQUENCE: 39
gcaaaagatg gaagcggtta tgggaaattt tattattatg gtatggatgt a           51

<210> SEQ ID NO 40
<211> LENGTH: 17
<212> TYPE: PRT
<213> ORGANISM: Artificial Sequence
<220> FEATURE:
<223> OTHER INFORMATION: synthetic

<400> SEQUENCE: 40

Ala Lys Asp Gly Ser Gly Tyr Gly Lys Phe Tyr Tyr Tyr Gly Met Asp
1               5                   10                  15
Val

<210> SEQ ID NO 41
<211> LENGTH: 372
```

```
<212> TYPE: DNA
<213> ORGANISM: Artificial Sequence
<220> FEATURE:
<223> OTHER INFORMATION: synthetic

<400> SEQUENCE: 41
gaagtacagc ttgtagaatc cggcggagga ctggtacaac ctggaagaag tcttagactg      60
agttgcgcag ctagtgggtt tacattcgac gattacagca tgcattgggt gaggcaagct     120
cctggtaaag gattgaatg ggttagcggg atatcatgga actcaggaag catcggatac     180
gccgacagcg tgaaaggccg atttacaata tctagggaca acgcaaaaaa ctctctctac     240
cttcaaatga actctcttag ggcagaagac acagcattgt attattgcgc aaaatacggc     300
agtggttatg gcaagttta tcattatgga ctggacgtgt ggggacaagg gacaacagtg     360
acagtgagta gc                                                         372

<210> SEQ ID NO 42
<211> LENGTH: 124
<212> TYPE: PRT
<213> ORGANISM: Artificial Sequence
<220> FEATURE:
<223> OTHER INFORMATION: synthetic

<400> SEQUENCE: 42

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ser Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Tyr Gly Ser Gly Tyr Gly Lys Phe Tyr His Tyr Gly Leu Asp
            100                 105                 110

Val Trp Gly Gln Gly Thr Thr Val Thr Val Ser Ser
        115                 120

<210> SEQ ID NO 43
<211> LENGTH: 24
<212> TYPE: DNA
<213> ORGANISM: Artificial Sequence
<220> FEATURE:
<223> OTHER INFORMATION: synthetic

<400> SEQUENCE: 43
gggtttacat tcgacgatta cagc                                             24

<210> SEQ ID NO 44
<211> LENGTH: 8
<212> TYPE: PRT
<213> ORGANISM: Artificial Sequence
<220> FEATURE:
<223> OTHER INFORMATION: synthetic

<400> SEQUENCE: 44

Gly Phe Thr Phe Asp Asp Tyr Ser
1               5
```

<210> SEQ ID NO 45
<211> LENGTH: 24
<212> TYPE: DNA
<213> ORGANISM: Artificial Sequence
<220> FEATURE:
<223> OTHER INFORMATION: synthetic

<400> SEQUENCE: 45
atatcatgga actcaggaag catc              24

<210> SEQ ID NO 46
<211> LENGTH: 8
<212> TYPE: PRT
<213> ORGANISM: Artificial Sequence
<220> FEATURE:
<223> OTHER INFORMATION: synthetic

<400> SEQUENCE: 46

Ile Ser Trp Asn Ser Gly Ser Ile
1               5

<210> SEQ ID NO 47
<211> LENGTH: 51
<212> TYPE: DNA
<213> ORGANISM: Artificial Sequence
<220> FEATURE:
<223> OTHER INFORMATION: synthetic

<400> SEQUENCE: 47
gcaaaatacg gcagtggtta tggcaagttt tatcattatg gactggacgt g        51

<210> SEQ ID NO 48
<211> LENGTH: 17
<212> TYPE: PRT
<213> ORGANISM: Artificial Sequence
<220> FEATURE:
<223> OTHER INFORMATION: synthetic

<400> SEQUENCE: 48

Ala Lys Tyr Gly Ser Gly Tyr Gly Lys Phe Tyr His Tyr Gly Leu Asp
1               5                   10                  15
Val

<210> SEQ ID NO 49
<211> LENGTH: 372
<212> TYPE: DNA
<213> ORGANISM: Artificial Sequence
<220> FEATURE:
<223> OTHER INFORMATION: synthetic

<400> SEQUENCE: 49
gaagtacagc ttgtagaatc cggcggagga ctggtacaac tggaagaag tcttagactg      60 agttgcgcag ctagtgggtt tacattcgac gattacagca tgcattgggt gaggcaagct    120
cctggtaaag gattggaatg ggttagcggg atatcatgga actcaggaag caagggatac    180
gccgacagcg tgaaaggccg atttacaata tctagggaca acgcaaaaaa ctctctctac    240
cttcaaatga actctcttag ggcagaagac acagcattgt attattgcgc aaaagacggc    300
agtggttatg gcaagttttat tcattatgga ctggacgtgt ggggacaagg gacaacagtg    360
acagtgagta gc                                                        372

<210> SEQ ID NO 50

<211> LENGTH: 124
<212> TYPE: PRT
<213> ORGANISM: Artificial Sequence
<220> FEATURE:
<223> OTHER INFORMATION: synthetic

<400> SEQUENCE: 50

Glu Val Gln Leu Val Glu Ser Gly Gly Gly Leu Val Gln Pro Gly Arg
1               5                   10                  15
Ser Leu Arg Leu Ser Cys Ala Ala Ser Gly Phe Thr Phe Asp Asp Tyr
            20                  25                  30
Ser Met His Trp Val Arg Gln Ala Pro Gly Lys Gly Leu Glu Trp Val
        35                  40                  45
Ser Gly Ile Ser Trp Asn Ser Gly Ser Lys Gly Tyr Ala Asp Ser Val
    50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Leu Tyr Tyr Cys
                85                  90                  95
Ala Lys Asp Gly Ser Gly Tyr Gly Lys Phe Tyr His Tyr Gly Leu Asp
            100                 105                 110
Val Trp Gly Gln Gly Thr Thr Val Thr Val Ser Ser
        115                 120

<210> SEQ ID NO 51
<211> LENGTH: 24
<212> TYPE: DNA
<213> ORGANISM: Artificial Sequence
<220> FEATURE:
<223> OTHER INFORMATION: synthetic

<400> SEQUENCE: 51
gggtttacat tcgacgatta cagc                                          24

<210> SEQ ID NO 52
<211> LENGTH: 8
<212> TYPE: PRT
<213> ORGANISM: Artificial Sequence
<220> FEATURE:
<223> OTHER INFORMATION: synthetic

<400> SEQUENCE: 52

Gly Phe Thr Phe Asp Asp Tyr Ser
1               5

<210> SEQ ID NO 53
<211> LENGTH: 24
<212> TYPE: DNA
<213> ORGANISM: Artificial Sequence
<220> FEATURE:
<223> OTHER INFORMATION: synthetic

<400> SEQUENCE: 53
atatcatgga actcaggaag caag                                          24

<210> SEQ ID NO 54
<211> LENGTH: 8
<212> TYPE: PRT
<213> ORGANISM: Artificial Sequence
<220> FEATURE:
<223> OTHER INFORMATION: synthetic

<400> SEQUENCE: 54

Ile Ser Trp Asn Ser Gly Ser Lys
1               5

<210> SEQ ID NO 55
<211> LENGTH: 51
<212> TYPE: DNA
<213> ORGANISM: Artificial Sequence
<220> FEATURE:
<223> OTHER INFORMATION: synthetic

<400> SEQUENCE: 55
gcaaaagacg gcagtggtta tggcaagttt tatcattatg gactggacgt g        51

<210> SEQ ID NO 56
<211> LENGTH: 17
<212> TYPE: PRT
<213> ORGANISM: Artificial Sequence
<220> FEATURE:
<223> OTHER INFORMATION: synthetic

<400> SEQUENCE: 56

Ala Lys Asp Gly Ser Gly Tyr Gly Lys Phe Tyr His Tyr Gly Leu Asp
1               5                   10                  15
Val

<210> SEQ ID NO 57
<211> LENGTH: 372
<212> TYPE: DNA
<213> ORGANISM: Artificial Sequence
<220> FEATURE:
<223> OTHER INFORMATION: synthetic

<400> SEQUENCE: 57
gaagtacagc ttgtagaatc cggcggagga ctggtacaac ctggaagaag tcttagactg      60
agttgcgcag ctagtgggtt tacattcgac gattacagca tgcattgggt gaggcaagct     120
cctggtaaag gattgaatg ggttagcggg atatcatgga actcaggaag caagggatac     180
gccgacagcg tgaaaggccg atttacaata tctagggaca acgcaaaaaa ctctctctac     240
cttcaaatga actctcttag ggcagaagac acagcattgt attattgcgc aaaatacggc     300
agtggttatg gcaagttta ttattatgga ctggacgtgt ggggacaagg gacaacagtg     360
acagtgagta gc                                                        372

<210> SEQ ID NO 58
<211> LENGTH: 124
<212> TYPE: PRT
<213> ORGANISM: Artificial Sequence
<220> FEATURE:
<223> OTHER INFORMATION: synthetic

<400> SEQUENCE: 58

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ser Met His Trp Val Arg Gln Ala Pro Gly Lys Gly Leu Glu Trp Val
        35                  40                  45

Ser Gly Ile Ser Trp Asn Ser Gly Ser Lys Gly Tyr Ala Asp Ser Val
    50                  55                  60

```
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                 85                  90                  95

Ala Lys Tyr Gly Ser Gly Tyr Gly Lys Phe Tyr Tyr Tyr Gly Leu Asp
            100                 105                 110

Val Trp Gly Gln Gly Thr Thr Val Thr Val Ser Ser
        115                 120
```

<210> SEQ ID NO 59
<211> LENGTH: 24
<212> TYPE: DNA
<213> ORGANISM: Artificial Sequence
<220> FEATURE:
<223> OTHER INFORMATION: synthetic

<400> SEQUENCE: 59
gggtttacat tcgacgatta cagc                                24

<210> SEQ ID NO 60
<211> LENGTH: 8
<212> TYPE: PRT
<213> ORGANISM: Artificial Sequence
<220> FEATURE:
<223> OTHER INFORMATION: synthetic

<400> SEQUENCE: 60

```
Gly Phe Thr Phe Asp Asp Tyr Ser
1               5
```

<210> SEQ ID NO 61
<211> LENGTH: 24
<212> TYPE: DNA
<213> ORGANISM: Artificial Sequence
<220> FEATURE:
<223> OTHER INFORMATION: synthetic

<400> SEQUENCE: 61
atatcatgga actcaggaag caag                                24

<210> SEQ ID NO 62
<211> LENGTH: 8
<212> TYPE: PRT
<213> ORGANISM: Artificial Sequence
<220> FEATURE:
<223> OTHER INFORMATION: synthetic

<400> SEQUENCE: 62

```
Ile Ser Trp Asn Ser Gly Ser Lys
1               5
```

<210> SEQ ID NO 63
<211> LENGTH: 51
<212> TYPE: DNA
<213> ORGANISM: Artificial Sequence
<220> FEATURE:
<223> OTHER INFORMATION: synthetic

<400> SEQUENCE: 63
gcaaaatacg gcagtggtta tggcaagttt tattattatg gactggacgt g         51

<210> SEQ ID NO 64
<211> LENGTH: 17
<212> TYPE: PRT
<213> ORGANISM: Artificial Sequence

```
<220> FEATURE:
<223> OTHER INFORMATION: synthetic

<400> SEQUENCE: 64

Ala Lys Tyr Gly Ser Gly Tyr Gly Lys Phe Tyr Tyr Gly Leu Asp
1               5                   10                  15

Val

<210> SEQ ID NO 65
<211> LENGTH: 372
<212> TYPE: DNA
<213> ORGANISM: Artificial Sequence
<220> FEATURE:
<223> OTHER INFORMATION: synthetic

<400> SEQUENCE: 65
gaagtacagc ttgtagaatc cggcggagga ctggtacaac ctggaagaag tcttagactg     60
agttgcgcag ctagtgggtt tacattcgac gattacagca tgcattgggt gaggcaagct    120
cctggtaaag gattggaatg ggttagcggg atatcatgga actcaggaag caagggatac    180
gccgacagcg tgaaaggccg atttacaata tctagggaca cgcaaaaaa ctctctctac     240 cttcaaatga actctcttag gcagaagac acagcattgt attattgcgc aaaatacggc     300
agtggttatg gcaagtttta tcattatgga atggacgtgt ggggacaagg gacaacagtg    360
acagtgagta gc                                                       372

<210> SEQ ID NO 66
<211> LENGTH: 124
<212> TYPE: PRT
<213> ORGANISM: Artificial Sequence
<220> FEATURE:
<223> OTHER INFORMATION: synthetic

<400> SEQUENCE: 66

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ser Met His Trp Val Arg Gln Ala Pro Gly Lys Gly Leu Glu Trp Val
        35                  40                  45

Ser Gly Ile Ser Trp Asn Ser Gly Ser Lys Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Tyr Gly Ser Gly Tyr Gly Lys Phe Tyr His Tyr Gly Met Asp
            100                 105                 110

Val Trp Gly Gln Gly Thr Thr Val Thr Val Ser Ser
        115                 120

<210> SEQ ID NO 67
<211> LENGTH: 24
<212> TYPE: DNA
<213> ORGANISM: Artificial Sequence
<220> FEATURE:
<223> OTHER INFORMATION: synthetic

<400> SEQUENCE: 67
gggtttacat tcgacgatta cagc                                           24
```

<210> SEQ ID NO 68
<211> LENGTH: 8
<212> TYPE: PRT
<213> ORGANISM: Artificial Sequence
<220> FEATURE:
<223> OTHER INFORMATION: synthetic

<400> SEQUENCE: 68

Gly Phe Thr Phe Asp Asp Tyr Ser
1               5

<210> SEQ ID NO 69
<211> LENGTH: 24
<212> TYPE: DNA
<213> ORGANISM: Artificial Sequence
<220> FEATURE:
<223> OTHER INFORMATION: synthetic

<400> SEQUENCE: 69
atatcatgga actcaggaag caag                                          24

<210> SEQ ID NO 70
<211> LENGTH: 8
<212> TYPE: PRT
<213> ORGANISM: Artificial Sequence
<220> FEATURE:
<223> OTHER INFORMATION: synthetic

<400> SEQUENCE: 70

Ile Ser Trp Asn Ser Gly Ser Lys
1               5

<210> SEQ ID NO 71
<211> LENGTH: 51
<212> TYPE: DNA
<213> ORGANISM: Artificial Sequence
<220> FEATURE:
<223> OTHER INFORMATION: synthetic

<400> SEQUENCE: 71
gcaaaatacg gcagtggtta tggcaagttt tatcattatg gaatggacgt g            51

<210> SEQ ID NO 72
<211> LENGTH: 17
<212> TYPE: PRT
<213> ORGANISM: Artificial Sequence
<220> FEATURE:
<223> OTHER INFORMATION: synthetic

<400> SEQUENCE: 72

Ala Lys Tyr Gly Ser Gly Tyr Gly Lys Phe Tyr His Tyr Gly Met Asp
1               5                   10                  15

Val

<210> SEQ ID NO 73
<211> LENGTH: 372
<212> TYPE: DNA
<213> ORGANISM: Artificial Sequence
<220> FEATURE:
<223> OTHER INFORMATION: synthetic

<400> SEQUENCE: 73
gaagtacagc ttgtagaatc cggcggagga ctggtacaac tggaagaag tcttagactg     60 agttgcgcag ctagtgggtt tacattcgac gattacagca tgcattgggt gaggcaagct   120

```
cctggtaaag gattggaatg ggttagcggg atatcatgga actcaggaag catcggatac    180
gccgacagcg tgaaaggccg atttacaata tctagggaca cgcaaaaaa ctctctctac    240 cttcaaatga actctcttag ggcagaagac acagcattgt attattgcgc aaaagacggc    300
agtggttatg gcaagtttta tcattatgga ctggacgtgt ggggacaagg gacaacagtg    360
acagtgagta gc                                                        372
```

```
<210> SEQ ID NO 74
<211> LENGTH: 124
<212> TYPE: PRT
<213> ORGANISM: Artificial Sequence
<220> FEATURE:
<223> OTHER INFORMATION: synthetic

<400> SEQUENCE: 74
```

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ser Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Gly Ser Gly Tyr Gly Lys Phe Tyr His Tyr Gly Leu Asp
            100                 105                 110

Val Trp Gly Gln Gly Thr Thr Val Thr Val Ser Ser
        115                 120

```
<210> SEQ ID NO 75
<211> LENGTH: 24
<212> TYPE: DNA
<213> ORGANISM: Artificial Sequence
<220> FEATURE:
<223> OTHER INFORMATION: synthetic

<400> SEQUENCE: 75
gggtttacat tcgacgatta cagc                                           24
```

```
<210> SEQ ID NO 76
<211> LENGTH: 8
<212> TYPE: PRT
<213> ORGANISM: Artificial Sequence
<220> FEATURE:
<223> OTHER INFORMATION: synthetic

<400> SEQUENCE: 76
```

Gly Phe Thr Phe Asp Asp Tyr Ser
1               5

```
<210> SEQ ID NO 77
<211> LENGTH: 24
<212> TYPE: DNA
<213> ORGANISM: Artificial Sequence
<220> FEATURE:
<223> OTHER INFORMATION: synthetic
```

```
<400> SEQUENCE: 77
atatcatgga actcaggaag catc                                          24

<210> SEQ ID NO 78
<211> LENGTH: 8
<212> TYPE: PRT
<213> ORGANISM: Artificial Sequence
<220> FEATURE:
<223> OTHER INFORMATION: synthetic

<400> SEQUENCE: 78

Ile Ser Trp Asn Ser Gly Ser Ile
1               5

<210> SEQ ID NO 79
<211> LENGTH: 51
<212> TYPE: DNA
<213> ORGANISM: Artificial Sequence
<220> FEATURE:
<223> OTHER INFORMATION: synthetic

<400> SEQUENCE: 79
gcaaaagacg gcagtggtta tggcaagttt tatcattatg gactggacgt g            51

<210> SEQ ID NO 80
<211> LENGTH: 17
<212> TYPE: PRT
<213> ORGANISM: Artificial Sequence
<220> FEATURE:
<223> OTHER INFORMATION: synthetic

<400> SEQUENCE: 80

Ala Lys Asp Gly Ser Gly Tyr Gly Lys Phe Tyr His Tyr Gly Leu Asp
1               5                   10                  15

Val

<210> SEQ ID NO 81
<211> LENGTH: 372
<212> TYPE: DNA
<213> ORGANISM: Artificial Sequence
<220> FEATURE:
<223> OTHER INFORMATION: synthetic

<400> SEQUENCE: 81
gaagtacagc ttgtagaatc cggcggagga ctggtacaac ctggaagaag tcttagactg   60
agttgcgcag ctagtgggtt tacattcgac gattacagca tgcattgggt gaggcaagct  120
cctggtaaag gattggaatg ggttagcggg atatcatgga actcaggaag catcggatac  180
gccgacagcg tgaaaggccg atttacaata tctagggaca cgcaaaaaaa ctctctctac  240
cttcaaatga actctcttag ggcagaagac acagcattgt attattgcgc aaaatacggc  300
agtggttatg gcaagttttta ttattatgga ctggacgtgt ggggacaagg gacaacagtg  360
acagtgagta gc                                                      372

<210> SEQ ID NO 82
<211> LENGTH: 124
<212> TYPE: PRT
<213> ORGANISM: Artificial Sequence
<220> FEATURE:
<223> OTHER INFORMATION: synthetic
```

<400> SEQUENCE: 82

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ser Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Tyr Gly Ser Gly Tyr Gly Lys Phe Tyr Tyr Tyr Gly Leu Asp
            100                 105                 110

Val Trp Gly Gln Gly Thr Thr Val Thr Val Ser Ser
        115                 120

<210> SEQ ID NO 83
<211> LENGTH: 24
<212> TYPE: DNA
<213> ORGANISM: Artificial Sequence
<220> FEATURE:
<223> OTHER INFORMATION: synthetic

<400> SEQUENCE: 83
gggtttacat tcgacgatta cagc                                          24

<210> SEQ ID NO 84
<211> LENGTH: 8
<212> TYPE: PRT
<213> ORGANISM: Artificial Sequence
<220> FEATURE:
<223> OTHER INFORMATION: synthetic

<400> SEQUENCE: 84

Gly Phe Thr Phe Asp Asp Tyr Ser
1               5

<210> SEQ ID NO 85
<211> LENGTH: 24
<212> TYPE: DNA
<213> ORGANISM: Artificial Sequence
<220> FEATURE:
<223> OTHER INFORMATION: synthetic

<400> SEQUENCE: 85
atatcatgga actcaggaag catc                                          24

<210> SEQ ID NO 86
<211> LENGTH: 8
<212> TYPE: PRT
<213> ORGANISM: Artificial Sequence
<220> FEATURE:
<223> OTHER INFORMATION: synthetic

<400> SEQUENCE: 86

Ile Ser Trp Asn Ser Gly Ser Ile
1               5

<210> SEQ ID NO 87

```
<211> LENGTH: 51
<212> TYPE: DNA
<213> ORGANISM: Artificial Sequence
<220> FEATURE:
<223> OTHER INFORMATION: synthetic

<400> SEQUENCE: 87
gcaaaatacg gcagtggtta tggcaagttt tattattatg gactggacgt g        51

<210> SEQ ID NO 88
<211> LENGTH: 17
<212> TYPE: PRT
<213> ORGANISM: Artificial Sequence
<220> FEATURE:
<223> OTHER INFORMATION: synthetic

<400> SEQUENCE: 88
```

Ala Lys Tyr Gly Ser Gly Tyr Gly Lys Phe Tyr Tyr Tyr Gly Leu Asp
1               5                   10                  15

Val

```
<210> SEQ ID NO 89
<211> LENGTH: 372
<212> TYPE: DNA
<213> ORGANISM: Artificial Sequence
<220> FEATURE:
<223> OTHER INFORMATION: synthetic

<400> SEQUENCE: 89
gaagtacagc ttgtagaatc cggcggagga ctggtacaac ctggaagaag tcttagactg    60
agttgcgcag ctagtgggtt tacattcgac gattacagca tgcattgggt gaggcaagct   120
cctggtaaag gattgaatg ggttagcggg atatcatgga actcaggaag catcggatac   180
gccgacagcg tgaaaggccg atttacaata tctagggaca acgcaaaaaa ctctctctac   240
cttcaaatga actctcttag ggcagaagac acagcattgt attattgcgc aaaatacggc   300
agtggttatg gcaagttta tcattatgga atggacgtgt ggggacaagg gacaacagtg   360
acagtgagta gc                                                       372

<210> SEQ ID NO 90
<211> LENGTH: 124
<212> TYPE: PRT
<213> ORGANISM: Artificial Sequence
<220> FEATURE:
<223> OTHER INFORMATION: synthetic

<400> SEQUENCE: 90
```

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ser Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Tyr Gly Ser Gly Tyr Gly Lys Phe Tyr His Tyr Gly Met Asp
            100                 105                 110

Val Trp Gly Gln Gly Thr Thr Val Thr Val Ser Ser
        115                 120

<210> SEQ ID NO 91
<211> LENGTH: 24
<212> TYPE: DNA
<213> ORGANISM: Artificial Sequence
<220> FEATURE:
<223> OTHER INFORMATION: synthetic

<400> SEQUENCE: 91
gggtttacat tcgacgatta cagc                                          24

<210> SEQ ID NO 92
<211> LENGTH: 8
<212> TYPE: PRT
<213> ORGANISM: Artificial Sequence
<220> FEATURE:
<223> OTHER INFORMATION: synthetic

<400> SEQUENCE: 92

Gly Phe Thr Phe Asp Asp Tyr Ser
1               5

<210> SEQ ID NO 93
<211> LENGTH: 24
<212> TYPE: DNA
<213> ORGANISM: Artificial Sequence
<220> FEATURE:
<223> OTHER INFORMATION: synthetic

<400> SEQUENCE: 93
atatcatgga actcaggaag catc                                          24

<210> SEQ ID NO 94
<211> LENGTH: 8
<212> TYPE: PRT
<213> ORGANISM: Artificial Sequence
<220> FEATURE:
<223> OTHER INFORMATION: synthetic

<400> SEQUENCE: 94

Ile Ser Trp Asn Ser Gly Ser Ile
1               5

<210> SEQ ID NO 95
<211> LENGTH: 51
<212> TYPE: DNA
<213> ORGANISM: Artificial Sequence
<220> FEATURE:
<223> OTHER INFORMATION: synthetic

<400> SEQUENCE: 95
gcaaaatacg gcagtggtta tggcaagttt tatcattatg gaatggacgt g            51

<210> SEQ ID NO 96
<211> LENGTH: 17
<212> TYPE: PRT
<213> ORGANISM: Artificial Sequence
<220> FEATURE:
<223> OTHER INFORMATION: synthetic

<400> SEQUENCE: 96

Ala Lys Tyr Gly Ser Gly Tyr Gly Lys Phe Tyr His Tyr Gly Met Asp
1               5                   10                  15
Val

<210> SEQ ID NO 97
<211> LENGTH: 372
<212> TYPE: DNA
<213> ORGANISM: Artificial Sequence
<220> FEATURE:
<223> OTHER INFORMATION: synthetic

<400> SEQUENCE: 97
gaagtacagc ttgtagaatc cggcggagga ctggtacaac ctggaagaag tcttagactg      60
agttgcgcag ctagtgggtt tacattcgac gattacagca tgcattgggt gaggcaagct     120
cctggtaaag gattgaatg ggttagcggg atatcatgga actcaggaag caagggatac      180
gccgacagcg tgaaaggccg atttacaata tctaggaca acgcaaaaaa ctctctctac      240
cttcaaatga actctcttag ggcagaagac acagcattgt attattgcgc aaaagacggc     300
agtggttatg gcaagttta ttattatgga ctggacgtgt ggggacaagg gacaacagtg      360
acagtgagta gc                                                         372

<210> SEQ ID NO 98
<211> LENGTH: 124
<212> TYPE: PRT
<213> ORGANISM: Artificial Sequence
<220> FEATURE:
<223> OTHER INFORMATION: synthetic

<400> SEQUENCE: 98

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ser Met His Trp Val Arg Gln Ala Pro Gly Lys Gly Leu Glu Trp Val
        35                  40                  45

Ser Gly Ile Ser Trp Asn Ser Gly Ser Lys Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
            85                  90                  95

Ala Lys Asp Gly Ser Gly Tyr Gly Lys Phe Tyr Tyr Tyr Gly Leu Asp
            100                 105                 110

Val Trp Gly Gln Gly Thr Thr Val Thr Val Ser Ser
        115                 120

<210> SEQ ID NO 99
<211> LENGTH: 24
<212> TYPE: DNA
<213> ORGANISM: Artificial Sequence
<220> FEATURE:
<223> OTHER INFORMATION: synthetic

<400> SEQUENCE: 99
gggtttacat tcgacgatta cagc                                             24

```
<210> SEQ ID NO 100
<211> LENGTH: 8
<212> TYPE: PRT
<213> ORGANISM: Artificial Sequence
<220> FEATURE:
<223> OTHER INFORMATION: synthetic

<400> SEQUENCE: 100

Gly Phe Thr Phe Asp Asp Tyr Ser
1               5

<210> SEQ ID NO 101
<211> LENGTH: 24
<212> TYPE: DNA
<213> ORGANISM: Artificial Sequence
<220> FEATURE:
<223> OTHER INFORMATION: synthetic

<400> SEQUENCE: 101
atatcatgga actcaggaag caag                                              24

<210> SEQ ID NO 102
<211> LENGTH: 8
<212> TYPE: PRT
<213> ORGANISM: Artificial Sequence
<220> FEATURE:
<223> OTHER INFORMATION: synthetic

<400> SEQUENCE: 102

Ile Ser Trp Asn Ser Gly Ser Lys
1               5

<210> SEQ ID NO 103
<211> LENGTH: 51
<212> TYPE: DNA
<213> ORGANISM: Artificial Sequence
<220> FEATURE:
<223> OTHER INFORMATION: synthetic

<400> SEQUENCE: 103
gcaaaagacg gcagtggtta tggcaagttt tattattatg gactggacgt g               51

<210> SEQ ID NO 104
<211> LENGTH: 17
<212> TYPE: PRT
<213> ORGANISM: Artificial Sequence
<220> FEATURE:
<223> OTHER INFORMATION: synthetic

<400> SEQUENCE: 104

Ala Lys Asp Gly Ser Gly Tyr Gly Lys Phe Tyr Tyr Tyr Gly Leu Asp
1               5                   10                  15

Val

<210> SEQ ID NO 105
<211> LENGTH: 372
<212> TYPE: DNA
<213> ORGANISM: Artificial Sequence
<220> FEATURE:
<223> OTHER INFORMATION: synthetic

<400> SEQUENCE: 105
gaagtacagc ttgtagaatc cggcggagga ctggtacaac tggaagaag tcttagactg        60 agttgcgcag ctagtgggtt tacattcgac gattacagca tgcattgggt gaggcaagct      120
cctggtaaag gattggaatg ggttagcggg atatcatgga actcaggaag caagggatac      180
```

```
gccgacagcg tgaaaggccg atttacaata tctagggaca acgcaaaaaa ctctctctac    240
cttcaaatga actctcttag ggcagaagac acagcattgt attattgcgc aaaagacggc    300
agtggttatg caagttttta tcattatgga atggacgtgt ggggacaagg gacaacagtg    360
acagtgagta gc                                                        372
```

```
<210> SEQ ID NO 106
<211> LENGTH: 124
<212> TYPE: PRT
<213> ORGANISM: Artificial Sequence
<220> FEATURE:
<223> OTHER INFORMATION: synthetic

<400> SEQUENCE: 106
```

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ser Met His Trp Val Arg Gln Ala Pro Gly Lys Gly Leu Glu Trp Val
        35                  40                  45

Ser Gly Ile Ser Trp Asn Ser Gly Ser Lys Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Gly Ser Gly Tyr Gly Lys Phe Tyr His Tyr Gly Met Asp
            100                 105                 110

Val Trp Gly Gln Gly Thr Thr Val Thr Val Ser Ser
        115                 120

```
<210> SEQ ID NO 107
<211> LENGTH: 24
<212> TYPE: DNA
<213> ORGANISM: Artificial Sequence
<220> FEATURE:
<223> OTHER INFORMATION: synthetic

<400> SEQUENCE: 107
gggtttacat tcgacgatta cagc                                            24

<210> SEQ ID NO 108
<211> LENGTH: 8
<212> TYPE: PRT
<213> ORGANISM: Artificial Sequence
<220> FEATURE:
<223> OTHER INFORMATION: synthetic

<400> SEQUENCE: 108
```

Gly Phe Thr Phe Asp Asp Tyr Ser
1               5

```
<210> SEQ ID NO 109
<211> LENGTH: 24
<212> TYPE: DNA
<213> ORGANISM: Artificial Sequence
<220> FEATURE:
<223> OTHER INFORMATION: synthetic

<400> SEQUENCE: 109
atatcatgga actcaggaag caag                                            24
```

<210> SEQ ID NO 110
<211> LENGTH: 8
<212> TYPE: PRT
<213> ORGANISM: Artificial Sequence
<220> FEATURE:
<223> OTHER INFORMATION: synthetic

<400> SEQUENCE: 110

Ile Ser Trp Asn Ser Gly Ser Lys
1               5

<210> SEQ ID NO 111
<211> LENGTH: 51
<212> TYPE: DNA
<213> ORGANISM: Artificial Sequence
<220> FEATURE:
<223> OTHER INFORMATION: synthetic

<400> SEQUENCE: 111
gcaaaagacg gcagtggtta tggcaagttt tatcattatg gaatggacgt g        51

<210> SEQ ID NO 112
<211> LENGTH: 17
<212> TYPE: PRT
<213> ORGANISM: Artificial Sequence
<220> FEATURE:
<223> OTHER INFORMATION: synthetic

<400> SEQUENCE: 112

Ala Lys Asp Gly Ser Gly Tyr Gly Lys Phe Tyr His Tyr Gly Met Asp
1               5                   10                  15

Val

<210> SEQ ID NO 113
<211> LENGTH: 372
<212> TYPE: DNA
<213> ORGANISM: Artificial Sequence
<220> FEATURE:
<223> OTHER INFORMATION: synthetic

<400> SEQUENCE: 113
gaagtacagc ttgtagaatc cggcggagga ctggtacaac ctggaagaag tcttagactg      60
agttgcgcag ctagtgggtt tacattcgac gattacagca tgcattgggt gaggcaagct     120
cctggtaaag gattggaatg ggttagcggg atatcatgga actcaggaag caagggatac     180
gccgacagcg tgaaaggccg atttacaata tctaggggaca acgcaaaaaa ctctctctac     240
cttcaaatga actctcttag ggcagaagac acagcattgt attattgcgc aaaatacggc     300
agtggttatg gcaagtttta ttattatgga atggacgtgt ggggacaagg gacaacagtg     360
acagtgagta gc                                                          372

<210> SEQ ID NO 114
<211> LENGTH: 124
<212> TYPE: PRT
<213> ORGANISM: Artificial Sequence
<220> FEATURE:
<223> OTHER INFORMATION: synthetic

<400> SEQUENCE: 114

Glu Val Gln Leu Val Glu Ser Gly Gly Gly Leu Val Gln Pro Gly Arg
1               5                   10                  15

```
Ser Leu Arg Leu Ser Cys Ala Ala Ser Gly Phe Thr Phe Asp Asp Tyr
            20                  25                  30

Ser Met His Trp Val Arg Gln Ala Pro Gly Lys Gly Leu Glu Trp Val
        35                  40                  45

Ser Gly Ile Ser Trp Asn Ser Gly Ser Lys Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Tyr Gly Ser Gly Tyr Gly Lys Phe Tyr Tyr Tyr Gly Met Asp
            100                 105                 110

Val Trp Gly Gln Gly Thr Thr Val Thr Val Ser Ser
        115                 120
```

<210> SEQ ID NO 115
<211> LENGTH: 24
<212> TYPE: DNA
<213> ORGANISM: Artificial Sequence
<220> FEATURE:
<223> OTHER INFORMATION: synthetic

<400> SEQUENCE: 115
gggtttacat tcgacgatta cagc    24

<210> SEQ ID NO 116
<211> LENGTH: 8
<212> TYPE: PRT
<213> ORGANISM: Artificial Sequence
<220> FEATURE:
<223> OTHER INFORMATION: synthetic

<400> SEQUENCE: 116

```
Gly Phe Thr Phe Asp Asp Tyr Ser
1               5
```

<210> SEQ ID NO 117
<211> LENGTH: 24
<212> TYPE: DNA
<213> ORGANISM: Artificial Sequence
<220> FEATURE:
<223> OTHER INFORMATION: synthetic

<400> SEQUENCE: 117
atatcatgga actcaggaag caag    24

<210> SEQ ID NO 118
<211> LENGTH: 8
<212> TYPE: PRT
<213> ORGANISM: Artificial Sequence
<220> FEATURE:
<223> OTHER INFORMATION: synthetic

<400> SEQUENCE: 118

```
Ile Ser Trp Asn Ser Gly Ser Lys
1               5
```

<210> SEQ ID NO 119
<211> LENGTH: 51
<212> TYPE: DNA
<213> ORGANISM: Artificial Sequence
<220> FEATURE:
<223> OTHER INFORMATION: synthetic

<210> SEQ ID NO 119

<400> SEQUENCE: 119

```
gcaaaatacg gcagtggtta tggcaagttt tattattatg gaatggacgt g        51
```

<210> SEQ ID NO 120
<211> LENGTH: 17
<212> TYPE: PRT
<213> ORGANISM: Artificial Sequence
<220> FEATURE:
<223> OTHER INFORMATION: synthetic

<400> SEQUENCE: 120

```
Ala Lys Tyr Gly Ser Gly Tyr Gly Lys Phe Tyr Tyr Tyr Gly Met Asp
1               5                   10                  15
Val
```

<210> SEQ ID NO 121
<211> LENGTH: 372
<212> TYPE: DNA
<213> ORGANISM: Artificial Sequence
<220> FEATURE:
<223> OTHER INFORMATION: synthetic

<400> SEQUENCE: 121

```
gaagtacagc ttgtagaatc cggcggagga ctggtacaac ctggaagaag tcttagactg       60
agttgcgcag ctagtgggtt tacattcgac gattacagca tgcattgggt gaggcaagct      120
cctggtaaag gattggaatg ggttagcggg atatcatgga actcaggaag catcggatac      180
gccgacagcg tgaaaggccg atttacaata tctaggacaa acgcaaaaaa ctctctctac      240
cttcaaatga actctcttag ggcagaagac acagcattgt attattgcgc aaaagacggc      300
agtggttatg gcaagtttta ttattatgga ctggacgtgt ggggacaagg gacaacagtg      360
acagtgagta gc                                                          372
```

<210> SEQ ID NO 122
<211> LENGTH: 124
<212> TYPE: PRT
<213> ORGANISM: Artificial Sequence
<220> FEATURE:
<223> OTHER INFORMATION: synthetic

<400> SEQUENCE: 122

```
Glu Val Gln Leu Val Glu Ser Gly Gly Gly Leu Val Gln Pro Gly Arg
1               5                   10                  15
Ser Leu Arg Leu Ser Cys Ala Ala Ser Gly Phe Thr Phe Asp Asp Tyr
            20                  25                  30
Ser Met His Trp Val Arg Gln Ala Pro Gly Lys Gly Leu Glu Trp Val
        35                  40                  45
Ser Gly Ile Ser Trp Asn Ser Gly Ser Ile Gly Tyr Ala Asp Ser Val
    50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Leu Tyr Tyr Cys
                85                  90                  95
Ala Lys Asp Gly Ser Gly Tyr Gly Lys Phe Tyr Tyr Tyr Gly Leu Asp
            100                 105                 110
Val Trp Gly Gln Gly Thr Thr Val Thr Val Ser Ser
        115                 120
```

```
<210> SEQ ID NO 123
<211> LENGTH: 24
<212> TYPE: DNA
<213> ORGANISM: Artificial Sequence
<220> FEATURE:
<223> OTHER INFORMATION: synthetic

<400> SEQUENCE: 123
gggtttacat tcgacgatta cagc                                              24

<210> SEQ ID NO 124
<211> LENGTH: 8
<212> TYPE: PRT
<213> ORGANISM: Artificial Sequence
<220> FEATURE:
<223> OTHER INFORMATION: synthetic

<400> SEQUENCE: 124

Gly Phe Thr Phe Asp Asp Tyr Ser
1               5

<210> SEQ ID NO 125
<211> LENGTH: 24
<212> TYPE: DNA
<213> ORGANISM: Artificial Sequence
<220> FEATURE:
<223> OTHER INFORMATION: synthetic

<400> SEQUENCE: 125
atatcatgga actcaggaag catc                                              24

<210> SEQ ID NO 126
<211> LENGTH: 8
<212> TYPE: PRT
<213> ORGANISM: Artificial Sequence
<220> FEATURE:
<223> OTHER INFORMATION: synthetic

<400> SEQUENCE: 126

Ile Ser Trp Asn Ser Gly Ser Ile
1               5

<210> SEQ ID NO 127
<211> LENGTH: 51
<212> TYPE: DNA
<213> ORGANISM: Artificial Sequence
<220> FEATURE:
<223> OTHER INFORMATION: synthetic

<400> SEQUENCE: 127
gcaaaagacg gcagtggtta tggcaagttt tattattatg gactggacgt g                51

<210> SEQ ID NO 128
<211> LENGTH: 17
<212> TYPE: PRT
<213> ORGANISM: Artificial Sequence
<220> FEATURE:
<223> OTHER INFORMATION: synthetic

<400> SEQUENCE: 128

Ala Lys Asp Gly Ser Gly Tyr Gly Lys Phe Tyr Tyr Tyr Gly Leu Asp
1               5                   10                  15

Val

<210> SEQ ID NO 129
<211> LENGTH: 372
```

<212> TYPE: DNA
<213> ORGANISM: Artificial Sequence
<220> FEATURE:
<223> OTHER INFORMATION: synthetic

<400> SEQUENCE: 129

```
gaagtacagc ttgtagaatc cggcggagga ctggtacaac ctggaagaag tcttagactg    60
agttgcgcag ctagtgggtt tacattcgac gattacagca tgcattgggt gaggcaagct   120
cctggtaaag gattgaatg ggttagcggg atatcatgga actcaggaag catcggatac   180
gccgacagcg tgaaaggccg atttacaata tctagggaca acgcaaaaaa ctctctctac   240
cttcaaatga actctcttag ggcagaagac acagcattgt attattgcgc aaaagacggc   300
agtggttatg gcaagtttta tcattatgga atggacgtgt ggggacaagg gacaacagtg   360
acagtgagta gc                                                        372
```

<210> SEQ ID NO 130
<211> LENGTH: 124
<212> TYPE: PRT
<213> ORGANISM: Artificial Sequence
<220> FEATURE:
<223> OTHER INFORMATION: synthetic

<400> SEQUENCE: 130

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ser Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Gly Ser Gly Tyr Gly Lys Phe Tyr His Tyr Gly Met Asp
            100                 105                 110

Val Trp Gly Gln Gly Thr Thr Val Thr Val Ser Ser
        115                 120
```

<210> SEQ ID NO 131
<211> LENGTH: 24
<212> TYPE: DNA
<213> ORGANISM: Artificial Sequence
<220> FEATURE:
<223> OTHER INFORMATION: synthetic

<400> SEQUENCE: 131

```
gggtttacat tcgacgatta cagc                                            24
```

<210> SEQ ID NO 132
<211> LENGTH: 8
<212> TYPE: PRT
<213> ORGANISM: Artificial Sequence
<220> FEATURE:
<223> OTHER INFORMATION: synthetic

<400> SEQUENCE: 132

```
Gly Phe Thr Phe Asp Asp Tyr Ser
1               5
```

<210> SEQ ID NO 133
<211> LENGTH: 24
<212> TYPE: DNA
<213> ORGANISM: Artificial Sequence
<220> FEATURE:
<223> OTHER INFORMATION: synthetic

<400> SEQUENCE: 133
atatcatgga actcaggaag catc                                            24

<210> SEQ ID NO 134
<211> LENGTH: 8
<212> TYPE: PRT
<213> ORGANISM: Artificial Sequence
<220> FEATURE:
<223> OTHER INFORMATION: synthetic

<400> SEQUENCE: 134

Ile Ser Trp Asn Ser Gly Ser Ile
1               5

<210> SEQ ID NO 135
<211> LENGTH: 51
<212> TYPE: DNA
<213> ORGANISM: Artificial Sequence
<220> FEATURE:
<223> OTHER INFORMATION: synthetic

<400> SEQUENCE: 135
gcaaaagacg gcagtggtta tggcaagttt tatcattatg gaatggacgt g             51

<210> SEQ ID NO 136
<211> LENGTH: 17
<212> TYPE: PRT
<213> ORGANISM: Artificial Sequence
<220> FEATURE:
<223> OTHER INFORMATION: synthetic

<400> SEQUENCE: 136

Ala Lys Asp Gly Ser Gly Tyr Gly Lys Phe Tyr His Tyr Gly Met Asp
1               5                   10                  15
Val

<210> SEQ ID NO 137
<211> LENGTH: 372
<212> TYPE: DNA
<213> ORGANISM: Artificial Sequence
<220> FEATURE:
<223> OTHER INFORMATION: synthetic

<400> SEQUENCE: 137
gaagtacagc ttgtagaatc cggcggagga ctggtacaac tggaagaag tcttagactg      60 agttgcgcag ctagtgggtt tacattcgac gattacagca tgcattgggt gaggcaagct    120
cctggtaaag gattggaatg ggttagcggg atatcatgga actcaggaag catcggatac    180
gccgacagcg tgaaaggccg atttacaata tctagggaca cgcaaaaaa ctctctctac     240 cttcaaatga actctcttag ggcagaagac acagcattgt attattgcgc aaaatacggc    300
agtggttatg gcaagtttta ttattatgga atggacgtgt ggggacaagg gacaacagtg    360
acagtgagta gc                                                        372

<210> SEQ ID NO 138

<211> LENGTH: 124
<212> TYPE: PRT
<213> ORGANISM: Artificial Sequence
<220> FEATURE:
<223> OTHER INFORMATION: synthetic

<400> SEQUENCE: 138

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ser Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Tyr Gly Ser Gly Tyr Gly Lys Phe Tyr Tyr Tyr Gly Met Asp
            100                 105                 110

Val Trp Gly Gln Gly Thr Thr Val Thr Val Ser Ser
        115                 120
```

<210> SEQ ID NO 139
<211> LENGTH: 24
<212> TYPE: DNA
<213> ORGANISM: Artificial Sequence
<220> FEATURE:
<223> OTHER INFORMATION: synthetic

<400> SEQUENCE: 139
gggtttacat tcgacgatta cagc                                        24

<210> SEQ ID NO 140
<211> LENGTH: 8
<212> TYPE: PRT
<213> ORGANISM: Artificial Sequence
<220> FEATURE:
<223> OTHER INFORMATION: synthetic

<400> SEQUENCE: 140

Gly Phe Thr Phe Asp Asp Tyr Ser
1               5

<210> SEQ ID NO 141
<211> LENGTH: 24
<212> TYPE: DNA
<213> ORGANISM: Artificial Sequence
<220> FEATURE:
<223> OTHER INFORMATION: synthetic

<400> SEQUENCE: 141
atatcatgga actcaggaag catc                                        24

<210> SEQ ID NO 142
<211> LENGTH: 8
<212> TYPE: PRT
<213> ORGANISM: Artificial Sequence
<220> FEATURE:
<223> OTHER INFORMATION: synthetic

<400> SEQUENCE: 142

Ile Ser Trp Asn Ser Gly Ser Ile
1               5

<210> SEQ ID NO 143
<211> LENGTH: 51
<212> TYPE: DNA
<213> ORGANISM: Artificial Sequence
<220> FEATURE:
<223> OTHER INFORMATION: synthetic

<400> SEQUENCE: 143
gcaaaatacg gcagtggtta tggcaagttt tattattatg gaatggacgt g        51

<210> SEQ ID NO 144
<211> LENGTH: 17
<212> TYPE: PRT
<213> ORGANISM: Artificial Sequence
<220> FEATURE:
<223> OTHER INFORMATION: synthetic

<400> SEQUENCE: 144

Ala Lys Tyr Gly Ser Gly Tyr Gly Lys Phe Tyr Tyr Tyr Gly Met Asp
1               5                   10                  15
Val

<210> SEQ ID NO 145
<211> LENGTH: 372
<212> TYPE: DNA
<213> ORGANISM: Artificial Sequence
<220> FEATURE:
<223> OTHER INFORMATION: synthetic

<400> SEQUENCE: 145
gaagtacagc ttgtagaatc cggcggagga ctggtacaac ctggaagaag tcttagactg    60
agttgcgcag ctagtgggtt tacattcgac gattacagca tgcattgggt gaggcaagct   120
cctggtaaag gattgaatg ggttagcggg atatcatgga actcaggaag caagggatac   180
gccgacagcg tgaaaggccg atttacaata tctagggaca cgcaaaaaa ctctctctac   240
cttcaaatga actctcttag ggcagaagac acagcattgt attattgcgc aaaagacggc   300
agtggttatg gcaagttta ttattatgga atggacgtgt ggggacaagg acaacagtg    360
acagtgagta gc                                                       372

<210> SEQ ID NO 146
<211> LENGTH: 124
<212> TYPE: PRT
<213> ORGANISM: Artificial Sequence
<220> FEATURE:
<223> OTHER INFORMATION: synthetic

<400> SEQUENCE: 146

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ser Met His Trp Val Arg Gln Ala Pro Gly Lys Gly Leu Glu Trp Val
        35                  40                  45

Ser Gly Ile Ser Trp Asn Ser Gly Ser Lys Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
            85                  90                  95

Ala Lys Asp Gly Ser Gly Tyr Gly Lys Phe Tyr Tyr Tyr Gly Met Asp
        100                 105                 110

Val Trp Gly Gln Gly Thr Thr Val Thr Val Ser Ser
        115                 120

<210> SEQ ID NO 147
<211> LENGTH: 24
<212> TYPE: DNA
<213> ORGANISM: Artificial Sequence
<220> FEATURE:
<223> OTHER INFORMATION: synthetic

<400> SEQUENCE: 147
gggtttacat tcgacgatta cagc                                          24

<210> SEQ ID NO 148
<211> LENGTH: 8
<212> TYPE: PRT
<213> ORGANISM: Artificial Sequence
<220> FEATURE:
<223> OTHER INFORMATION: synthetic

<400> SEQUENCE: 148

Gly Phe Thr Phe Asp Asp Tyr Ser
1               5

<210> SEQ ID NO 149
<211> LENGTH: 24
<212> TYPE: DNA
<213> ORGANISM: Artificial Sequence
<220> FEATURE:
<223> OTHER INFORMATION: synthetic

<400> SEQUENCE: 149
atatcatgga actcaggaag caag                                          24

<210> SEQ ID NO 150
<211> LENGTH: 8
<212> TYPE: PRT
<213> ORGANISM: Artificial Sequence
<220> FEATURE:
<223> OTHER INFORMATION: synthetic

<400> SEQUENCE: 150

Ile Ser Trp Asn Ser Gly Ser Lys
1               5

<210> SEQ ID NO 151
<211> LENGTH: 51
<212> TYPE: DNA
<213> ORGANISM: Artificial Sequence
<220> FEATURE:
<223> OTHER INFORMATION: synthetic

<400> SEQUENCE: 151
gcaaaagacg gcagtggtta tggcaagttt tattattatg gaatggacgt g            51

<210> SEQ ID NO 152
<211> LENGTH: 17
<212> TYPE: PRT
<213> ORGANISM: Artificial Sequence
<220> FEATURE:
<223> OTHER INFORMATION: synthetic

<400> SEQUENCE: 152

Ala Lys Asp Gly Ser Gly Tyr Gly Lys Phe Tyr Tyr Tyr Gly Met Asp
1               5                   10                  15

Val

<210> SEQ ID NO 153
<211> LENGTH: 372
<212> TYPE: DNA
<213> ORGANISM: Artificial Sequence
<220> FEATURE:
<223> OTHER INFORMATION: synthetic

<400> SEQUENCE: 153
gaagtgcagc tggtggaaag cggcggcggc ctggtgcagc cgggccgcag cctgcgcctg     60
agctgcgcgg cgagcggctt tacctttgcg gattatacca tgcattgggt gcgccaggcg    120
ccgggcaaag gcctggaatg ggtgagcgat attagctgga acagcggcag cattgcgtat    180
gcggatagcg tgaaaggccg ctttaccatt agccgcgata acgcgaaaaa cagcctgtat    240
ctgcagatga acagcctgcg caccgaagat accgcgtttt attattgcgc gaaagatagc    300
cgcggctatg gccattataa atatctgggc ctggatgtgt ggggccaggg caccaccgtg    360
accgtgagca gc                                                        372

<210> SEQ ID NO 154
<211> LENGTH: 124
<212> TYPE: PRT
<213> ORGANISM: Artificial Sequence
<220> FEATURE:
<223> OTHER INFORMATION: synthetic

<400> SEQUENCE: 154

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ala Asp Tyr
            20                  25                  30

Thr Met His Trp Val Arg Gln Ala Pro Gly Lys Gly Leu Glu Trp Val
        35                  40                  45

Ser Asp Ile Ser Trp Asn Ser Gly Ser Ile Ala Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Thr Glu Asp Thr Ala Phe Tyr Tyr Cys
                85                  90                  95

Ala Lys Asp Ser Arg Gly Tyr Gly His Tyr Lys Tyr Leu Gly Leu Asp
            100                 105                 110

Val Trp Gly Gln Gly Thr Thr Val Thr Val Ser Ser
        115                 120

<210> SEQ ID NO 155
<211> LENGTH: 24
<212> TYPE: DNA
<213> ORGANISM: Artificial Sequence
<220> FEATURE:
<223> OTHER INFORMATION: synthetic

<400> SEQUENCE: 155
ggctttacct ttgcggatta tacc                                            24

<210> SEQ ID NO 156
<211> LENGTH: 8
<212> TYPE: PRT
<213> ORGANISM: Artificial Sequence
<220> FEATURE:
<223> OTHER INFORMATION: synthetic

<400> SEQUENCE: 156

Gly Phe Thr Phe Ala Asp Tyr Thr
1               5

<210> SEQ ID NO 157
<211> LENGTH: 24
<212> TYPE: DNA
<213> ORGANISM: Artificial Sequence
<220> FEATURE:
<223> OTHER INFORMATION: synthetic

<400> SEQUENCE: 157
attagctgga acagcggcag catt                                        24

<210> SEQ ID NO 158
<211> LENGTH: 8
<212> TYPE: PRT
<213> ORGANISM: Artificial Sequence
<220> FEATURE:
<223> OTHER INFORMATION: synthetic

<400> SEQUENCE: 158

Ile Ser Trp Asn Ser Gly Ser Ile
1               5

<210> SEQ ID NO 159
<211> LENGTH: 51
<212> TYPE: DNA
<213> ORGANISM: Artificial Sequence
<220> FEATURE:
<223> OTHER INFORMATION: synthetic

<400> SEQUENCE: 159
gcgaaagata gccgcggcta tggccattat aaatatctgg gcctggatgt g          51

<210> SEQ ID NO 160
<211> LENGTH: 17
<212> TYPE: PRT
<213> ORGANISM: Artificial Sequence
<220> FEATURE:
<223> OTHER INFORMATION: synthetic

<400> SEQUENCE: 160

Ala Lys Asp Ser Arg Gly Tyr Gly His Tyr Lys Tyr Leu Gly Leu Asp
1               5                   10                  15

Val

<210> SEQ ID NO 161
<211> LENGTH: 324
<212> TYPE: DNA
<213> ORGANISM: Artificial Sequence
<220> FEATURE:
<223> OTHER INFORMATION: synthetic

<400> SEQUENCE: 161
gacatccaga tgacccagtc tccatcctcc ctgtctgcat ctgtaggaga cagagtcacc    60
atcacttgcc gggcaagtca gagcattagc agctatttaa attggtatca gcagaaacca   120

```
gggaaagccc ctaagctcct gatctatgct gcatccagtt tgcaaagtgg ggtcccgtca    180
aggttcagtg gcagtggatc tgggacagat ttcactctca ccatcagcag tctgcaacct    240
gaagattttg caacttacta ctgtcaacag agttacagta ccctccgat caccttcggc     300 caagggacac gactggagat taaa                                            324
```

<210> SEQ ID NO 162
<211> LENGTH: 108
<212> TYPE: PRT
<213> ORGANISM: Artificial Sequence
<220> FEATURE:
<223> OTHER INFORMATION: synthetic

<400> SEQUENCE: 162

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105

<210> SEQ ID NO 163
<211> LENGTH: 18
<212> TYPE: DNA
<213> ORGANISM: Artificial Sequence
<220> FEATURE:
<223> OTHER INFORMATION: synthetic

<400> SEQUENCE: 163

```
cagagcatta gcagctat                                                   18
```

<210> SEQ ID NO 164
<211> LENGTH: 6
<212> TYPE: PRT
<213> ORGANISM: Artificial Sequence
<220> FEATURE:
<223> OTHER INFORMATION: synthetic

<400> SEQUENCE: 164

Gln Ser Ile Ser Ser Tyr
1               5

<210> SEQ ID NO 165
<211> LENGTH: 9
<212> TYPE: DNA
<213> ORGANISM: Artificial Sequence
<220> FEATURE:
<223> OTHER INFORMATION: synthetic

<400> SEQUENCE: 165

```
gctgcatcc                                                             9
```

<210> SEQ ID NO 166

```
<211> LENGTH: 3
<212> TYPE: PRT
<213> ORGANISM: Artificial Sequence
<220> FEATURE:
<223> OTHER INFORMATION: synthetic

<400> SEQUENCE: 166

Ala Ala Ser
1

<210> SEQ ID NO 167
<211> LENGTH: 30
<212> TYPE: DNA
<213> ORGANISM: Artificial Sequence
<220> FEATURE:
<223> OTHER INFORMATION: synthetic

<400> SEQUENCE: 167
caacagagtt acagtacccc tccgatcacc                                          30

<210> SEQ ID NO 168
<211> LENGTH: 10
<212> TYPE: PRT
<213> ORGANISM: Artificial Sequence
<220> FEATURE:
<223> OTHER INFORMATION: synthetic

<400> SEQUENCE: 168

Gln Gln Ser Tyr Ser Thr Pro Pro Ile Thr
1               5                   10

<210> SEQ ID NO 169
<211> LENGTH: 124
<212> TYPE: PRT
<213> ORGANISM: Artificial Sequence
<220> FEATURE:
<223> OTHER INFORMATION: synthetic

<400> SEQUENCE: 169

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ala Asp Tyr
            20                  25                  30

Thr Met His Trp Val Arg Gln Ala Pro Gly Lys Cys Leu Glu Trp Val
        35                  40                  45

Ser Asp Ile Ser Trp Asn Ser Gly Ser Ile Ala Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Thr Glu Asp Thr Ala Phe Tyr Tyr Cys
                85                  90                  95

Ala Lys Asp Ser Arg Gly Tyr Gly His Tyr Lys Tyr Leu Gly Leu Asp
            100                 105                 110

Val Trp Gly Gln Gly Thr Thr Val Thr Val Ser Ser
        115                 120

<210> SEQ ID NO 170
<211> LENGTH: 124
<212> TYPE: PRT
<213> ORGANISM: Artificial Sequence
<220> FEATURE:
<223> OTHER INFORMATION: synthetic
```

<400> SEQUENCE: 170

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ser Met His Trp Val Arg Gln Ala Pro Gly Lys Cys Leu Glu Trp Val
        35                  40                  45

Ser Gly Ile Ser Trp Asn Ser Gly Ser Lys Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Tyr Gly Ser Gly Tyr Gly Lys Phe Tyr His Tyr Gly Leu Asp
            100                 105                 110

Val Trp Gly Gln Gly Thr Thr Val Thr Val Ser Ser
        115                 120

<210> SEQ ID NO 171
<211> LENGTH: 5
<212> TYPE: PRT
<213> ORGANISM: Artificial Sequence
<220> FEATURE:
<223> OTHER INFORMATION: synthetic

<400> SEQUENCE: 171

Gly Gly Gly Gly Ser
1               5

<210> SEQ ID NO 172
<211> LENGTH: 10
<212> TYPE: PRT
<213> ORGANISM: Artificial Sequence
<220> FEATURE:
<223> OTHER INFORMATION: synthetic

<400> SEQUENCE: 172

Gly Gly Gly Gly Ser Gly Gly Gly Gly Ser
1               5                   10

<210> SEQ ID NO 173
<211> LENGTH: 15
<212> TYPE: PRT
<213> ORGANISM: Artificial Sequence
<220> FEATURE:
<223> OTHER INFORMATION: synthetic

<400> SEQUENCE: 173

Gly Gly Gly Gly Ser Gly Gly Gly Gly Ser Gly Gly Gly Gly Ser
1               5                   10                  15

<210> SEQ ID NO 174
<211> LENGTH: 20
<212> TYPE: PRT
<213> ORGANISM: Artificial Sequence
<220> FEATURE:
<223> OTHER INFORMATION: synthetic

<400> SEQUENCE: 174

Gly Gly Gly Gly Ser Gly Gly Gly Gly Ser Gly Gly Gly Gly Ser Gly
1               5                   10                  15

Gly Gly Gly Ser
        20

<210> SEQ ID NO 175
<211> LENGTH: 25
<212> TYPE: PRT
<213> ORGANISM: Artificial Sequence
<220> FEATURE:
<223> OTHER INFORMATION: synthetic

<400> SEQUENCE: 175

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 176
<211> LENGTH: 30
<212> TYPE: PRT
<213> ORGANISM: Artificial Sequence
<220> FEATURE:
<223> OTHER INFORMATION: synthetic

<400> SEQUENCE: 176

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 177
<211> LENGTH: 35
<212> TYPE: PRT
<213> ORGANISM: Artificial Sequence
<220> FEATURE:
<223> OTHER INFORMATION: synthetic

<400> SEQUENCE: 177

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly
            20                  25                  30

Gly Gly Ser
        35

<210> SEQ ID NO 178
<211> LENGTH: 40
<212> TYPE: PRT
<213> ORGANISM: Artificial Sequence
<220> FEATURE:
<223> OTHER INFORMATION: synthetic

<400> SEQUENCE: 178

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser
        35                  40

<210> SEQ ID NO 179
<211> LENGTH: 45
<212> TYPE: PRT
<213> ORGANISM: Artificial Sequence
<220> FEATURE:

```
<223> OTHER INFORMATION: synthetic

<400> SEQUENCE: 179

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser
        35                  40                  45

<210> SEQ ID NO 180
<211> LENGTH: 50
<212> TYPE: PRT
<213> ORGANISM: Artificial Sequence
<220> FEATURE:
<223> OTHER INFORMATION: synthetic

<400> SEQUENCE: 180

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly
        35                  40                  45

Gly Ser
    50
```